(12) United States Patent
Colussi et al.

(10) Patent No.: US 8,664,374 B2
(45) Date of Patent: Mar. 4, 2014

(54) POLYPEPTIDE EXPRESSION IN CILIATES

(75) Inventors: Paul Colussi, Gloucester, MA (US); Donna Cassidy-Hanley, Ithaca, NY (US); Theodore G. Clark, Ithaca, NY (US)

(73) Assignee: Tetragenetics, Inc., Cambridge, MA (US)

( * ) Notice: Subject to any disclaimer, the term of this patent is extended or adjusted under 35 U.S.C. 154(b) by 0 days.

(21) Appl. No.: 13/237,653

(22) Filed: Sep. 20, 2011

(65) Prior Publication Data

US 2012/0129217 A1 May 24, 2012

Related U.S. Application Data

(63) Continuation of application No. PCT/US2010/028168, filed on Mar. 22, 2010.

(60) Provisional application No. 61/162,138, filed on Mar. 20, 2009, provisional application No. 61/162,142, filed on Mar. 20, 2009.

(51) Int. Cl.
*C07H 21/04* (2006.01)
*C12N 1/00* (2006.01)

(52) U.S. Cl.
USPC ...................... 536/23.1; 435/258.1

(58) Field of Classification Search
None
See application file for complete search history.

(56) References Cited

U.S. PATENT DOCUMENTS

| | | | |
|---|---|---|---|
| 6,087,124 | A | 7/2000 | Steinbruck et al. |
| 2005/0106164 | A1 | 5/2005 | Gaertig et al. |
| 2006/0127973 | A1 | 6/2006 | Hartmann et al. |

FOREIGN PATENT DOCUMENTS

| | | |
|---|---|---|
| WO | WO-9801572 A1 | 1/1998 |
| WO | WO-03078566 A2 | 9/2003 |
| WO | WO-2007006812 A1 | 1/2007 |

OTHER PUBLICATIONS

Cassidy-Hanley, D. et al. "Germline and Somatic Transformation fo Mating *Tetrahymena thermophila* by Paticle Bombardment." Genetics. Genetics Society of America, Austin, TX. vol. 146, No. 1, May 1, 1997. pp. 135-147.
European Search Report for European Patent Application No. 10754236.7 mailed Nov. 16, 2012. 4 pages.
Bruns et al. "Biolistic Transformation of Macro and Micronuclei." Methods in Cell Biology, vol. 62, Asai & Forney (eds.), Academic Press. No Month Listed. 1999. pp. 501-512. 12 pages.
Bruns, et al., "A Drug-Resistant Mutation in the Ribosomal DNA of *Tetrahymena*", Proc. Natl. Acad.Sci., vol. 82:2844-2846, May 1985. 3 pages.
Coyne, et al., "Evolutionary Conservation of Sequences Directing Chromosomes Breakage and rDNA Palindrome Formation in *Tetrahymenine* Ciliates", Proc. Nat'l Acad. Sci. Genetics, 144(4):1479-1487, Dec. 1996. 9 pages.
Fan et al. "A Long Stringent Sequence Signal for Programmed Chromosome Breakage in *Tetrahymena thermophila*." Nucleic Acid Res. Feb. 15, 2000; 28(4): 895-900. 6 pages.
Gaertig, et al. "Surface Display of a Parasite Antigen in the Ciliate *Tetrahymena thermophila*." Nature Biotech, 17:462-465, May 1999.
Gaertig, et al., "Efficient Mass Transformation of *Tetrahymena thermophila* by Electroportation of Conjugants", Proc. Natl. Acad. Sci., 89:9196-9200, Oct. 1992. 5 pages.
Gaertig, et al., "High Frequency Vector-Mediated Transformation and Gene Replacement in *Tetrahymena*", Nucleic Acids Res., 22:5391-5398, Oct. 1994. 8 pages.
Hai, et al. "Knockout Heterokaryons Enable Facile Mutagenic Analysis of Essential Genes in *Tetrahymena*." Methods in Cell Biology, vol. 62, No Month Listed. 1999. pp. 513-531. 19 pages.
Hamilton et al. "The Highly Conserved Family of *Tetrahymea thermophila* Chromosome Breakage Elements Contains an Invariant 10-Base-Pair Core." Eukaryotic Cell., Apr. 2006. vol. 5, No. 4, pp. 771-780. 10 pages.
Hausmann, K. "Extrusive Organelles in Protists." Int. Rev. CytoL. No Month Listed. 1978. pp. 197-276. 80 pages.
Hunseler, et al. "Genetic Characterization of the Secretory Mutant MS-1 of *Tetrahymena thermophila*: Vacuolarization and Block in Secretion of Lysosomal Hydrolases are Caused by a Single Gene Mutation." Dev. Genet. Wiley-Liss, Inc. No Month Listed 1992. 13:167-173. 7 pages.
Kapler et al. "*Tetrahymena thermophil* mutants defective in the developmentally programmed maturation and mainteannce of the rdna minichromosome." Genetics. Jun. 1994. 137(2) pp. 455-466. 12 pages.
Larson, et al., "Control of rDNA Replication in *Tetrahymena* Involves a As-Acting Upstream Repeat of a Promoter Element", Cell Press., 47:229-240, Oct. 1986. 12 pages.
MacAlpine, et al., "Type I Elements Mediate Replication Fork Pausing at Conserved Upstream Sites in the *Tetrahymena thermophila* Ribosomal DNA Minichromosome", Mol. Cell. Biol., American Soc. Of Microbiology. 17:4517-4525, Aug. 1997. 9 pages.
Miller et al. "Regulated Secretion," Curr. Opin. Cell Biol. No Month Listed. 1990. 2:642-647. 6 pages.
Orias, et al., "Replacement of the Macronuclear Ribosomal RNA Genes of a Mutant *Tetrahymena* Using Electroporation", Gene, 2:295-301, Jul. 1988. Elsevier Sci. Publishers. 7 pages.
Pan, et al., "Allele-Specific. Selective Amplification of Ribosomal RNA Gene in *Tetrahymena thermophila*", Cell, 3:595-604, Mar. 1982. 10 pages.

(Continued)

*Primary Examiner* — Michele K Joike
(74) *Attorney, Agent, or Firm* — Wilmer Cutler Pickering Hale and Dorr LLP

(57) ABSTRACT

This invention is directed to methods for recombinant polypeptide production and, in particular, methods and products for the production of recombinant polypeptides in ciliates.

26 Claims, 20 Drawing Sheets

(56) References Cited

OTHER PUBLICATIONS

Pan, et al., "Replication of an rRNA Gene Origin Plasmid in the *Tetrahymena thermophila* Macronucleus is Prevented by Transcription through the Origin from an RNA Polymearse I Promoter", Mol. Cell. Biol. 15:3372-3381, Jun. 1995. American Soc. Of Microbiology. 10 pages.

Rosati, G. and Modeo, L., "Extrusomes in ciliates: diversification, distribution and phylogenetic implications". Journal of Eukaryotic Microbiology 50, 383-402. Int'l Soc. Of Protistologists, Nov.-Dec. 2003. 21 pages.

Spangler, et al., "The Nucleotide Sequence of the 17S Ribosomal RNA Gene of *Tetrahymena thermophila* and the Identification of Point Mutations Resulting in Resistance to the Antibiotics Paromomycin and Hygromycin", J. Biol. Chem., vol. 260, No. 10. :6334-6340, American Society of Biological Chemists, Inc. May 1985. 7 pages.

Tondravi, et al., "Transformation of *Tetrahymena thermophila* by Microinjection of Ribosomal RNA Genes", Proc. Natl. Acad. Sci., 83:4369-4373, Jun. 1986. 5 pages.

Turkewitz, et al., "Functional Genomics: the Coming of Age for *Tetrahymena thermophila*", Trends Genet., 18:35-40, Jan. 2002. 6 pages.

Weide, et al., "Secretion of Functional Human Enzymes by *Tetrahymena thermophila*", BCM Biotechnol, vol. 19, Mar. 2006. 9 pages.

Yaeger, et al., "The Replication Advantage of a Free Liner rDNA Gene is I~estored by Somatic Recombination in *Tetrahymena thermophila*", Mol. Cell. Biol., 9:452-460, Feb. 1989. American Soc. For Microbiology. 9 pages.

Yakisich, et al., "Deletion of the *Tetrahymena thermophila* rDNA Replication Fork Barrier Region Disrupts Macronuclear rDNA Excision and Creates a Fragile Site in the Micronuclear Genome", Nucleic Acids Res., 34(2):620-634, Jan. 30, 2006. 15 pages.

Yao, et al., "A Conserved Nucleotide Sequence at the Sites of Developmentally Regulated Chromosomal Breakage in *Tetrahymena*", Cell, 48:779-788, Mar. 1987. Cell Press. 10 pages.

Yao, et al., "The Controlling Sequence for Site-Specific Chromosome Breakage in *Tetrahymeno*", Cell, 63:763-772, Nov. 1990. Cell Press. 10 pages.

Yu, et al., "Circular Ribosomal DNA Plasmids Transform *Tetrahymena thermophilia* by Homologous Recombination with Endogenous Macronuclear Ribosomal DNA", Proc. Natl. Acad. Sci., 14:5151-5155, Jul. 1988. 5 pages.

Yu, et al., "Developmentally Programmed Healing of Chromosomes by Telomerase in *Tetrahymena*", Cell, 67:823-832, Nov. 1991. Cell Press. 10 pages.

Yu, et al., "Transformation of *Tetrahymena thermophelia* with a Mutated Circular Ribosomal DNA Plasmid Vector", Proc. Natl. Acad. Sci, 21:8487-8491, Nov. 1989. 5 pages.

Blomberg et al., "Regulatory Sequences for the Ampilication and replication of the ribosomal DNA Minichromosome in *Tetrahymena* thermophila," Molecular and Cellular Biology, vol. 17, pp. 7237-7247 (Dec. 1997).

Sweeney et al., "A Mutation in the large Subunit Ribosomal Rna gene of *Tetrahymena* confers anisomycin resistance and cold sensitivity," Genetics, vol. 127, pp. 327-334 (Feb. 1991).

Yao et al., "Transformation of *Tetrahymena* to cycloheximide resistance with a ribosomal protein gene through sequence replacement," Proc. Natl. Acad. Sci. USA, vol. 88, pp. 9493-9497 (Nov. 1991).

Sweeney et al., "Identifying functional regions of rRNA by insertion mutagenesis and complete gene replacement in *Tetrahymena* thermophila," The EMBO Journal, vol. 8, pp. 933-938 (1989).

International Search Report and Written Opinion mailed on Aug. 5, 2010, for International Application No. PCT/US10/28168 filed Mar. 22, 2010.

```
   1 ttttaactta tttttaaaaa ttaaaccaac ctctttgttt atttaaatat aatttatttt
  61 taattaattc atttattgat aatgcataag tagcatattt ttaatacatt attgataatt
 121 ttctgttact aatagcttgg ctgcaggtcg acggatcccc gggaattcat cgatatctag
 181 atctcgagct cgcgaaagct tggcactggc cgtcgtttta caacgtcgtg actgggaaaa
 241 ccctggcgtt acccaactta atcgccttgc agcacatccc cctttcgcca gctggcgtaa
 301 tagcgaagag gcccgcaccg atcgccttc ccaacagttg cgcagcctga atggcgaatg
 361 gcgcctgatg cggtattttc tccttacgca tctgtgcggt atttcacacc gcatatggtg
 421 cactctcagt acaatctgct ctgatgccgc atagttaagc cagccccgac acccgccaac
 481 acccgctgac gcgccctgac gggcttgtct gctcccggca tccgcttaca gacaagctgt
 541 gaccgtctcc gggagctgca tgtgtcagag gttttcaccg tcatcaccga aacgcgcgag
 601 acgaaaggc ctcgtgatac gcctattttt ataggttaat gtcatgataa taatggtttc
 661 ttagacgtca ggtggcactt ttcggggaaa tgtgcgcgga acccctattt gtttatttt
 721 ctaaatacat tcaaatatgt atccgctcat gagacaataa ccctgataaa tgcttcaata
 781 atattgaaaa aggaagagta tgagtattca acatttccgt gtcgcccta ttccctttt
 841 tgcggcattt tgccttcctg tttttgctca cccagaaacg ctggtgaaag taaaagatgc
 901 tgaagatcag ttgggtgcac gagtgggtta catcgaactg gatctcaaca gcggtaagat
 961 ccttgagagt tttcgccccg aagaacgttt tccaatgatg agcacttta aagttctgct
1021 atgtggcgcg gtattatccc gtattgacgc cgggcaagag caactcggtc gccgcataca
1081 ctattctcag aatgacttgg ttgagtactc accagtcaca gaaaagcatc ttacggatgg
1141 catgacagta agagaattat gcagtgctgc cataaccatg agtgataaca ctgcggccaa
1201 cttacttctg acaacgatcg gaggaccgaa ggagctaacc gcttttttgc acaacatggg
1261 ggatcatgta actcgccttg atcgttggga accggagctg aatgaagcca taccaaacga
1321 cgagcgtgac accacgatgc ctgtagcaat ggcaacaacg ttgcgcaaac tattaactgg
1381 cgaactactt actctagctt cccggcaaca attaatagac tggatggagg cggataaagt
1441 tgcaggacca cttctgcgct cggcccttcc ggctggctgg tttattgctg ataaatctgg
1501 agccggtgag cgtgggtctc gcggtatcat tgcagcactg gggccagatg gtaagccctc
1561 ccgtatcgta gttatctaca cgacggggag tcaggcaact atggatgaac gaaatagaca
1621 gatcgctgag ataggtgcct cactgattaa gcattggtaa ctgtcagacc aagtttactc
1681 atatatactt tagattgatt taaaacttca tttttaattt aaaaggatct aggtgaagat
1741 cctttttgat aatctcatga ccaaaatccc ttaacgtgag ttttcgttcc actgagcgtc
1801 agacccgta gaaaagatca aggatcttc ttgagatcct ttttttctgc gcgtaatctg
1861 ctgcttgcaa acaaaaaaac caccgctacc agcggtggtt tgtttgccgg atcaagagct
1921 accaactctt tttccgaagg taactggctt cagcagagcg cagataccaa atactgtcct
1981 tctagtgtag ccgtagttag gccaccactt caagaactct gtagcaccgc ctacatacct
2041 cgctctgcta atcctgttac cagtggctgc tgccagtggc gataagtcgt gtcttaccgg
2101 gttggactca agacgatagt taccggataa ggcgcagcgg tcgggctgaa cggggggttc
2161 gtgcacacag cccagcttgg agcgaacgac ctacaccgaa ctgagatacc tacagcgtga
2221 gctatgagaa agcgccacgc ttcccgaagg gagaaaggcg acaggtatc cggtaagcgg
2281 cagggtcgga acaggagagc gcacgaggga gcttccaggg gaaacgcct ggtatcttta
2341 tagtcctgtc gggtttcgcc acctctgact tgagcgtcga ttttgtgat gctcgtcagg
2401 ggggcggagc tatggaaaa acgccagcaa cgcggccttt tacggttcc tggccttttg
2461 ctggcctttt gctcacatgt tctttcctgc gttatcccct gattctgtgg ataaccgtat
2521 taccgccttt gagtgagctg ataccgctcg ccgcagccga acgaccgagc gcagcgagtc
2581 agtgagcgag gaagcggaag agcgcccaat acgcaaaccg cctctccccg cgcgttggcc
2641 gattcattaa tgcagctggc acgacaggtt cccgactgg aaagcgggca gtgagcgcaa
2701 cgcaattaat gtgagttagc tcactcatta ggcaccccag gctttacact ttatgcttcc
2761 ggctcgtatg ttgtgtggaa ttgtgagcgg ataacaattt cacacaggaa acagctatga
2821 ccatgattac gccatcgaaa aataatata tcctcccatg tagacctccc ataaaaact
2881 cagatttcat ttttcaaggt gaatatatga ggcatattca agtatttgat atgaaaaaa
2941 gtaaaaagtc taagtctcgc taacagcaaa tatgagtttg tttttgcttt gatttaata
3001 aatacaaaat aacaaatatt aaacaaata gagctgtata ttatgcctaa ccaattaaat
3061 gccatttatt aagcaaaatt atagtgttta aatacaatca tatagttaca aaaatgtttg
3121 aggttagcta gattttgtct agagtactta atctcacttt ccagataagt ctactttaat
3181 aataatttca ttatattaca aacaaacaaa taattataat ttaaatttta atctgaataa
3241 actcgataaa atggaagcaa aaacttccac ttctaatcct tgattttaat tatactatat
3301 tataaatatg aattgaaaaa tctaatgtat gctttaactt atatagatat ataaatatta
```

Figure 4A

```
3361 tttcttgtaa ttcttataaa cgattgtttt atatatctaa attattatta cttaatatta
3421 atcataatgt ttgatttctg atgcaaacct taacaaaaat ccaacaaata ttttatttaa
3481 aaacaaatgt atttgttcac ttcatatata tgaaaaaata atagaatttc aatactaaat
3541 taaataccaa gataaaattc ttaaattaat tttttttta tcagttataa aaatagtgtt
3601 tcatgtaaat aaaattaaaa tattttaaa atataaattt aatccaatat tactaactaa
3661 atagataaaa atagttaatt ataaatatat taataagcac tttaagtaaa agaatatttt
3721 tcttttattt tatttaaatt aatttaaaaa taaattcaaa aattatataa tggctttaaa
3781 ttttgataat aaataagaaa gaatatttaa aattataatt ttaataaaat gagaacaaac
3841 aaattaaata ttgtaatttc taatttaatt agattttcaa aataaatgag gttggtttat
3901 ttcaatcaat gattaaattt atattaaaga aagaggttgg tttatttcaa tcaaaaatta
3961 aatttatatt aaagaaagag gttggtttat taatattaaa agcgattttc gaaggtaaaa
4021 ttcaacaaca tagtgctgaa ggctagtttt tttgcttttt gttgttagtt ttatagcctt
4081 cagcactatg ttgttgaatt ttaccttcga aaatAactta aaattgagta ataattgggt
4141 ttaaaattta aatttgagta gataagaatt agatgtttat attctgctaa tttcactggt
4201 gaaaatgtag caaatagaaa ttattttaat ctaataaact agcaaatagt atttaaaaca
4261 aaaatatttg tttttatgt tgtaaaatgt tttaaattag ataaaattta caaatttaca
4321 aattttcaag caaaataggt tctaaaaaat gagaaaatat tacatatttt agctatttga
4381 ctactttaat gctagtaaat taaaatgaat ttaattcatt ttcactttaa aacacttatt
4441 ttaataaaat atatgatttt aaaatgataa aatattttt aagaggtaaa tttaagaaat
4501 tagttaaatt ttaaagaaaa agcatctaaa aatggacaaa aatgaagtat ttccttttt
4561 tatacattta aatgctagaa aatttaagta aaacatttat aataaaagt aaaatagttt
4621 taggaataAg agtaaatagt ttttttatg taaaaaacat tttatcaatt tcatttattc
4681 attttagtta aattttcat tcacaaaaaa ctttttttg gtaaaataaa gactttataa
4741 agataactta aagaaaagt ttatctagaa ttaaaaatat tgattttgaa aattgctcat
4801 tagatatttt tttggcaaaa aaaaaaacaa aaatagtaaa aaatcacttt ttttgagagt
4861 tgaaaaaaag acttagaaaa aattttaaaa gtgtaaaaaa agacttagag aaaaaatcaa
4921 aaagagataa aaagacttag agaaaattta taaattaaaa atgatagaaa agtaaaattt
4981 attttatatt ttttaatcat ttaaatgcta gtaaatttaa ataaaacata tataaaaaaa
5041 cataaaacaa ttttaacaAc atgcgtatat cattttttat atgtaaaaaa cattttatca
5101 atttcattta ttcattttag ttaaattta cattcaaaat aaattttttt tgattaaata
5161 aagagttata aagagaactt aaagaaaaag tttatctaga attaaaaata ttgattttga
5221 aaattgctca ttagaaattt ttttggcaaa aaaaaaaaca aaaatagtaa ac
```

CTTCCGAACTTTTGCAACTTTTGAGACTTCGTgaaaaaagac ttagaaaa
```
5281 attttgaaa aatgaaaaaa aaagacttag agaaaaaaat caaaaaAgtga aaaaagactt
5341 agaaaatttt ttTaaaatga aaaatgatt taggagaaat tttgagattg cgcttagatt
5401 ttgtgtgaag Tcacttacaa aaaatgagcg gactcgctca aatatttaag tggactcgca
5461 taaaatgag tggagtcact aaaaaaGtta agtgaactca cttaaaaatg agtggagcca
5521 ctcaaaaaat taagcggact cgcttaatat tcgcggagtt aaacaaaaat aagtggactc
5581 acagaaaaat taagcggatt gcgctaaaaa atgagtggac tcactcaaaa atgaagcaga
5641 ctcgcttaaa aatgagtgga gccactcaa aagttcagca gagccactta aaaatttagc
5701 ttaaaatcag ctctaaatta aattagactt agtgaaaaat agcgaaaatg aaaaaaatga
5761 aaaatgaat gaaaactgaa aaatttacaa gggattgaaa attttggcag agtcttttt
5821 ttggcaaaaa aaaaacaaa aatagtaaac cttccgaact ttttgactt tgagaaaaat
5881 tctttggcaa aaaaaataaa aataatatca gggggtaaa aatgcatatt taagaagggg
5941 aaacatctcc ggatcaaaaa taaaatatca gctcgatttg agcttcagta agatttcctt
6001 ttgggcaacc aaggataacg ataatgaagc gctaactgag cagacgtttt tctctatggc
6061 ttcggctttt agtcgatggc cgctgagggt ctgttgaagg ttttttctgga ttaaggctcg
6121 tattagagca aatggcctga ctgaaatttt catgaaggct gtaaattcac tgcaaagctt
6181 cgcagaaact tttcccagtg acacttgttg tatcgatatc tatgcagata ttgttacaaa
6241 taacgcaaca cgctagtact gttataaatc ggtgaaatcg cagatgttat taacagctag
6301 caacaaagtt gactagagtc gaagagatgc gatagagttt tctcattgtg ccttcgaaga
6361 ttttagcaac tagaagaaac taatagtaaa cgaaacgatg cgggatctat gtataaagct
6421 taatctaacg atatagctga gtactgatct attacaacgc gtcagttctc gatgaactat
```

Figure 4B

```
6481 taatcttttg tgaaccaacc ttttggaaca ctattcaaaa aatgagcaag ctgttggaag
6541 atgcaaatcg gaaatagcg agcaaatttt gaggatagta acctggttga tcctgccagt
6601 tacatatgct tgtcttaaat attaacccat gcatgtgcca gttcagtatt gaacagcgaa
6661 actgcgaatg gctcattaaa acagttatag tttatttgat aattaaagat tacatggata
6721 accgagctaa ttgttgggct aatacatgct taaaattccg tgtcctgcga ccggaacgta
6781 tttattagat attagaccaa tcgcagcaat gtgattgaga tgaatcaaag taactgatcg
6841 gatcgaggtt tacctcgata aatcatctaa gtttctgccc tatcagctct cgatggtagt
6901 gtattggact accatggcag tcacgggtaa cggagaatta gggttcgatt ccggagaagg
6961 agcctgagaa acggctacta caactacggt tcggcagcag ggaagaaaat tggccaatcc
7021 taattcaggg agccagtgac aagaaatagc aagctgggaa acttacgttt ctacggcatt
7081 gaaatgagaa cagtgtaaat ctcttagcga ggaacaattg gagggcaagt catggtgcca
7141 gcagccgcgg taattccagc tccaatagcg tatattaaag ttgttgcagt taaaaagctc
7201 gtagttgaac ttctgttcag gttcatttcg attcgtcgtg tgaaactgga catacgtttg
7261 caaactaaaa tcggccttca ctggttcgac ttagggagta aacattttac tgtgaaaaaa
7321 ttagagtgtt ccaggcaggt tttagcccga atacattagc atggaataat gaataggac
7381 taagtccatt ttattggttc ttggatttgg taatgattaa tagggacagt tggggggcatt
7441 agtatttaat agtcagaggt gaaattcttg gatttattaa ggactaacta atgcgaaagc
7501 atttgccaaa gatgttttca ttaatcaaga acgaaagtta ggggatcaaa gacgatcaga
7561 taccgtcgta gtcttaacta taaactatac cgactcggga tcggctggaa taaatgtcca
7621 gtcggcaccg tatgagaaat caaagtcttt gggttctggg ggaagtatgg tacgcaagtc
7681 tgaaacttaa aggaattgac ggaacagcac accagaagtg gaacctgcgg cttaatttga
7741 ctcaacacgg ggaaactcac gagcgcaaga cagagaaggg attgacagat tgagagctct
7801 ttcttgattc tttgggtggt ggtcatggc cgttctagt tggtggagtg atttgtctgg
7861 ttaattccgt taacgaacga gaccttaacc tgctaactag tctgcttgta aataacaggt
7921 tgtacttctt agagggacta ttgtgcaata agccaatgga agtttaaggc aataacaggt
7981 ctgtgatgcc cctagacgtg ctcggccgca cgcgcgttac aatgctgaca gcaaaaagta
8041 tttcctgtcc tgggaaggta cgggtaatct tattaatacc agtcgtgtta gggatagttc
8101 tttggaattg tggatcttga acgaggaatt tctagtaagt gcaagtcatc agcttgcgtt
8161 gattatgtcc ctgccgtttg tacacaccgc ccgtcgcttg tagtaacgaa tggtctggtg
8221 aaccttctgg actgcgacag caatgttgcg gaaaaataag taaaccctac catttggaac
8281 aacaaGaagt cgtaacaagg tatctgtagg tgaacctgca gatggatcat taacacaatt
8341 aacaaacctt aacttatgta ctttcgaaga gaacttcggt tttcttcgag tgtttattgt
8401 cacacctagt gtgaataaaa attttttcata tgtctaagat ctggataaca tccaaaacga
8461 aaagaaaact ttcaacggtg gatatctagg ttcccgtgac gatgaagaac gcagcgaaat
8521 gcgatacgca atgcgaattg cagaaccgcg agtcatcaga tctttgaacg caagtggtgg
8581 aggtgtaaaa accttcatgt ttgtttcagt gtggaaagga atcacgcatc ttaatgcgat
8641 tgaagccgtc aaaagcttct ctcgttaaac gtgatgggtg gtcgagcaat cgccgccaga
8701 acgaagtagt cacattccag taatgtgaac attcgttcag gcatcaaggc gaatgctcac
8761 tatgctactc atagaaaaat tacattttc tcactacacc tgaaacaagc aagattaccc
8821 gctgaactta agcatatcag taagcggagg aaaagaaact aactaggata gccccagtaa
8881 tggcgaatga acaggctaaa gctcaaagtg aaaatctgaa gtggtcaaca caacagaatt
8941 gtaatctaaa gggtcaacct gaaactaagc tcctctcata agttccttgg gacaggacgt
9001 caaagagggt gacaaccccg tagtcggaga ggaaggctgg tgtaagggag atttcaaaga
9061 gtcgggttgt ttggaattgc agccctaagt gggagataaa cttcttctaa agctaaatat
9121 acacgggaga ccgatagcga acaagtactg cgaaggaaag atgaaaagaa ctttgaaaag
9181 agggctaaaa gacttgaaac cgttgagaag gaagctgtag aagagcaata aactggacgg
9241 cgcataaggg ggaagtacta atcactgcag agtcgatacg taaaaggtcg atgagtaagg
9301 aaatggtaca gaacttgcta caccggtcag aagacaaaat gggttcagat tgaaggagtc
9361 acctgagatc gggcagcaat gcagatcaag aggaaaactt caaactggac tgagggcct
9421 aaggggcgatt ttgtcaaaat ggcttctact gacccgtctt gaaacacgga ccaaggagtc
9481 tatcaattaa gcgagtgata gggtggaaaa acccgtccgc gaaacgaaag tgagtacaag
9541 gtgccaagcc gcaaggtagc agcatcaccc gccttgagtc tccgcgaagg gttcgaggaa
9601 gagcttaatt gttaggaccc gaaagatggt gaactacgct tgaatagggt gaagccaggg
9661 gaaactctgg tggaagctcg tagcgatact gacgtgcaaa tcgttcgtca aatttgagtg
9721 taggggcgaa agactaatcg aaccatctag tagctggttc cctccgaagt ttctctcagg
```

Figure 4C

```
 9781 atagcaagag caagtacgca gttttattag gtaaagcgaa tgattgaagg actcgggagt
 9841 cctaagaact tcgacctatt ctcaaacttt aaattggtaa gagccgcgga gtttacttaa
 9901 atgaactctc gggaagaacg cagtgctctt gagttgggcc attttggta agcagaactg
 9961 gcgatgaggg atgaacctaa cgttgagata aggcgcccaa atgcacgctc atcagatacc
10021 acaaaaggtg ttggttcata cggacagcag gacggtggct atggaagtta gaatccgcta
10081 aggagtgtgt aacaactcac ctgccgaatg aactagccct gaaaatgaat ggcgctgaag
10141 cgtgttgccg atactcaacc atcagagcaa atgcgaggct ttgatgagta ggagggcgtg
10201 atcgttgcct agaagtattg gcgtgagcct atatggagca gcgattagtg agatcttggt
10261 ggtagtagca aatattcaaa tgagaacttt gaagaccgaa gtggagaagg gttccatgag
10321 aacagcaatt gttcatgggt tactcgatcc taagacatag gttaactcct tgcaatacaa
10381 gaagacattc gttttcgttg tcaaagggga atgaggttaa tattcctcaa gctggacgtg
10441 gtataggcgg taacgcaaag aaacccggaa acgtcagcag gtgtcactgg aagagttatc
10501 ttttcttttt aacatactat ggccatgaaa ttggattatc cagagatatc ggctgtatgt
10561 atggcagagc agctcaccct aagagctgtc agttgcgcgc ctgatgaccc ttgaaaatct
10621 gggggagaca taatttcacg ccagttcgta cccataaccg catcaggtct ccaaggttag
10681 cagcctctgg tccatagaac aatgtagata agggaagtcg gcaaattgga tccgtaactt
10741 cgggataagg attggctctg aggatcgggt ataaaggctt tgtaatgata tccaagcttg
10801 tttgttagtg tggcaacatg ctgatagact tgcgaacgat gaatttgcaa ggtaggtttc
10861 ggccgtcttt atacaattaa cgatcaactc agaactgaag cggacaaagg taatccgact
10921 gtttaataaa aacaaagcat tgtgacggcc tcaacaggtg atgcacacaat gtgatttctg
10981 cccagtgctc tgaatgtcaa agtgacgaca ttcaaccaag cgcgggtaaa cggcgggagt
11041 aactatgact ctctaaatag caatatttac ctttggaggg aaaagttatc aggcatgcac
11101 ctggtagcta gtctttaaac caatagattg catcggttta aaaggcaaga ccgtcaaatt
11161 gcgggaaagg ggtcaacagc cgttcagtac caagtctcag gggaaacttt gagatggcct
11221 tgcaaagggt atggtaataa gctgacggac atggtcctaa ccacgcagcc aagtcctaag
11281 tcaacagatc ttctgttgat atggatgcag ttcacagact aaatgtcggt cggggaagat
11341 gtattcttct cataagatat agtcggacct ctccttaatg ggagctagcg gatgaagtga
11401 tgcaacactg gagccgctgg gaactaattt gtatgcgaaa gtatattgat tagttttgga
11461 gtactcgtaa ggtagccaaa tgcctcgtca tctaattagt gacgcgcatg aatggattaa
11521 tgagattacc actgtcccta tctactatct agcgaaccca cagctaaggg aacgggctta
11581 gaataatcag cggggaaaga agaccctgtt gagcttgact ctagtctaac tttgtgaaat
11641 ggcacgtggg gtatagccta ggtgggagag caatcgatcc tgtaaaacca ctacccacgt
11701 agtcattttg cttatttcgt gaagaaaaga ctggtgcaaa ccagttctaa gattaaggtc
11761 atttattgac tgattttgcg aagacatggt tagggggga gtttgtctgg ggcggaatgc
11821 ctgttaaacc ataacgcagg cgtcctaagt gtagctcagt gagaacggaa atctcacgta
11881 gaacaaaagg gtaaaagcta cattgatttt gattttcagt aggaatacaa accgcgaaag
11941 cgtggcctat cgatccttta actttacaag ttttaagcta gaggtgtcag aaaagttacc
12001 acagggataa ctggcttgtg gcagccaaga gttcatatcg acgttgcttt ttgatccttc
12061 gatgtcggct cttcctatca ttgtgaagca gaattcacac cggtgtcgga ttgttccaccc
12121 gctaataggg aacgtgagct gggcttagac cgtcgtgaga caggttagtt ttaccctact
12181 gatgaaacga tgttgcgaca gtaatttaag ttagtacgag aggaacactt aaatcagata
12241 attggtaaat acggttgtct gaaaagacaa tgccgtgaag ctaccatctg ttggattatg
12301 actgaaggcc tctaagtcag aatccatgct ggaaagcaat gtctaagtgt gatgataaac
12361 gaaaaaaaat aaaaattaag ttcgaaaggt agagcgggga agagcgaaaa agcttgacct
12421 taactgctaa tcgtattcca aattatcatc tacgtaaatc ttttgtagac gacttaacat
12481 ggaacgggta ttgtaagcat gagagtagaa tttctacgat ctgctgagat tcagcccgtc
12541 tccttagatt tatctcatct cccttttattt tttacttctg ctgggggttgt taacctcttt
12601 aagaaatttt ttatgttttg atttgtttaa tttaattttg ttttaactta gtaaatttt
12661 ttccttttttt cactcactgg gttattaaat acttagagat tttacatttt atcaaataat
12721 ttatgaactc attaaaacaa aacaaaacaa agttaaaaaa aactcaatag atttgctaat
12781 aagatgcaaa gcagctatga ggcaattttt ctcatttgga aagcttaagc ttctagagat
12841 cttccatacc taccagttct ccgcctgcag caatggcaac aacgttgccc ggatccgcgg
12901 ccgcggaatt ctcatgtttg acagcttatc atcgatcaat caactgctta taaataaatt
12961 ataaatcaat attaaaaatg ttaaagtttt atgttatttg ttagtaaaaa aattgaatag
13021 ttgtgtttaa gctgatataa gtctttatgc atgatatgtt aaaagttacg cttaaaatta
13081 tgcttttttac gcagaatgag cttagctaaa ttttttctca aagtaaattt tttttaatgc
```

Figure 4D

```
13141 aaaatgaatg aaaaaatttt agtattttat aaaaattctt cattcaaatt ttacccactt
13201 atcaatttat tttttttttgt gactaaagca gtcccagagc ctttctctaa aagttgaatt
13261 ttattaacaa tgccactttt atagaaaatt ttgcatggat ttcctggggc tccaatggaa
13321 aaattgcgaa agtggatttg aatgaaaaag tgaatgtaaa aattaaagta aaatttttgct
13381 ttataaaatg aatgaaaatt taaaacaagc aaaatgaatg aaaaaatctt tgcattttaa
13441 caaaatttttt cattcaaaat ttcacccact tatcaatact tttttttctc cagccgtcaa
13501 agacctatat tgttttccta aaagttgact tttattaaga aacaaaatga atgaaaaaat
13561 ctttgtattt taacaaaatt tttcattcaa aatttcaccc acttatcaat atattttttt
13621 taagtcctgc ctgcaggcta atattctttc ctaaaagttg acttttatta agaagcaaaa
13681 tgaatgaaaa aatctttgta ttttaaccaa attttttcatt caaaatttca cccacttatc
13741 aatatttttt ttgggaccaa accaaaagac ctaaagattt gatttaaaaa gttgactttt
13801 ttcaagaaaa ccactttatt agataaatct ctttttttacc aTggcttgtc caatgaataa
13861 tttgctaaag tggatttgaa taaaattttt ttgcgtgta aaaatgcgct aaactacgct
13921 tagattttaa ctttatccca ctttaatttc aagcgtaaaa ataaaaatcc cacacaaaaa
13981 ttaagtggaa attgatgcaa aaatttcact aaaatttaat tcaataaata tgtaaaaatg
14041 gttTatctct ataatttatg agatttgcat tatttaaggc ttataagaaa tttttaaattt
14101 aacgcggaag cttcatttttt agataaaatt tattaatcat cattaatttc ttgaaaaaca
14161 ttttatttat tgatcttttta taacaaaaaa cccttctaaa agtttatttt tgaatgaaaa
14221 acttataaaa atttatgaaa actacaaaaa ataaaatttt taattaaaat aattttgata
14281 agaacttcaa tctttgacta gcttagtcat ttttgagatt taattaatat ttttatgttta
14341 ttcatatata aactattcaa aatattatag aatttaaaca ttttaacatc ttaatcattg
14401 ataaataacc aaaaatcaaa gtattacatc aataaataac ttttactcaa tgtcaaagaa
14461 attattgggg (SEQ ID NO: 1)
```

*italics primers around the MCS for testing gene insertion - pD5H8F and pD5H8 reverse*

Figure 4E

```
                                                            SEQ ID NO: 14
                                                            SEQ ID NO: 15
                                                            SEQ ID NO: 16

4460         4470         4480         4490         4500         4510         4524
pDSH8  (4460) ATAAGTAAACCCTACCATTTGGAACAACAAAAAGTCGTAACAAGGTATCTGTAGGTGAACCTGCA
pTRA5  (1160) ATAAGTAAACCCTACCATTTGGAACAACAA    AGTCGTAACAAGGTATCTGTAGGTGAACCTGCA
              ATAAGTAAACCCTACCATTTGGAACAACAA    AGTCGTAACAAGGTATCTGTAGGTGAACCTGCA
Consensus (4460) ATAAGTAAACCCTACCATTTGGAACAACAA  AAGTCGTAACAAGGTATCTGTAGGTGAACCTGCA
```

Figure 7

SEQUENCE LISTING

<160> NUMBER OF SEQ ID NOS: 18

<210> SEQ ID NO 1
<211> LENGTH: 14513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | | |
|---|---|---|---|---|---|---|
| ttttaactta | tttttaaaaa | ttaaaccaac | ctctttgttt | atttaaatat | aatttatttt | 60 |
| taattaattc | atttattgat | aatgcataag | tagcatattt | ttaatacatt | attgataatt | 120 |
| ttctgttact | aatagcttgg | ctgcaggtcg | acggatcccc | gggaattcat | cgatatctag | 180 |
| atctcgagct | cgcgaaagct | tggcactggc | cgtcgtttta | caacgtcgtg | actgggaaaa | 240 |
| ccctggcgtt | acccaactta | atcgccttgc | agcacatccc | cctttcgcca | gctggcgtaa | 300 |
| tagcgaagag | gcccgcaccg | atcgcccttc | ccaacagttg | cgcagcctga | atggcgaatg | 360 |
| gcgcctgatg | cggtattttc | tccttacgca | tctgtgcggt | atttcacacc | gcatatggtg | 420 |
| cactctcagt | acaatctgct | ctgatgccgc | atagttaagc | cagccccgac | acccgccaac | 480 |
| acccgctgac | gcgccctgac | gggcttgtct | gctcccggca | tccgcttaca | gacaagctgt | 540 |
| gaccgtctcc | gggagctgca | tgtgtcagag | gttttcaccg | tcatcaccga | aacgcgcgag | 600 |
| acgaaagggc | ctcgtgatac | gcctattttt | ataggttaat | gtcatgataa | taatggtttc | 660 |
| ttagacgtca | ggtggcactt | ttcggggaaa | tgtgcgcgga | acccctattt | gtttattttt | 720 |
| ctaaatacat | tcaaatatgt | atccgctcat | gagacaataa | ccctgataaa | tgcttcaata | 780 |
| atattgaaaa | aggaagagta | tgagtattca | acatttccgt | gtcgccctta | ttcccttttt | 840 |
| tgcggcattt | tgccttcctg | tttttgctca | cccagaaacg | ctggtgaaag | taaaagatgc | 900 |
| tgaagatcag | ttgggtgcac | gagtgggtta | catcgaactg | gatctcaaca | gcggtaagat | 960 |
| ccttgagagt | tttcgccccg | aagaacgttt | tccaatgatg | agcactttta | aagttctgct | 1020 |
| atgtggcgcg | gtattatccc | gtattgacgc | cgggcaagag | caactcggtc | gccgcataca | 1080 |
| ctattctcag | aatgacttgg | ttgagtactc | accagtcaca | gaaaagcatc | ttacggatgg | 1140 |
| catgacagta | agagaattat | gcagtgctgc | cataaccatg | agtgataaca | ctgcggccaa | 1200 |
| cttacttctg | acaacgatcg | gaggaccgaa | ggagctaacc | gcttttttgc | acaacatggg | 1260 |
| ggatcatgta | actcgccttg | atcgttggga | accggagctg | aatgaagcca | taccaaacga | 1320 |
| cgagcgtgac | accacgatgc | ctgtagcaat | ggcaacaacg | ttgcgcaaac | tattaactgg | 1380 |
| cgaactactt | actctagctt | cccggcaaca | attaatagac | tggatggagg | cggataaagt | 1440 |
| tgcaggacca | cttctgcgct | cggcccttcc | ggctggctgg | tttattgctg | ataaatctgg | 1500 |
| agccggtgag | cgtgggtctc | gcggtatcat | tgcagcactg | gggccagatg | gtaagccctc | 1560 |
| ccgtatcgta | gttatctaca | cgacggggag | tcaggcaact | atggatgaac | gaaatagaca | 1620 |
| gatcgctgag | ataggtgcct | cactgattaa | gcattggtaa | ctgtcagacc | aagtttactc | 1680 |
| atatatactt | tagattgatt | taaaacttca | ttttttaattt | aaaaggatct | aggtgaagat | 1740 |
| cctttttgat | aatctcatga | ccaaaatccc | ttaacgtgag | ttttcgttcc | actgagcgtc | 1800 |
| agaccccgta | gaaagatcaa | aggatcttc | ttgagatcct | ttttttctgc | gcgtaatctg | 1860 |
| ctgcttgcaa | acaaaaaaac | caccgctacc | agcggtggtt | tgtttgccgg | atcaagagct | 1920 |
| accaactctt | tttccgaagg | taactggctt | cagcagagcg | cagataccaa | atactgtcct | 1980 |

```
tctagtgtag ccgtagttag gccaccactt caagaactct gtagcaccgc ctacatacct    2040
cgctctgcta atcctgttac cagtggctgc tgccagtggc gataagtcgt gtcttaccgg    2100
gttggactca agacgatagt taccggataa ggcgcagcgg tcgggctgaa cggggggttc    2160
gtgcacacag cccagcttgg agcgaacgac ctacaccgaa ctgagatacc tacagcgtga    2220
gctatgagaa agcgccacgc ttcccgaagg gagaaaggcg acaggtatc cggtaagcgg    2280 cagggtcgga acaggagagc gcacgaggga gcttccaggg ggaaacgcct ggtatcttta    2340
tagtcctgtc gggtttcgcc acctctgact tgagcgtcga ttttgtgat gctcgtcagg    2400 ggggcggagc ctatggaaaa acgccagcaa cgcggccttt ttacggttcc tggccttttg    2460
ctggcctttt gctcacatgt tctttcctgc gttatcccct gattctgtgg ataaccgtat    2520
taccgccttt gagtgagctg ataccgctcg ccgcagccga acgaccgagc gcagcgagtc    2580
agtgagcgag gaagcggaag agcgcccaat acgcaaaccg cctctccccg cgcgttggcc    2640
gattcattaa tgcagctggc acgacaggtt cccgactgg aaagcgggca gtgagcgcaa    2700
cgcaattaat gtgagttagc tcactcatta ggcaccccag gctttacact ttatgcttcc    2760
ggctcgtatg ttgtgtggaa ttgtgagcgg ataacaattt cacacaggaa acagctatga    2820
ccatgattac gccatcgaaa aataatata tcctcccatg tagacctccc ataaaaaact    2880
cagatttcat ttttcaaggt gaatatatga ggcatattca agtatttgat atgaaaaaaa    2940
gtaaaaagtc taagtctcgc taacagcaaa tatgagtttg tttttgcttt gattttaata    3000
aatacaaaat aacaaatatt aaacaaaata gagctgtata ttatgcctaa ccaattaaat    3060
gccatttatt aagcaaaatt atagtgttta aatacaatca tatagttaca aaaatgtttg    3120
aggttagcta gattttgtct agagtactta atctcacttt ccagataagt ctactttaat    3180
aataatttca ttatattaca aacaaacaaa taattataat ttaaatttta atctgaataa    3240
actcgataaa atggaagcaa aaacttccac ttctaatcct tgattttaat tatactatat    3300
tataaatatg aattgaaaaa tctaatgtat gctttaactt atatagatat ataaatatta    3360
tttcttgtaa ttcttataaa cgattgtttt atatatctaa attattatta cttaatatta    3420
atcataatgt ttgatttctg atgcaaacct taacaaaaat ccaacaaata ttttatttaa    3480
aaacaaatgt atttgttcac ttcatatata tgaaaaaata atagaatttc aatactaaat    3540
taaataccaa gataaaattc ttaaattaat ttttttttta tcagttataa aaatagtgtt    3600
tcatgtaaat aaaattaaaa tattttaaa atataaattt aatccaatat tactaactaa    3660
atagataaaa atagttaatt ataaatatat taataagcac tttaagtaaa agaatatttt    3720
tcttttattt tatttaaatt aatttaaaaa taaattcaaa aattatataa tggctttaaa    3780
ttttgataat aaataagaaa gaatatttaa aattataatt ttaataaaat gagaacaaac    3840
aaattaaata ttgtaatttc taatttaatt agattttcaa aataaatgag ttggtttat    3900 ttcaatcaat gattaaattt atattaaaga aagaggttgg tttatttcaa tcaaaaatta    3960
aatttatatt aaagaaagag gttggtttat taatattaaa agcgattttc gaaggtaaaa    4020
ttcaacaaca tagtgctgaa ggctagtttt tttgcttttt gttgttagtt ttatagcctt    4080
cagcactatg ttgttgaatt ttaccttcga aaataactta aaattgagta ataattgggt    4140
ttaaaattta aatttgagta gataagaatt agatgtttat attctgctaa tttcactggt    4200
gaaaatgtag caaatagaaa ttatttaat ctaataaact agcaaatagt atttaaaaca    4260
aaaatatttg ttttttatgt tgtaaaatgt tttaaattag ataaaattta caaatttaca    4320
aattttcaag caaaataggt tctaaaaaat gagaaaatat tacatatttt agctatttga    4380
```

```
ctactttaat gctagtaaat taaaatgaat ttaattcatt ttcactttaa aacacttatt     4440
ttaataaaat atatgatttt aaaatgataa atatttttt aagaggtaaa tttaagaaat      4500
tagttaaatt ttaaagaaaa agcatctaaa atggacaaa aatgaagtat ttccttttt       4560 tatacattta aatgctagaa aatttaagta aaacatttat aaataaaagt aaaatagttt    4620
taggaataag agtaaatagt ttttttatg taaaaaacat tttatcaatt tcatttattc     4680 atttagtta aattttcat tcacaaaaaa cttttttttg gtaaaataaa gactttataa      4740
agataaccta aagaaaagt ttatctagaa ttaaaaatat tgattttgaa aattgctcat      4800
tagatatttt tttggcaaaa aaaaaacaa aaatagtaaa aaatcacttt ttttgagagt     4860
tgaaaaaaag acttagaaaa aattttaaaa gtgtaaaaaa agacttagag aaaaaatcaa   4920
aaagagataa aaagacttag agaaaattta taaattaaaa atgatagaaa agtaaaattt   4980
attttatatt ttttaatcat ttaaatgcta gtaaatttaa ataaaacata tataaaaaaa   5040
cataaaacaa ttttaacaac atgcgtatat catttttat atgtaaaaaaa cattttatca   5100 atttcattta ttcattttag ttaaattta cattcaaaat aattttttt tgattaaata    5160 aagagttata aagagaactt aaagaaaaag tttatctaga attaaaaata ttgattttga  5220
aaattgctca ttagaaattt ttttggcaaa aaaaaaaca aaaatagtaa accttccgaa  5280
cttttgcaac ttttgagact tcgtgaaaaa agacttagaa aaattttga aaatgaaaa    5340 aaaaagactt agagaaaaaa atcaaaaaag tgaaaaaga cttagaaaaa tttttaaaa    5400 tgaaaaaatg atttaggaga aattttgaga ttgcgcttag attttgtgtg aagtcactta 5460
caaaaaatga gcggactcgc tcaaatattt aagtggactc gcataaaat gagtggagtc 5520 actaaaaag ttaagtgaac tcacttaaaa atgagtggag ccactcaaaa aattaagcgg 5580
actcgcttaa tattcgcgga gttaaacaaa aataagtgga ctcacagaaa aattaagcgg 5640
attgcgctaa aaaatgagtg gactcactca aaatgaagc agactcgctt aaaaatgagt 5700
ggagccactc aaaaagttca gcagagccac ttaaaaattt agcttaaaat cagctctaaa 5760
ttaaattaga cttagtgaaa aatagcgaaa atgaaaaaaa tgaaaaatg aatgaaaact  5820 gaaaaattta caagggattg aaaatttttgg cagagtcttt ttttggcaa aaaaaaaaac 5880 aaaaatagta aaccttccga actttttttga ctttgagaaa aattctttgg caaaaaaaat 5940
aaaaataata tcagggggt aaaaatgcat atttaagaag gggaaacatc tccggatcaa 6000
aaataaaata tcagctcgat ttgagcttca gtaagatttc cttttgggca accaaggata 6060
acgataatga agcgctaact gagcagacgt ttttctctat ggcttcggct tttagtcgat 6120
ggccgctgag ggtctgttga aggttttttct ggattaaggc tcgtattaga gcaaatggcc 6180
tgactgaaat tttcatgaag gctgtaaatt cactgcaaag cttcgcagaa acttttccca 6240
gtgacacttg ttgtatcgat atctatgcag atattgttac aaataacgca acacgctagt 6300
actgttataa atcggtgaaa tcgcagatgt tattaacagc tagcaacaaa gttgactaga 6360
gtcgaagaga tgcgatagag ttttctcatt gtgccttcga agattttagc aactagaaga 6420
aactaatagt aaacgaaacg atgcgggatc tatgtataaa gcttaatcta acgatatagc 6480
tgagtactga tctattacaa cgcgtcagtt ctcgatgaac tattaatctt ttgtgaacca 6540
accttttgga acactattca aaaaatgagc aagctgttgg aagatgcaaa tcggaaaata 6600
gcgagcaaat tttgaggata gtaacctggt tgatcctgcc agttacatat gcttgtctta 6660
aatattaacc catgcatgtg ccagttcagt attgaacagc gaaactgcga atggctcatt 6720
aaaacagtta tagtttattt gataattaaa gattacatgg ataaccgagc taattgttgg 6780
```

```
gctaatacat gcttaaaatt ccgtgtcctg cgaccggaac gtatttatta gatattagac    6840
caatcgcagc aatgtgattg agatgaatca agtaactga tcggatcgag gtttacctcg     6900
ataaatcatc taagtttctg ccctatcagc tctcgatggt agtgtattgg actaccatgg    6960
cagtcacggg taacggagaa ttagggttcg attccgaga aggagcctga gaaacggcta     7020
ctacaactac ggttcggcag cagggaagaa aattggccaa tcctaattca gggagccagt    7080
gacaagaaat agcaagctgg gaaacttacg tttctacggc attgaaatga gaacagtgta    7140
aatctcttag cgaggaacaa ttggagggca gtcatggtg ccagcagccg cggtaattcc     7200
agctccaata gcgtatatta agttgttgc agttaaaaag ctcgtagttg aacttctgtt     7260
caggttcatt tcgattcgtc gtgtgaaact ggacatacgt ttgcaaacta aaatcggcct    7320
tcactggttc gacttaggga gtaaacattt tactgtgaaa aaattagagt gttccaggca    7380
ggttttagcc cgaatacatt agcatggaat aatggaatag gactaagtcc atttattgg    7440 ttcttggatt tggtaatgat taataggac agttgggggc attagtattt aatagtcaga    7500
ggtgaaattc ttggatttat taaggactaa ctaatgcgaa agcatttgcc aaagatgttt    7560
tcattaatca agaacgaaag ttaggggatc aaagacgatc agataccgtc gtagtcttaa    7620
ctataaacta taccgactcg ggatcggctg gaataaatgt ccagtcggca ccgtatgaga    7680
aatcaaagtc tttgggttct ggggaagta tggtacgcaa gtctgaaact taaggaatt     7740 gacggaacag cacaccagaa gtggaacctg cggcttaatt tgactcaaca cggggaaact    7800
cacgagcgca agacagagaa gggattgaca gattgagagc tctttcttga ttctttgggt    7860
ggtggtgcat ggccgttctt agttggtgga gtgatttgtc tggttaattc cgttaacgaa    7920
cgagacctta acctgctaac tagtctgctt gtaaataaca ggttgtactt cttagaggga    7980
ctattgtgca ataagccaat ggaagtttaa ggcaataaca ggtctgtgat gcccctagac    8040
gtgctcggcc gcacgcgcgt tacaatgact ggcgcaaaaa gtatttcctg tcctgggaag    8100
gtacgggtaa tcttattaat accagtcgtg ttagggatag ttctttggaa ttgtggatct    8160
tgaacgagga atttctagta agtgcaagtc atcagcttgc gttgattatg tccctgccgt    8220
ttgtacacac cgcccgtcgc ttgtagtaac gaatggtctg gtgaaccttc tggactgcga    8280
cagcaatgtt gcggaaaaat aagtaaaccc taccatttgg aacaacaaga agtcgtaaca    8340
aggtatctgt aggtgaacct gcagatggat cattaacaca attaacaaac cttaacttat    8400
gtactttcga agagaacttc ggttttcttc gaggttttat tgtcacacct agtgtgaata    8460
aaaatttttc atatgtctaa gatctggata acatccaaaa cgaaagaaa actttcaacg     8520 gtggatatct aggttcccgt gacgatgaag aacgcagcga aatgcgatac gcaatgcgaa    8580
ttgcagaacc gcgagtcatc agatctttga acgcaagtgg tggaggtgta aaaccttca    8640 tgtttgtttc agtgtggaaa ggaatcacgc atcttaatgc gattgaagcc gtcaaaagct    8700
tctctcgtta aacgtgatgg gtggtcgagc aatcgccgcc agaacgaagt agtcacattc    8760
cagtaatgtg aacattcgtt caggcatcaa ggcgaatgct cactatgcta ctcatagaaa    8820
aattacattt ttctcactac acctgaaaca agcaagatta cccgctgaac ttaagcatat    8880
cagtaagcgg aggaaaagaa actaactagg atagccccag taatggcgaa tgaacaggct    8940
aaagctcaaa gtgaaaatct gaagtggtca acacaacaga attgtaatct aaagggtcaa    9000
cctgaaacta agctcctctc ataagttcct tgggacagga cgtcaaagag ggtgacaacc    9060
ccgtagtcgg agaggaaggc tggtgtaagg gagatttcaa agagtcgggt tgtttggaat    9120
tgcagcccta agtgggagat aaacttcttc taaagctaaa tatacacggg agaccgatag    9180
```

```
cgaacaagta ctgcgaagga aagatgaaaa gaactttgaa aagagggcta aaagacttga   9240
aaccgttgag aaggaagctg tagaagagca ataaactgga cggcgcataa gggggaagta   9300
ctaatcactg cagagtcgat acgtaaaagg tcgatgagta aggaaatggt acagaacttg   9360
ctacaccggt cagaagacaa aatgggttca gattgaagga gtcacctgag atcgggcagc   9420
aatgcagatc aaaaggaaaa cttcaaactg gactgagggg cctaagggcg attttgtcaa   9480
aatggcttct actgacccgt cttgaaacac ggaccaagga gtctatcaat taagcgagtg   9540
atagggtgga aaaacccgtc cgcgaaacga aagtgagtac aaggtgccaa gccgcaaggt   9600
agcagcatca cccgccttga gtctccgcga agggttcgag gaagagctta attgttagga   9660
cccgaaagat ggtgaactac gcttgaatag ggtgaagcca ggggaaactc tggtggaagc   9720
tcgtagcgat actgacgtgc aaatcgttcg tcaaatttga gtgtagggc gaaagactaa    9780
tcgaaccatc tagtagctgg ttccctccga agtttctctc aggatagcaa gagcaagtac   9840
gcagttttat taggtaaagc gaatgattga aggactcggg agtcctaaga acttcgacct   9900
attctcaaac tttaaattgg taagagccgc ggagtttact taaatgaact ctcgggaaga   9960
acgcagtgct cttgagttgg gccatttttg gtaagcagaa ctggcgatga gggatgaacc  10020
taacgttgag ataaggcgcc caaatgcacg ctcatcagat accacaaaag gtgttggttc  10080
atacggacag caggacggtg gctatggaag ttagaatccg ctaaggagtg tgtaacaact  10140
cacctgccga atgaactagc cctgaaaatg aatggcgctg aagcgtgttg ccgatactca  10200
accatcagag caaatgcgag gctttgatga gtaggagggc gtgatcgttg cctagaagta  10260
ttggcgtgag cctatatgga gcagcgatta gtgagatctt ggtggtagta gcaaatattc  10320
aaatgagaac tttgaagacc gaagtggaga agggttccat gagaacagca attgttcatg  10380
ggttactcga tcctaagaca taggttaact ccttgcaata caagaagaca ttcgttttcg  10440
ttgtcaaaag ggaatgaggt taatattcct caagctggac gtggtatagg cggtaacgca  10500
aagaaacccg gaaacgtcag caggtgtcac tggaagagtt atcttttctt tttaacatac  10560
tatggccatg aaattggatt atccagagat atcggctgta tgtatggcag agcagctcac  10620
cctaagagct gtcagttgcg cgcctgatga cccttgaaaa tctgggggag acataatttc  10680
acgccagttc gtacccataa ccgcatcagg tctccaaggt tagcagcctc tggtccatag  10740
aacaatgtag ataagggaag tcggcaaatt ggatccgtaa cttcgggata aggattggct  10800
ctgaggatcg ggtataaagg cttttgtaatg atatccaagc ttgtttgtta gtgtggcaac  10860
atgctgatag acttgcgaac gatgaatttg caaggtaggt ttcggccgtc tttatacaat  10920
taacgatcaa ctcagaactg aagcggacaa aggtaatccg actgtttaat aaaaacaaag  10980
cattgtgacg gcctcaacag gtgatgacac aatgtgattt ctgcccagtg ctctgaatgt  11040
caaagtgacg caattcaacc aagcgcgggt aaacggcggg agtaactatg actctctaaa  11100
tagcaatatt tacctttgga gggaaaagtt atcaggcatg cacctggtag ctagtctta  11160
aaccaataga ttgcatcggt ttaaaaggca agaccgtcaa attgcgggaa aggggtcaac  11220
agccgttcag taccaagtct caggggaaac tttgagatgg ccttgcaaag ggtatggtaa  11280
taagctgacg gacatggtcc taaccacgca gccaagtcct aagtcaacag atcttctgtt  11340
gatatggatg cagttcacag actaaatgtc ggtcgggaa gatgtattct tctcataaga   11400
tatagtcgga cctctcctta atgggagcta gcggatgaag tgatgcaaca ctggagccgc  11460
tgggaactaa tttgtatgcg aaagtatatt gattagtttt ggagtactcg taaggtagcc  11520
aaatgcctcg tcatctaatt agtgacgcgc atgaatggat taatgagatt accactgtcc  11580
```

```
ctatctacta tctagcgaac ccacagctaa gggaacgggc ttagaataat cagcggggaa    11640
agaagaccct gttgagcttg actctagtct aactttgtga aatggcacgt ggggtatagc    11700
ctaggtggga gagcaatcga tcctgtaaaa ccactaccca cgtagtcatt ttgcttattt    11760
cgtgaagaaa agactggtgc aaaccagttc taagattaag gtcatttatt gactgatttt    11820
gcgaagacat ggttaggggg ggagtttgtc tggggcggaa tgcctgttaa accataacgc    11880
aggcgtccta agtgtagctc agtgagaacg gaaatctcac gtagaacaaa agggtaaaag    11940
ctacattgat tttgattttc agtaggaata caaaccgcga aagcgtggcc tatcgatcct    12000
ttaactttac aagtttttaag ctagaggtgt cagaaaagtt accacaggga taactggctt    12060
gtggcagcca agagttcata tcgacgttgc tttttgatcc ttcgatgtcg gctcttccta    12120
tcattgtgaa gcagaattca caacggtgtc ggattgttca cccgctaata gggaacgtga    12180
gctgggctta daccgtcgtg agacaggtta gttttaccct actgatgaaa cgatgttgcg    12240
acagtaattt aagttagtac gagaggaaca cttaaatcag ataattggta aatacggttg    12300
tctgaaaaga caatgccgtg aagctaccat ctgttggatt atgactgaag gcctctaagt    12360
cagaatccat gctggaaagc aatgtctaag tgtgatgata aacgaaaaaa aataaaaatt    12420
aagttcgaaa ggtagagcgg ggaagagcga aaaagcttga ccttaactgc taatcgtatt    12480
ccaaattatc atctttgta atcttttgta gacgacttaa catggaacgg gtattgtaag    12540
catgagagta gaatttctac gatctgctga gattcagccc gtctccttag atttatctca    12600
tctcccttta tttttactt ctgctggggt tgttaacctc tttaagaaat ttttatgtt    12660 ttgatttgtt taatttaatt ttgtttaact ttagtaaatt ttttccttt tttcactcac    12720 tgggttatta aatacttaga gatttacat tttatcaaat aatttatgaa ctcattaaaa    12780
caaaacaaaa caaagttaaa aaaaactcaa tagatttgct aataagatgc aaagcagcta    12840
tgaggcaatt tttctcattt ggaaagctta agcttctaga gatcttccat acctaccagt    12900
tctccgcctg cagcaatggc aacaacgttg cccggatccg cggccgcgga attctcatgt    12960
ttgacagctt atcatcgatc aatcaactgc ttataaataa attataaatc aatattaaaa    13020
atgttaaagt tttatgttat tgttagtaa aaaaattgaa tagttgtgtt taagctgata    13080
taagtcttta tgcatgatat gttaaaagtt acgcttaaaa ttatgctttt tacgcagaat    13140
gagcttagct aaattttttc tcaaagtaaa ttttttttaa tgcaaaatga atgaaaaaat    13200
tttagtattt tataaaaatt cttcattcaa atttacccca cttatcaatt tattttttt    13260 tgtgactaaa gcagtcccag agcctttctc taaaagttga attttattaa caatgccact    13320
tttatagaaa attttgcatg gatttcctgg ggctccaatg gaaaaattgc gaaagtggat    13380
ttgaatgaaa aagtgaatgt aaaaattaaa gtaaaatttt gctttataaa atgaatgaaa    13440
atttaaaaca agcaaaatga atgaaaaaat ctttgcattt taacaaaatt tttcattcaa    13500
aatttcaccc acttatcaat actttttttt ctccagccgt caaagaccta tattgttttc    13560
ctaaaagttg acttttatta agaaacaaaa tgaatgaaaa atctttgta tttaacaaa    13620 attttcatt caaaatttca cccacttatc aatatatttt ttaagtcc tgcctgcagg    13680 ctaatattct ttcctaaaag ttgactttta ttaagaagca aaatgaatga aaaatcttt    13740 gtattttaac caaattttc attcaaaatt tcacccactt atcaatattt tttttgggac    13800
caaaccaaaa gacctaaaga tttgatttaa aaagttgact ttttcaagaa aaaccacttt    13860
attagataaa tctctttttt accatggctt gtccaatgaa taatttgcta aagtggattt    13920
gaataaaaat tttttttgcgt gtaaaaatgc gctaaactac gcttagattt taactttatc    13980
```

-continued

```
ccactttaat ttcaagcgta aaaataaaaa tcccacacaa aaattaagtg gaaattgatg     14040
caaaaatttc actaaaattt aattcaataa atatgtaaaa atggtttatc tctataattt     14100
atgagatttg cattatttaa ggcttataag aaattttaaa tttaacgcgg aagcttcatt     14160
tttagataaa atttattaat catcattaat ttcttgaaaa acattttatt tattgatctt     14220
ttataacaaa aaaccttct aaaagtttat ttttgaatga aaaacttata aaaatttatg      14280
aaaactacaa aaaataaaat ttttaattaa aataattttg ataagaactt caatctttga    14340
ctagcttagt cattttttgag atttaattaa tattttatgt ttattcatat ataaactatt   14400
caaaatatta tagaatttaa acattttaac atcttaatca ttgataaata accaaaaatc    14460
aaagtattac atcaataaat aactttact caatgtcaaa gaaattattg ggg            14513
```

<210> SEQ ID NO 2
<211> LENGTH: 15
<212> TYPE: DNA
<213> ORGANISM: Unknown
<220> FEATURE:
<223> OTHER INFORMATION: Description of Unknown: Chromosome breakage
      sequence

<400> SEQUENCE: 2
taaaccaacc tcttt                                                     15

<210> SEQ ID NO 3
<211> LENGTH: 15
<212> TYPE: DNA
<213> ORGANISM: Unknown
<220> FEATURE:
<223> OTHER INFORMATION: Description of Unknown: Chromosome breakage
      sequence

<400> SEQUENCE: 3
taaaccaacc tcatt                                                     15

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttaggtacca ccaaaccaaa agacctaa                                       28

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttaggtacct attttcacta agtctaattt aatttag                             37

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 6
ttaggtacca tcttcaaagt atggattaat tatttc                                36

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttaggtaccc tgcattttc cagtaaaaat                                        30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgaagcaga ctcgcttaaa aatg                                             24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atttttgcat caatttccac tta                                              23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttccgttaac gaacgagacc t                                                21

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agataccttg ttacgacttc ttgttgttcc aaatggtag                             39

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

```
cttgaataca atcatgagtt cacc                                          24
```

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gcaattatga attacaacat caaca                                         25
```

<210> SEQ ID NO 14
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
ataagtaaac cctaccattt ggaacaacaa aaagtcgtaa caaggtatct gtaggtgaac   60
ctgca                                                               65
```

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
ataagtaaac cctaccattt ggaacaacaa gaagtcgtaa caaggtatct gtaggtgaac   60
ctgca                                                               65
```

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 16

```
ataagtaaac cctaccattt ggaacaacaa raagtcgtaa caaggtatct gtaggtgaac   60
ctgca                                                               65
```

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
ctaccatttg gaacaacaag aagtcgtaac aaggtatct                          39
```

<210> SEQ ID NO 18
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 18
gactccttca atctgaaccc a                                              21
```

POLYPEPTIDE EXPRESSION IN CILIATES

This application is a Continuation of International Patent Application No. PCT/US2010/28168 filed Mar. 22, 2010, which claims priority to U.S. Provisional Patent Application Ser. No. 61/162,138, filed on Mar. 20, 2009, and U.S. Provisional Patent Application Ser. No. 61/162,142, filed on Mar. 20, 2009, each of which is herein incorporated by reference in its entirety.

SEQUENCE LISTING

The instant application contains a Sequence Listing which has been submitted via EFS-Web and is hereby incorporated by reference in its entirety. Said ASCII copy, created on Jul. 15, 2013, is named 2202970.133US2_SL.txt and is 23,485 bytes in size.

FIELD OF THE INVENTION

The invention relates to recombinant polypeptide production and, in particular, methods and compositions for the production of recombinant polypeptides in ciliates.

BACKGROUND OF THE INVENTION

The production of polypeptides derived from natural sources can be limited by the expense of purification or suffer from limits on availability of starting materials. Heterologous polypeptide production is an alternative to the recovery of polypeptides from natural sources and can be used for the production of polypeptides in economically relevant amounts that are suitable for a variety of applications. Exemplary polypeptides suitable for production in heterologous expression systems include, but are not limited to, antibodies, hormones, cytokines, interleukins, enzymes, blood factors, pesticides and vaccines. Production of genetically engineered vaccine antigens, therapeutic polypeptides, industrial enzymes, biopolymers, and bioremediation agents constitute a multibillion dollar-per-year industry.

Current in vivo platforms for the production of recombinant polypeptides are limited to a relatively small number of cell-based systems that employ bacteria, fungi, insect and mammalian cells. Although bacteria can offer high yield and low-cost alternatives for production of mammalian polypeptides, cell culture systems based on higher organisms (e.g., insect or mammalian cells) generally provide polypeptides having greater fidelity to the natural polypeptides in terms of polypeptide folding and/or post-translational processing (e.g., glycosylation). Whole transgenic plants and animals have also been harnessed for the production of recombinant polypeptides, but the long development time from gene to final product can be a major drawback with these multicellular organisms, purification of the recombinant polypeptides can be difficult, and yield may be low.

Recombinant gene expression in microbial systems generally relies on one of two methods for expression construct maintenance in the host cell: episomal or integrative-based expression. Episomal expression vectors can contain the genetic elements required for recombinant gene expression (i.e., promoters, terminators, etc.) and can be maintained as independent genetic elements, usually based on a dominant drug selection system, or with a recessive auxotrophic selection system. Removal of the selection system often results in loss of the transgenic expression element as cell culture routinely confers a competitive growth advantage to cells that have lost recombinant DNA constructs. Integrative expression vectors can be more genetically stable than episomal expression vectors since they are generally maintained at specific loci in a host cell's chromosomes. This latter approach, however, can suffer from limited copy numbers of the transgenes compared to episomal strategies.

Recombinant gene expression in ciliated protists is facilitated via a variety of available expression vectors encompassing all the machinery required for transgene expression. These vectors can be incorporated as either episomal or integrative genetic elements. For example, traditional methods for the production of transgene-encoded polypeptides in ciliates such as Tetrahymena have been based on incorporation of expression cassettes into somatic loci on the macronuclear chromosomes. Although some recombinant gene expression methods employed in Tetrahymena take advantage of the high-level amplification of ribosomal DNA copy number that occurs following sexual conjugation, current methods can result in the formation of a recombinant palindrome over several generations of propagation. This can result in loss of the transgene and, consequently, in loss of expression of any polypeptides encoded by the transgene.

Increasing yield and maintaining genetic stability is important in expression system for many reasons including, but not limited to, reduced production costs. Thus, there is a need for improved methods for recombinant polypeptide production in ciliates. This invention addresses this need.

SUMMARY OF THE INVENTION

In one aspect, the invention realtes to a nucleic acid construct comprising: (a) a selection cassette encoding a resistance marker, (b) a transgene cassette encoding a recombinant polypeptide, and (c) a C3 allele rDNA locus comprising a 17S rDNA gene that does not confer paromomycin resistance to a ciliate transformed with the nucleic acid construct.

In some embodiments, the construct is a linear DNA or RNA. In other embodiments, the construct is a circular DNA or RNA.

In some embodiments, the selection cassette does not confer paromomycin resistance to a ciliate transformed with the nucleic acid construct.

In some embodiments, the 17S rDNA gene is a B allele 17S rRNA.

In some embodiments, the construct is a vector, a plasmid, a cosmid, a chromosome or minichromosome, a transposon, an rDNA or any combination thereof.

In some embodiments, the vector is an rDNA vector. In certain embodiments, the vector is an rDNA rescue vector.

In another aspect, the invention relates to a method for producing a recombinant polypeptide in a ciliate, the method comprising: (a) transforming the ciliate with an rDNA vector as described herein, (b) culturing the ciliate and expressing the recombinant polypeptide; and (c) isolating the recombinant polypeptide.

In another aspect, the invention relates to a genetically modified ciliate having a micronuclear genotype having a micronuclear rDNA locus comprising one or more non-functional rDNA genes. In some embodiments, the non-functional micronuclear rDNA locus of the genetically modified ciliate comprises a modification of the nucleotide sequence of the micronuclear rDNA locus. In some embodiments, the modification of the micronuclear rDNA locus results in the formation of a non-functional rDNA chromosome after sexual conjugation of the ciliate. In some embodiments, the genetically modified ciliate has a conditionally conjugation-lethal phenotype. In certain embodiments, the rDNA gene is selected from the group consisting of the 5.8S, 17S or 26S genes. In some embodiments, the modification is selected from the group consisting of a deletion, an insertion, a substitution or an inversion.

In another aspect, the invention relates to a method for producing a recombinant polypeptide in a ciliate, the method comprising: (a) causing the genetically modified ciliate to undergo sexual reproduction by conjugation; (b) transforming a genetically modified ciliate having a conditionally conjugation-lethal phenotype as described herein, with an rDNA rescue vector comprising a transgene cassette encoding the recombinant polypeptide; (c) culturing the genetically modified ciliate to produce the recombinant polypeptide; and (d) isolating the recombinant polypeptide.

BRIEF DESCRIPTION OF THE FIGURES

FIG. 2.

FIG. 4. Sequence of the pD5H8 vector (SEQ ID NO: 1) (14,513 bp). The rDNA gene sequences are located between positions 200-10683 in the sequence as shown. The 3' rDNA flanking sequence is shown at positions 10684 to 10815. The 3' and 5' 15 base pair CBS regions are shown between nucleotides 10704 to 10718 and nucleotides 39 to 53, respectively. The pIC19 vector is shown at between nucleotides 11235-13560. The 17S rDNA is located between positions 2784-4536. The capital A at position 4490 is a mutation in 17s conferring Pm resistance. The 5.8S rDNA is located between positions 4665-4825. The 26S rDNA is located between positions 5041-8763. The NotI site at position 9108 is a unique restriction enzyme site contained in a short multi-cloning site (derived from pHSS6) in the 3' non-translated sequence of the 26S rDNA locus. Bases corresponding to known differences in the C3 rDNA polymorph (as found in pD5H8) and the B rDNA polymorph (as found in host cells) include an adenine substitution at position 269, an adenine substitution at position 783, an adenine substitution at position 1213, a 42 base pair insertion at position 1428, an adenine insertion after position 1524, a thymine substitution at position 1551, a thymine substitution at position 1609, a thymine substitution at position 10049, and a thymine substitution at position 10251. Of these, the most significant is the 42 base pair insertion at position 1428, and is related to the replicative advantage of C3 rDNA polymorphs over B rDNA polymorphs.

FIG. 7. Alignment of pD5H8 and pTRAS vector 17S rDNA gene. An alignment of pTRAS and pD5H8 highlights the A4490G mutation that confers paromomycin resistance to pD5H8 (A4490) and paromomycin sensitivity to pTRAS (G4490).

DETAILED DESCRIPTION OF THE INVENTION

Figure 1:
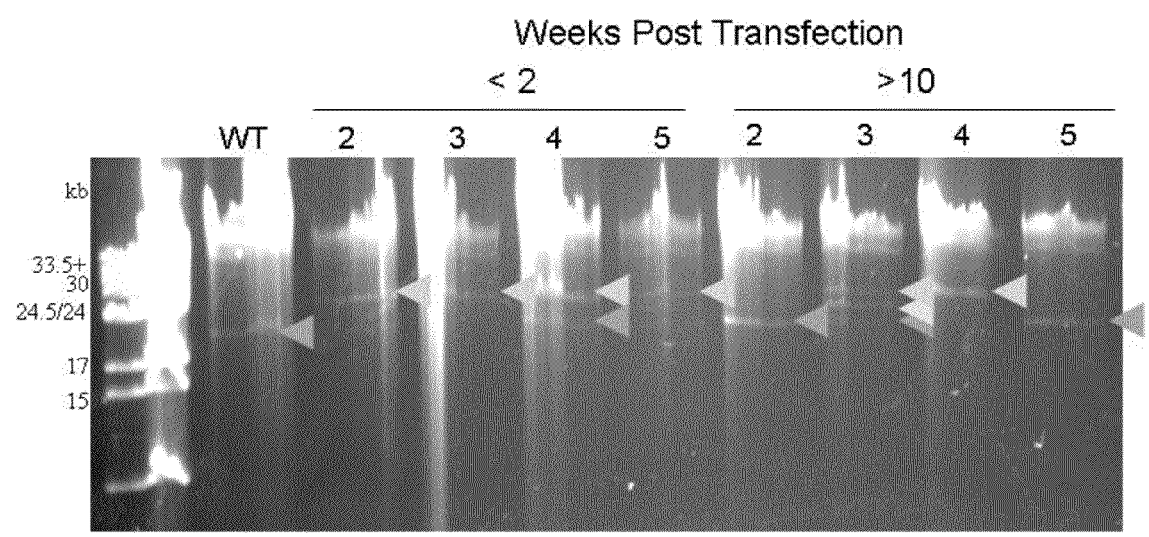
FIG. 1. Variable rDNA molecules in transformed cells. Recombinant rDNA chromosomes of transgenic *Tetrahymena thermophila* strains are unstable over time. Genomic DNA was isolated from wild-type (CU428) and four independent rDNA transgenic clones (2, 3, 4 and 5) less than two weeks and again after more than 10 weeks following initial selection. During the intervening time, strains were passaged into fresh media. Equivalent amounts of nucleic acid were resolved by agarose gel electrophoresis and rDNA chromosomes visualized by ethidium bromide staining. Three forms of rDNA chromosome were detected: wild-type rDNA (bottom arrow), hybrid rDNA (middle arrow) and fully transgenic rDNA (top arrow). Over time, transgenic clones 2, 3 and 5 all show a shift from abundant fully transgenic rDNA species to only wild-type rDNA (Clones 2 and 5) or a mixture of wild-type, hybrid and fully transgenic (Clone 3). Clone 4 shifts from a mixture of hybrid and fully transgenic rDNA to fully transgenic rDNA.

All publications, patent applications, patents, and other references mentioned herein are hereby incorporated by reference in their entirety. The patent, scientific and technical literature referred to herein establish knowledge that was available to those skilled in the art at the time of filing. The entire disclosures of the issued U.S. patents, published and pending patent applications, and other publications that are cited herein are hereby incorporated by reference to the same extent as if each was specifically and individually indicated to be incorporated by reference. In the case of any inconsistencies, the present disclosure will prevail.

DEFINITIONS

All scientific and technical terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "ciliate" means a eukaryote belonging to the kingdom, Chromalveolata, the superphylum, Alveolata, and the phylum, Ciliophora. Ciliates, as used herein, are complex protozoa characterized by the presence of cilia on their cell surfaces and dimorphic nuclei consisting of a macronucleus and one or more micronuclei.

As used herein, "*Tetrahymena* spp." refers to ciliate protozoa in the family of Tetrahymenidae. Exemplary *Tetrahymena* spp. include but are not limited to, the species *T. Thermophila* and *T. pyriformis*.

A used herein, the term "rDNA locus" refers to a ciliate gene encoding one or more copies of a 5.8S rRNA, 17S rRNA or 26S rRNA that is capable of being processed into a minichromosome upon conjugative replication. As used herein, the term rDNA locus can refer to a nucleotide sequence encoding any variant, isoform, homolog or mutant rDNA known in the art, for example, naturally occurring polymorphisms between B and C3 rDNA. As used herein, an rDNA locus can be comprised within any nucleotide sequence, including, but not limited to a micronuclear genome or an artificial nucleic acid construct (e.g., an rDNA vector).

As used herein, the term "non-functional rDNA gene" refers to an rDNA gene that does not produce a sufficient amount of the encoded rRNA or to an rDNA gene that is mutated and/or modified such that the encoded rRNA is not capable of performing the normal biological activity of the corresponding wild-type rRNA gene, thereby resulting in a ciliate with a conditionally conjugation-lethal phenotype.

As used herein, the term "non-functional micronuclear rDNA locus" refers to an rDNA locus, having one or more non-functional rDNA genes.

As used herein, the term "conditionally conjugation-lethal" refers to a phenotype wherein sexual conjugation by the ciliate (e.g., *Tetrahymena* spp.) results in lethality. A condition of conjugation-lethality can arise from, but is not limited to, genetic modifications of the micronuclear genome (e.g., deletion of one or more rDNA encoding genes in the micronuclear rDNA locus).

As used herein, the term "recombinant" means, with respect to two or more genetic or polypeptide sequences, that the sequences do not occur in the same physical relation to each other in nature and/or do not naturally occur within the same genome or polypeptide. For example, a genetic construct may include a coding sequence which is operably joined to one or more regulatory sequences, or to one or more other coding sequences, and these sequences are considered heterologous to each other if they are not operably joined in nature and/or they are not found in the same relation in a genome in nature. Similarly, a polypeptide may include a first polypeptide sequence which is joined by a standard peptide bond to a second polypeptide sequence, and these sequences are considered heterologous to each other if they are not found in the same relation in any polypeptide or proteome in nature.

As used herein, the term "nucleotide sequence" means any molecule comprising a sequence of covalently joined nucleoside-like chemical units which has selective binding affinity for a naturally-occurring nucleic acid of complementary or substantially complementary sequence under appropriate conditions (e.g., pH, temperature, solvent, ionic strength, electric field strength). Nucleotide sequences include naturally-occurring nucleic acids as well as nucleic acid analogues with modified nucleosides or internucleoside linkages, and molecules which have been modified with linkers or detectable labels which facilitate immobilization on a substrate or which facilitate detection.

As used herein, the term "promoter" means a nucleotide sequence which is capable of binding RNA polymerase and initiating transcription of a downstream or 3' coding sequence.

As used herein, the term "reporter gene" means any genetic sequence which, when expressed, has a biochemical or phenotypic effect which is detectable.

As used herein, the term "selectable marker" means any genetic sequence which, when expressed, has a biochemical or phenotypic effect which is dominant and selectable by the presence or absence of a selection agent. Selectable marker genes that confer resistance or tolerance to a normally toxic selection agent cause only successfully transfected cells to survive in the presence of the selection agent and are referred to as positive selectable markers. Examples of positive selectable marker genes and their corresponding selection agents are: aminoglycoside phosphotransferase (APH) and G418; dihydrofolate reductase (DHFR) and methotrexate (Mtx); hygromycin-B-phosphotransferase (HPH) and hygromycin-B; xanthine-guanine phosphoribosyltransferase (XGPRT) and mycophenolic acid; and adenosine deaminase (ADA) and 9-β-D-xylofuranosyl adenine (Xyl-A). In another example of a positive selectable marker system, thymidine kinase (TK) and aminopterin (included, e.g., in hypoxanthine-aminopterin-thymidine (HAT) medium) can be used in cells that are initially thymidine kinase deficient (tk⁻). The aminopterin will normally kill tk⁻ cells and, therefore, only successful TK transfectants will survive. Another positive selectable marker system is AmpR and ampicillin. Selectable marker genes that confer sensitivity or susceptibility to a normally non-toxic selection agent cause only successfully transfected cells to die in the presence of the selection agent are referred to as negative selectable markers. Examples of negative selectable marker genes and their corresponding selection agents include: thymidine kinase (TK) and gancyclovir. Phenotypic selectable marker genes permit selection based upon morphological or biochemical traits rather than cell death or survival. In some cases, the phenotypic marker is detectable only in the presence of an additional selection agent. An example of a phenotypic selectable marker gene and its additional selection agent is β-galactosidase (lacZ) and X-gal.

As used herein with respect to polypeptide preparations, the term "substantially pure" means a preparation which contains at least 60% (by dry weight) the polypeptide of interest, exclusive of the weight of other intentionally included compounds. In some embodiments, the preparation is at least 75%, at least 90%, or at least 99%, by dry weight the polypeptide of interest, exclusive of the weight of other intentionally included compounds. Purity can be measured by any appropriate method, e.g., column chromatography, gel electrophoresis, or HPLC analysis. If a preparation intentionally includes two or more different polypeptides of the invention, a "substantially pure" preparation means a preparation in which the total dry weight of the polypeptides of the invention is at least 60% of the total dry weight, exclusive of the weight of other intentionally included compounds. For such preparations containing two or more polypeptides of the invention, the total weight of the polypeptides of the invention can be at least 75%, at least 90%, or at least 99%, of the total dry weight of the preparation, exclusive of the weight of other intentionally included compounds. Thus, if the polypeptides of the invention are mixed with one or more other polypeptides (e.g., serum albumin) or compounds (e.g., diluents, detergents, excipients, salts, polysaccharides, sugars, lipids) for purposes of administration, stability, storage, and the like, the weight of such other polypeptides or compounds is ignored in the calculation of the purity of the preparation.

As used herein, the term "transform" means to introduce into a cell an exogenous nucleic acid or nucleic acid analog which replicates within that cell, that encodes a polypeptide sequence which is expressed in that cell (with or without integration into the genome of the cell), and/or that is integrated into the genome of that cell so as to affect the expression of a genetic locus within the genome. The term "transform" is used to embrace all of the various methods of introducing such nucleic acids or nucleic acid analogs, including, but not limited to the methods referred to in the art as transformation, transfection, transduction, or gene transfer, and including techniques such as microinjection, DEAE-dextran-mediated endocytosis, calcium phosphate coprecipitation, electroporation, liposome-mediated transfection, ballistic injection, viral-mediated transfection, and the like.

As used herein, the term "vector" means any genetic construct, such as a plasmid, phage, transposon, cosmid, chromosome, virus, virion, etc., that is capable transferring nucleic acids between cells. Vectors may be capable of one or more of replication, expression, and insertion or integration, but need not possess each of these capabilities. Thus, the term includes cloning, expression, homologous recombination, and knock-out vectors.

As used herein, the terms "increase" and "decrease" mean, respectively, to cause an increase or decrease of at least 5%, as determined by a method and sample size that achieves statistically significance (i.e., p<0.1).

As used herein, the term "statistically significant" means having a probability of less than 10% under the relevant null hypothesis (i.e., p<0.1).

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, ..., 0.9, 0.99, 0.999, or any other real values $\geq 0$ and $\geq 2$, if the variable is inherently continuous.

The term "about" is used herein to mean approximately, in the region of, roughly, or around. When the term "about" is used in conjunction with a numerical range, it modifies that range by extending the boundaries above and below the numerical values set forth. The term "about" is used herein to modify a numerical value above and below the stated value by a variance of 20%.

As used herein, unless specifically indicated otherwise, the word "or" is used in the inclusive sense of "and/or" and not the exclusive sense of "either/or."

As used herein and in the appended claims, the use of singular forms of words, and the use of the singular articles "a," "an" and "the," are intended to include and not exclude the use of a plurality of the referenced term unless the content clearly dictates otherwise.

In general, the compositions, genetically modified ciliates and methods described herein are useful for the production of one or more polypeptides of interest. Existing ciliate-based expression systems, employing the ciliate *T. thermophila*, enable high level amplification of transgenes encoding polypeptides of interest, but suffer from genetic instability resulting a in loss of transgenes and thus loss of expression and yield of the desired polypeptide.

In one aspect, the system described herein enables high level amplification of a transgene encoding a polypeptide of interest in genetically-modified ciliates.

In one aspect, the methods and compositions described herein provide a polypeptide expression system that enables stable expression of transgenes for the production of eukaryotic or prokaryotic polypeptides in ciliates.

In another aspect, the recombinant polypeptide expression system of the invention comprises a genetically modified ciliate having a non-functional micronuclear rDNA locus (e.g., a universal recipient line as described below) and wherein the non-functional micronuclear rDNA locus causes the ciliate to exhibit a conditionally conjugation-lethal phenotype. In some embodiments, the micronuclear rRNA locus is non-functional due to a deletion, mutation or substitution in one or more regulatory regions that regulate the expression, replication, amplification or stability of the micronuclear nucleic acid encoding the rRNA.

In one aspect, a universal recipient line is provided which comprises a genetically modified ciliate having a non-functional micronuclear rDNA locus. In some embodiments, the non-functional rRNA locus is the 5.8S rRNA locus. In other embodiments, the non-functional rRNA locus is the 17S rRNA locus. In still other embodiments the non-functional rRNA locus is the 26S rRNA locus. In other embodiments, the non-functional rRNA locus is the any other rRNA locus which, when non-functional, results in a conditionally conjugation-lethal phenotype. Defined mutations that inactivate such rRNA loci are also known in the art. For example, the rmm10 mutation is a recessive-lethal and cis-acting maturation mutant that results in severely defective production of both monomeric and palindromic rDNA in the developing macronucleus (Kapler et al. (1994a)). Naturally occurring polymorphisms between the B and C3 alleles are also known in the art. In some embodiments, genetically modified ciliates have at least one nonfunctional micronuclear rRNA gene. In other embodiments, the genetically modified ciliates can have at least two nonfunctional micronuclear rRNA genes. In other embodiments, the genetically modified ciliates can have at least three nonfunctional micronuclear rRNA genes. In some embodiments, the micronuclear rRNA locus is non-functional due to a deletion, mutation or substitution in the micronuclear nucleic acid encoding the rRNA. Methods to render a micronuclear rRNA non-functional are well known in the art and can include, without limitation, deletion and/or mutation of the gene. Additional methods, including mutation or deletion of elements regulating transcription and/or stability of the rRNA, can also be used in conjunction with the methods described herein.

In still other embodiments, the micronuclear rRNA locus is non-functional due a deletion, mutation, inversion or substitution in a regulatory region regulating the expression of a 5.8S rRNA, 17S rRNA, 26S rRNA or other rRNA from a macronuclear chromosome generated from a micronuclear rDNA locus during upon macronuclear reorganization.

In still other embodiments, the micronuclear rRNA locus is non-functional due to a deletion, mutation, inversion or substitution of a sequence regulating the amplification or stability of a macronuclear chromosome generated from a micronuclear rDNA locus during upon macronuclear reorganization. In some embodiments, the deletion, mutation, inversion or substitution is in a micronuclear sequence that regulates the formation of a telomere of the rDNA macronuclear chromosome. In other embodiments, the deletion, mutation, inversion or substitution is in a micronuclear sequence that regulates replication of the rDNA macronuclear chromosome.

In certain aspects, ciliates transformed with the rDNA vectors described herein can be utilized as hosts for recombinant polypeptide expression. Accordingly, in certain aspects, the transformed ciliates can be used as production cell lines suitable for use as hosts for recombinant polypeptide expression by transformation of the ciliate with an rDNA vector comprising a transgene expression cassette capable of directing expression of the transgene.

In certain aspects, the genetically modified ciliates having a non-functional micronuclear rDNA locus described herein can be utilized as hosts for recombinant polypeptide expression. Accordingly, in certain aspects, genetically modified ciliates (e.g., *Tetrahymena* spp.) having a non-functional micronuclear rDNA locus (e.g., universal recipient lines) can be converted to production cell lines suitable for use as a host for recombinant polypeptide expression. In some embodiments, a universal recipient line can be rendered conjugation competent by transformation of the hosts with an rDNA rescue vector. In some embodiments, the rDNA rescue vector can further comprise a transgene expression cassette capable of directing expression of the transgene.

Thus, in other aspects, the invention described herein relates to rDNA vectors. In some embodiments, the rDNA vector comprises a complete copy of an rDNA locus. In certain embodiments, the rDNA locus in the rDNA vector is a C3 rDNA allele. In other embodiments, the rDNA locus in the rDNA vector is a C3 rDNA allele genetically modified to include a B allele 17S rDNA gene in place of a C3 allele 17S rDNA gene. In other embodiments, the rDNA locus in the rDNA vector is a C3 rDNA allele that is conditionally conjugation-lethal in genetically modified ciliates comprising a non-functional micronuclear rDNA locus.

In some embodiments, the rDNA vector described herein comprises a complete copy of a micronuclear rDNA locus flanked by functional chromosome breakage sequences (CBSs) on the 3' end and the 5' end of the rDNA locus such that transformation of a ciliate that is undergoing, or will undergo, macronuclear reorganization will cause the rDNA vector to be processed into a macronuclear chromosome (e.g., a minichromosome). In further embodiments, the rDNA vector can further comprise one or more cis-acting nucleotide sequences that promote amplification of a minichromosome derived from the rDNA vector during macronuclear differentiation.

In another aspect, a conditionally conjugation-lethal ciliate can be rendered capable of surviving conjugation by transforming the ciliate with an rDNA rescue vector comprising one or more sequences corresponding to a functional rDNA locus. The conditionally conjugation-lethal ciliate includes a genetically-modified micronuclear rDNA locus that is not capable of producing a macronuclear rDNA chromosome capable of expressing a sufficient amount of one or more types of rDNA so as to permit survival of progeny upon conjugative reproduction of the ciliate (e.g., because one or more rDNA coding sequences is missing from the micronuclear rDNA locus, or because one or more regulatory regions regulating the expression of an rRNA is missing or non-functional in the micronuclear genome, or because one or more regulatory regions regulating the formation of a macronuclear rDNA chromosome is missing or non-functional in the micronuclear genome).

In some embodiments, the absence of a functional micronuclear rDNA locus in the micronucleus can be achieved by partial or complete deletion or mutation of the corresponding nucleotide sequences in the micronuclear rDNA. Mutations are understood to mean, for example, insertions, deletions, inversions or merely substitution of individual base pairs.

Gene deletions or mutations can be introduced to the target organism by methods known to one skilled in the art, including known methods for introducing somatic and germline mutations in *Tetrahymena* spp. (e.g., Bruns et al. (2000) and Cassidy-Hanley et al. (1997)). Additional exemplary methods suitable for use with the methods are described in, for example, Sambrook et al., *Molecular Cloning, A Laboratory Manual*, Cold Spring Harbor, N.Y. Such genetically modified ciliates can be rendered conjugation-competent by transformation with an rDNA rescue vector.

In another aspect, the invention provides an rDNA rescue vector capable of rescuing the conditionally conjugation-lethal phenotype of the genetically modified ciliate, wherein the conditional conjugation-lethal phenotype of the ciliate is due to a non-functional rDNA locus in the micronucleus, by transforming the ciliate with a rescue vector.

In some embodiments, the rDNA rescue vector comprises all or part of a functional rDNA locus. In some embodiments, the rDNA rescue vector can render conditionally conjugation-lethal genetically modified ciliates capable of surviving conjugation by forming a recombinant macronuclear rDNA chromosome. In another embodiment, the rDNA rescue vector can render conditionally conjugation-lethal genetically modified ciliates capable of surviving conjugation by integrating into the micronuclear genome such that a functional macronuclear rDNA chromosome is generated upon conjugative reproduction of the ciliate.

In further embodiments, a transgene, optionally encoding a polypeptide of interest can be incorporated in the rDNA vector or rDNA rescue vector such that a ciliate transformed with the rDNA vector or rDNA rescue vector described herein, will express a polypeptide encoded by the transgene. In some such embodiments, the rDNA vector or rDNA rescue vector can further comprise one or more operably linked regulatory nucleotide sequences that direct the expression of the transgene in the ciliate.

In yet another aspect, the invention relates to methods useful for the production of a recombinant polypeptide in a ciliate, the methods comprising (a) transforming a ciliate with an rDNA vector, wherein the vector further comprises a nucleotide sequence encoding the recombinant polypeptide; (b) culturing the ciliate to produce the recombinant polypeptide; and (c) isolating the recombinant polypeptide.

In some embodiments, a transgene, optionally encoding a polypeptide of interest can be incorporated in an rDNA rescue vector such that conditionally the rescued conjugation-lethal genetically modified ciliates will also comprise the transgene. Accordingly, the rDNA vector or the rDNA rescue vector can further comprise operationally linked regulatory nucleotide sequences that direct the expression of the transgene in the ciliate.

Also described herein are methods and compositions useful for the expression of a recombinant polypeptide in a ciliate.

A transgene cassette encoding a recombinant polypeptide that is to be expressed in the cell can also be included within the rDNA vector or the rDNA rescue vector. Thus, in some embodiments, the rDNA vector or the rDNA rescue vector can be an expression vector for expression of recombinant polypeptides in a ciliate. An expression vector, according to the invention, can be a nucleic acid molecule, like DNA or RNA, circular or linear, for example, a plasmid, a cosmid or an artificial chromosome, that allows expression of the recombinant gene in the host cell. Such expression vectors can be present episomally in the cell, can be integrated in the micronuclear genome, can be integrated in the macronuclear genome, or can be self-replicating.

In some embodiments, expression of the recombinant polypeptide can be achieved by transforming a ciliate having a homozygous B rDNA micronuclear genotype with an rDNA vector capable of generating a C3 allelic rDNA minichromosome upon macronuclear reorganization.

In some embodiments, the rDNA vector or the rDNA rescue vector can comprise a selection marker that does not confer resistance to growth in a medium containing paromomycin.

For example, the rDNA vector or the rDNA rescue vector as described herein can include one or more selection cassettes encoding a selection marker. The selection marker can enable selection of cells that have resistance to various biostatic or biocidal drugs upon transformation with the vector. In some embodiments, the rDNA vector or the rDNA rescue vector can comprise a selection cassette such that transformants can be selected against non-transformants by culturing them in media comprising a selection agent.

Methods for selection of transformed cells harboring heterologous genes are known in the art. For example, the vector can further comprise a selectable cassette marker to permit selection for transformed cells (e.g., a cycloheximide resistant cassette) (Gaertig et al. (1994), *Nucleic Acids Res.* 22:5391-5398). Selection of transformants can be achieved by growing the cultured ciliates in a medium which allows only the transformants to survive. Suitable selection agents include antibiotics which will kill all or most non-transformants but allow transformants (which also possess an antibiotic resistance gene) to survive. A number of antibiotic-resistance markers are known in the art. Any known antibiotic-resistance marker can be used to transform and select transformed host cells in accordance with the present invention.

The methods described herein also relate to methods for expressing a transgene in genetically modified ciliates. In embodiments, ex-conjugants transformed with the rDNA rescue vector comprising the transgene will have a macronuclear rDNA chromosome encoding all rRNAs necessary for survival of the ciliate in addition to a transgene cassette capable of driving expression of a heterologous polypeptide encoded by the transgene.

In yet another aspect, the invention relates to methods useful for the production of a recombinant polypeptide in a genetically modified conditionally conjugation-lethal ciliate, the methods comprising (a) causing the genetically modified ciliate to undergo sexual reproduction by conjugation; (b) transforming the genetically modified ciliate with a vector capable of suppressing the conditionally lethal phenotype of the genetically modified ciliate, wherein the vector further comprises a nucleotide sequence encoding the recombinant polypeptide; (c) culturing the genetically modified ciliate to produce the recombinant polypeptide; and (d) isolating the recombinant polypeptide.

Without being bound by theory, transformation of a conditionally conjugation-lethal ciliate with an rDNA rescue vector comprising a functional rDNA locus can result in the introduction of a complete functional rDNA and subsequent processing of said rDNA to a functional macronuclear palindromic chromosome which will replace the non-functional micronuclear version and render the transformed cell viable. In some embodiments, the progeny of such transformed cells will have a non-functional micronuclear rDNA locus but a fully functional, vector-derived recombinant rDNA chromosome in the macronucleus. In some embodiments, a transgene, optionally encoding a polypeptide of interest, can be incorporated in the rDNA rescue vector such that the conditionally conjugation-lethal ciliates that are rescued will also comprise the transgene. Optionally, the rDNA rescue vector can further comprise operationally linked regulatory nucleotide sequences that direct the expression of the transgene in the ciliate.

The methods disclosed herein also enable selection of transformed cells without the addition of an antibiotic or any additional selection marker to the growth medium after the conditionally conjugation-lethal genetically modified ciliates described herein have been rescued by transformation with an rDNA rescue vector. In some embodiments, the parental strain (e.g., conditionally conjugation-lethal genetically modified ciliates having a non-functional micronuclear rDNA) can further comprise a selection marker such that parental strains can be grown under selective pressure. Such genetically modified parental lines can be rendered conjugation-competent by rescue with an rDNA rescue vector. In some embodiments, such parent mating lines are homozygous functional heterokaryons for a non-functional micronuclear rDNA locus and at least one of the parent lines is a functional heterokaryon for a selectable marker. Because only progeny transformed with the rDNA rescue vector and expressing the selectable marker will survive, there is no further need for selection of ex-conjugants in subsequent cultures after the parents have been eliminated.

In some embodiments, the rescue vector can further comprise a second selection marker such that ex-conjugants of a parental mating can be selected against non-conjugating parental cells by culturing them in media comprising the second selection marker. For example, in the case of genetically modified ciliates having a non-functional micronuclear rDNA locus, a second selectable marker may be useful during the mating step to eliminate non-mating parents and enable isolation of progeny from the mating of two parent lines. The second selection agent can be withdrawn from the growth medium shortly after the mating step because the selection marker will eliminate non-mating parental cell and only those cells successfully transformed with the rescue vector will be capable of surviving in the vegetative state. Thus, in one aspect, the methods described herein allow for the use one or more antibiotic agents, including antibiotic agents toxic to humans, because the use of such antibiotic agents can be limited to a defined period after transformation suitable to eliminate non-transformed and non-mating parent cells. Because the antibiotic agent can be used to eliminate non-transformed and non-mating parent cells, transformed ex-conjugants can subsequently be cultured in a medium lacking an antibiotic selection agent. Accordingly, the antibiotic agents can be diluted or washed away prior to isolation of a recombinant polypeptide expressed from ex-conjugants harboring a transgene.

Ciliates Useful in the Invention

The invention may be practiced with a variety of different ciliates. A ciliate as described herein can be any free-living ciliate characterized by dimorphic nuclei consisting of a macronucleus and one or more micronuclei, including but not limited to *Tetrahymena, Paramecium, Blepharisma, Colpidium, Euplotes, Stylonichia* and *Oxytricha* species.

The free-living ciliate protists are a large and diverse phylum (Ciliata) whose members display a structural and functional complexity comparable to that of higher metazoa (Fankel (2000); Turkewitz et al. (2002)) and include over 7,000 species with 11 major subdivisions. *Tetrahymenids* and *Paramecium* belong to the Oligohymenophoreans. Ciliates that include mucocysts useful in the invention include *Tetrahymena* species such as *Tetrahymena thermophila* and *Tetrahymena pyriformis. Paramecium* has dense core granules but does not secrete a polypeptideaceous gel. Both *Tetrahymena thermophila* and *Tetrahymena pyriformis* produce mucocysts, and both secrete a proteinaceous gel.

*Tetrahymena* spp. are amenable to genetic manipulation, can be grown on a large scale and have a doubling time of 1.5-3 hrs. Unlike *T. thermophila*, which has an optimal growth temperature of 35° C., the optimal growth temperature for *T. pyriformis* is 34° C. Cells reach high-density in a short time on a variety of inexpensive media and can be expanded for growth in bioreactors up to several thousand liters in size (Hellenbroich et al. (1999); de Coninck et al. (2000)). Methods for transformation, along with robust, inducible promoters for driving high-level gene expression have recently been described for this system.

*Tetrahymena* spp. devote a large part of their metabolism to membrane polypeptide production due to the hundreds of cilia that extend from its surface (Williams et al. (1980)). Additionally, *Tetrahymena* spp. lack a cell wall and display high-mannose N-glycan polypeptide modifications that lack branched, immunogenic structures (Tanguchi et al. (1985); Beck et al. (2003); Weide et al. (2006)). Glycosylation patterns of secreted polypeptides in *Tetrahymena* spp. consist of high-mannose N-glycan structures that display minimal heterogeneity compared to other microbes such as yeast with glycans ranging from $Man_2GlcNAc_2$ to $Man_5GlcNAc_2$ with a majority of glycans comprising $Man_3GlcNAc_2$ structures similar to those which are produced in the endoplasmic reticulum of mammalian cells. This glycosylation pattern is unlike the glycosylation pattern produced in other microbial systems. For example, such glycosylation is non-existent in bacteria, and is highly branched and immunogenic in fungi.

*Tetrahymena* spp. produce abundant surface membrane polypeptides known as immobilization antigens (i-antigens). The expression of i-antigens is tightly regulated by environmental conditions (e.g., temperature), thus expression of a heterologous polypeptide containing an endogenous GPI anchor can be regulated by changes in temperature. Preer, *The Molecular Biology of Ciliated Protozoa*, pp. 301-339 (ed. J. G. Gall), Academic Press, New York (1986).

Ciliates can engage in regulated secretion of polypeptides stored in cortical secretory organelles (granules) which are discharged in a stimulus-dependent or regulated fashion (Miller et al. (1990)). Dense core granules are specialized for stimulus-dependent secretory granules that function in exocytosis in ciliates. In *Tetrahymena* spp., these dense core granules are termed mucocysts, whereas the dense core granules of *Paramecium tetraurelia* are termed trichocysts (Hausmann (1978); Rosati and Modeo (2003)).

Regulated secretion in ciliates can be triggered by the presence of chemical mediators known as secretagogues. For example, such mediators can cause increased levels of intracellular calcium ($Ca^{2+}$), which, in turn, trigger fusion of cortical granules with the plasma membrane resulting in a release of the granule contents into the surrounding extracellular space. Examples of secretagogues useful in the invention include, but are not limited to, dibucaine, alcian blue and $Ca^{2+}$ ionophores.

Mutant strains defective in the release of hydrolytic enzymes have also been isolated (Hunseler et al. (1992), *Dev. Genet.* 13:167-173). In some embodiments, mutant strains lacking or exhibiting reduced levels of secreted hydrolytic proteases can be used for the production of surface-expressed or secreted heterologous polypeptides.

Ciliate Genetics

Ciliates exhibit nuclear dimorphism and contain two distinct types of nuclei in each cell. The micronucleus (MIC or mic) is diploid and contains five pairs of transcriptionally inert chromosomes. The macronucleus is polyploid and functions as the transcriptionally active nucleus during vegetative growth. The micronucleus functions as the repository for genetic information for progeny produced by conjugation during sexual reproduction. During conjugation, the micronucleus undergoes meiosis to give rise to two pronuclei that are reciprocally exchanged between sexually mating cells. Upon fusion of the haploid gametes to produce a new zygotic micronucleus, the micronucleus undergoes two post-zygotic division resulting in the formation of new micronuclei and macronuclei. Upon formation of new macronuclei, the old macronuclei are resorbed are not transmitted to the sexual progeny. The cells then reproduce asexually until the next round of conjugation.

Differentiation of a macronucleus (MAC) from the mitotic products of zygotic micronuclei produced upon sexual reproduction involves several programmed DNA rearrangements, including but not limited to (1) the deletion of internal eliminated sequences (IESs) from the MIC genome, (2) programmed site-specific fragmentation of the five MIC chromosomes at specific chromosome breakage sequence (CBS) containing sites to form 250-300 MAC chromosomes, and (3) amplification to increase the copy numbers of the newly formed MAC chromosomes.

Chromosome Breakage

During programmed site-specific fragmentation, chromosome breakage occurs at about 50-200 specific sites along the five germline chromosomes at locations defined by a conserved 15 bp TAAACCAACCTCTTT (SEQ ID NO: 2) or TAAACCAACCTCATT (SEQ ID NO: 3) CBS to form new unprocessed MAC chromosomes (Yao et al. (1987), Cell 48:779-788; Yu and Blackburn (1991), Cell 67:823-832). CBSs are necessary and sufficient sequence signals for chromosome breakage in ciliates such as Tetrahymena. CBS sequences, regardless of copy number, orientation, and immediate flanking sequences, can serve as signals for site-specific chromosome breakage and telomere addition (Yao et al. (1990)). Subsequent processing results in the deletion of about 6 to about 30 bp on either side of the CBS and telomeres are then added de novo to the end to each newly formed MAC chromosome. Sequences residing adjacent to the CBS prior to breakage subsequently flank the new telomeric sequence following the breakage and processing events.

The process of chromosome breakage during MAC differentiation generates about 250 to about 300 MAC chromosomes having an average size of about 800 kb. These MAC chromosomes are maintained in the macronucleus during the ensuing vegetative cycle of a ciliate such as Tetrahymena.

During this process, a copy of the rDNA locus is excised from the micronuclear germline and undergoes rearrangement into 21 kb head-to-head palindromes bounded by 5' and 3' Non-Transcribed Spacers (NTS) (Karrer et al. (1976); King et al. (1982)).

Palindrome formation occurs via a mechanism dependent on the presence of short inverted repeats and intramolecular recombination. The 5'NTS, which is both necessary and sufficient for replication, contains nucleosome free regions (ori-D1 and ori-D2) that function as initiation sites for amplification as well as for mediating replication fork pausing at pause site elements (MacAlpine et al. (1997)). The NTSs also function to activate rRNA transcription (Pan et al. (1995)). This rDNA minichromosome functions as the transcriptionally active source for rRNAs (5.8S, 17S, and 26S rRNAs) during vegetative growth.

MAC Chromosome Amplification

Another stage of genetic reorganization during MAC differentiation is the amplification of MAC chromosomes. During the vegetative stage of Tetrahymena spp., transcriptionally active ribosomal RNA genes, which include genes encoding the 5.8S, 17S, and 26S rRNAs, reside on a small 21 kb MAC chromosome comprising two copies of the rRNA genes in the form of an inverted repeat. The MAC rRNA chromosome is formed upon breakage of the CBSs flanking the rRNA genes during differentiation of zygotic MIC nucleus during conjugation. The resulting MAC rRNA chromosome is then amplified and accumulated to about 9,000 copies per MAC, thereby resulting in an amplification of about 200-fold over the rest of the genome.

Vectors

Recombinant DNA for transformation of the ciliates described herein can be a vector, for example, any type of nucleic acid, plasmid, cosmid, virus, autonomously replicating sequence, phage, linear or circular, single- or double-strand DNA or RNA molecule, that can replicate in the ciliate itself or be incorporated into its genome. Vectors suitable for use as high copy number vectors for the delivery of heterologous DNA to Tetrahymena have been developed to take advantage of the process of rDNA amplification during macronuclear reorganization (Yu et al. (1989)). Such vectors have the advantage that DNA can be cloned and engineered in bacteria prior to transformation into a Tetrahymena host and replicate to high copy number. For example, the pD5H8 vector contains the a 119 bp linker located downstream of the 26S rRNA gene that is operably linked to a C3 rDNA such that a sequence inserted in the linker is retained in the rDNA following rearrangement of the plasmid DNA in conjugating cells to form an episomal plasmid derived minichromosome. Upon transformation into a ciliate, the CBS sequences in the rDNA vector are processed during macronuclear differentiation to produce an excision product that is the equivalent of the rDNA produced from normal processing of a micronuclear rDNA. The excision product from the vector is further processed to the macronuclear palindromic form and subsequently acts as a source for rDNA in the transformed cell.

In one aspect, methods described herein relate to the use of an rDNA vector that can be maintained as an autonomously replicating minichromosome when transformed into a ciliate host cell. The use of such rDNA based technologies for the introduction of recombinant DNA in ciliates such as T. thermophila results in an approximately 400-fold increase in copy number compared to cells that harbor transgenes somatically in the macronucleus (about 45 copies). While this increase in copy number is not necessarily linearly related to product yield, rDNA based expression has been shown to lead to higher product yield in T. thermophila.

Two different rDNA alleles are known to exhibit differential replication during vegetative growth in Tetrahymena. B and C3 rDNA alleles are both amplified in the new macronucleus of heterozygous progeny. The C3 rDNA allele, however, has a replication advantage over the B allele rDNA.

A small deletion in the B rDNA allele is responsible, in part, for its vegetative maintenance disadvantage (Larson et al. (1986); Yaeger et al. (1989)). The process of breakage results in the conversion of the rRNA into a palindrome via mechanisms dependent on the presence of short inverted repeat and intramolecular recombination. Thus, when introduced into T. thermophila B cell lines, the micronuclear version of the C3 rDNA is processed to form a palindrome and is maintained as a stable linear chromosome over many generations.

pIC-19-based rRNA based cloning vectors suitable for use as high copy number vectors for the delivery of heterologous DNA to Tetrahymena have been developed to take advantage of this process of amplification (Yu et al. (1988); Yu et al. (1989)). The design of these vectors is based in part on the existence of different rDNA alleles in *T. thermophila* having sequence variations within their respective origins of replication. Specifically, rDNA from strain C3 has a replication advantage over a genetic variant rDNA from strain B when they are present in the same macronucleus. When both B and C3 rDNA are present a macronucleus, the B variant is virtually eliminated within about 30 fissions. In certain embodiments of the invention described herein, C3 rDNA can become the sole macronuclear rDNA species. The methods described herein relate in part to the replicative advantage of the C3 rDNA allele in a ciliate such as *Tetrahymena* having a homozygous B allele genotype. In one aspect, the methods described herein relate to the use of an rDNA vector (e.g., the pD5H8 vector) comprising a transgene cassette operably linked to the rDNA locus of the vector. This feature has been used for the introduction of transgenes to a potential copy number of 18,000 per cell.

Although methods of selecting transformants are readily known to one skilled in the art, such methods suffer from loss of efficacy due to genetic instability. For example, a point mutation in the 17S rDNA, which confers resistance to neomycin, can be used for the purpose of direct selection of rDNA transformants (5, 6), however such vectors are unstable and are lost within 50 to 80 generations. Specifically, a disadvantage of current approaches that utilize the pD5H8 vector is the use of a neomycin phosphotransferase (neo) gene (which in *Tetrahymena* confers resistance to paromomycin) as a selection marker linked to a transgene of interest. This selection marker is redundant to the effect of a point mutation in the C3 allele 17S rDNA in the rDNA locus comprised in the pD5H8 vector, which itself confers resistance to paromomycin, and can be used for the purpose of direct selection of rDNA transformants (Spangler et al. (1985); Bruns et al. (1985)).

Because a neo resistance cassette linked to transgene in pD5H8 is redundant to paromomycin resistance derived from the mutated 17S C3 rDNA allele, loss of transgene expression products can occur due to genetic instability by uncoupling of paromomycin resistance from the transgene expression cassette. Without being bound by theory, such uncoupling can occur by recombination and loss of the transgene even when paromomycin resistance is maintained by expression of the mutated 17S C3 rDNA from the rDNA vector derived rDNA minichromosome. Again, without being bound by theory, another source of genetic instability can stem from hybrid palindromes of recombinant rDNA chromosomes where one arm contains the transgene cassette and the other contains WT rDNA. Over time, strains containing hybrid rDNA chromosomes can revert to WT rDNA and result in loss of the transgene.

In one aspect, the methods described herein relate to the use of an rDNA vector comprising a selection maker other than a neomycin phosphotransferase (neo) gene linked to the transgene. In one embodiment, an rDNA vector, as described herein, can comprise (1) a C3 rDNA locus, (2) a selection maker other than a neomycin phosphotransferase (neo) gene, and (3) a transgene cassette, wherein the C3 rDNA locus, the selection marker other than a neomycin phosphotransferase (neo) gene, and the transgene cassette are bounded by a 5' and a 3' CBS such that macronuclear reorganization in a ciliate transformed with the vector will result in the formation of a macronuclear minichromosome capable of expressing vector-derived rDNA, the selection marker and a polypeptide encoded by the transgene cassette.

The rDNA vector described herein can comprise an rDNA locus allele wherein the mutated C3 17S rDNA allele in the rDNA locus has been modified such that it can no longer confer resistance to paromomycin. In some embodiments, the 17S C3 rDNA allele in the rDNA locus of the rDNA vector can be replaced with a 17S rDNA allele from a B rDNA locus allele. In other embodiments, the 17S rDNA allele in the rDNA locus of the rDNA vector can be replaced with a 17S rDNA from any other known 17S rDNA allele that does not confer resistance to paromomycin. In further embodiments, the 26S rDNA can be replaced with a mutated version conferring resistance to anisomycin (Sweeney et al. (1991))

In some embodiments, an rDNA vector, as described herein, can comprise (1) a C3 rDNA locus, (2) a selection maker other than a neomycin phosphotransferase (neo) gene, and (3) a transgene cassette, wherein the C3 rDNA locus and the transgene cassette are bounded by a 5' and a 3' CBS as well as a section marker such that macronuclear reorganization in a ciliate transformed with the vector will result in the formation of a macronuclear minichromosome capable of expressing vector-derived rDNA and a polypeptide encoded by the transgene cassette. An rDNA vector, as described herein, can include one or more selection marker genes.

In some embodiments, a selection marker can be operably integrated into the rDNA vector such that it can confer resistance to one or more biostatic or biocidal drugs when the rDNA vector is maintained in an episomal state. In other embodiments, the selection marker can be operably integrated into the rDNA vector such that it can confer resistance to one or more biostatic or biocidal drugs when a minichromosome derived from the rDNA vector is generated during macronuclear reorganization. In still further embodiments, the selection marker can be operably integrated into the rDNA vector such that it can confer resistance to one or more biostatic or biocidal drugs when the rDNA vector is maintained in an episomal state and when a minichromosome derived from the rDNA vector is generated during macronuclear reorganization.

A number of selection markers are suitable for use with the vectors and methods described herein. Such selectable marker genes and their corresponding selection agents include, but are not limited to aminoglycoside phosphotransferase (APH) and G418; dihydrofolate reductase (DHFR) and methotrexate (Mtx); hygromycin-B-phosphotransferase (HPH) and hygromycin-B; balsticidin and blasticidin resistance gene (bsr); xanthine-guanine phosphoribosyltransferase (XGPRT) and mycophenolic acid; adenosine deaminase (ADA) and 9-β-D-xylofuranosyl adenine (Xyl-A); and ribosomal polypeptide L29 (CYH2) and cycloheximide. Another selectable marker system employs AmpR and ampicillin. Selectable marker genes that confer sensitivity or susceptibility to a normally non-toxic selection agent cause only successfully transfected cells to die in the presence of the selection agent are referred to as negative selectable markers. Phenotypic selectable marker genes permit selection based upon morphological or biochemical traits rather than cell death or survival. In some cases, the phenotypic marker is detectable only in the presence of an additional selection agent.

Homologous Recombination

In one aspect, the subject matter disclosed herein relates to an expression vector for expression of recombinant polypeptides in ciliates. An expression vector, according to the invention, can be a nucleic acid molecule, like DNA or RNA, circular or linear, for example, a plasmid, a cosmid or an artificial chromosome, that allows expression of a recombinant gene in a host cell (e.g., *Tetrahymena*). Such expression vectors can be present episomally in the cell (i.e., be self-replicating) or can be integrated into the genome of the host cell. Integration events can occur randomly or by homologous recombination. In some embodiments, the methods and compositions described herein relate to an expression vector that undergoes homologous recombination with the genome of a host cell.

Gene targeting by means of homologous recombination between homologous exogenous DNA and endogenous chromosomal sequences is useful for the creation of genetically modified organisms. Homologous recombination relies, in part, on the ability of nucleic acids to base pair with complementary sequences. In the case of homologous recombination, the base pairing enables the interaction of two separate nucleic acid molecules so that strand breakage and repair can take place. Thus, the method relies on sequence homology to bring two complementary sequences into close proximity, at which point recombination can cause one complementary sequence to replace the other by virtue of the breaking of certain bonds and the formation of others.

One skilled in the art can design a vector suitable for homologous recombination. Briefly, a target gene or region can be selected within a host cell for modification by homologous recombination. Such modifications can include, but are not limited to, one or more deletions, mutations or insertions. For example, a deletion that renders a target gene inactive can be used in conjunction with the methods described herein. The homologous sequences flanking the deletion are said to "flank" the mutation. Flanking, in this context, simply means that target homologous sequences are located both upstream (5') and downstream (3') of the mutation. For homologous recombination to occur upon introduction of the vector into a cell, these sequences should correspond to some sequences upstream and downstream of the target gene or target region. The construct is then introduced into the cell, thus permitting recombination between the cellular sequences and the construct.

Various methods for selecting cells that have undergone homologous recombination are well known in the art. For example, an expression vector designed to result in the stable integration of a recombinant nucleic acid by homologous recombination can include one or more selection markers genes. The selection marker enables selection of cells that have integrated the construct into their genomic DNA by conferring resistance to various biostatic or biocidal drugs. In addition, a heterologous gene that is to be expressed in the cell also may be included within the construct. Thus, the use this type of construct enables (i) the modification of an endogenous gene, (ii) the inclusion of a selectable marker for identifying such an event and (iii) introduce a heterologous gene for expression.

Universal Recipient Lines with Non-Functional Micronuclear rDNA Loci

Described herein are methods and compositions useful for the expression of a recombinant polypeptide in a ciliate. In some embodiments, expression of the recombinant polypeptide can be achieved by transforming a genetically modified ciliate lacking one or more micronuclear rDNA genes or having one or more non-functional micronuclear rDNA genes with an rDNA rescue vector encoding the missing or non-functional rDNA gene(s). Cells lacking one or more micronuclear rDNA genes or having one or more non-functional micronuclear rDNA genes will be conditionally viable and unable to survive sexual reproduction through conjugation. Accordingly, transformation of such cells with a rescue vector capable of correcting the rRNA deficiency will render such cells conjugation competent. In some embodiments, the rDNA rescue vector can further comprise a transgene expression cassette such that cells rendered conjugation competent by the methods described herein will also express a recombinant polypeptide encoded by the transgene.

Such genetically modified conjugation incompetent ciliate host cells will be viable in the vegetative state as heterokaryons because rRNA genes are not expressed from the micronuclear genome during vegetative growth and there will accordingly be no impact on the viability of such cells until the cell engages in sexual reproduction by conjugation. In some embodiments, the conditional lethality of the genetic modification will occur upon exit from the vegetative state (e.g., macronuclear differentiation upon conjugation).

Without being bound by theory, the heterokaryonic cells will no longer be viable because the progeny of the cells will obtain their rRNA-encoding genes from the micronuclei of the parental strains and when macronuclei are resorbed upon sexual reproduction by conjugation, the absence of one or more functional rDNA genes will cause lethality. Accordingly, the conditional conjugation-lethality of the genetic modification will be evident upon macronuclear differentiation (i.e., upon sexual reproduction). For example, such genetically modified ciliate host cells will be viable in the vegetative state due to somatic rRNA expression derived form the macronucleus. Cell viability can be restored in such conditionally conjugation-lethal genetically modified ciliate hosts cell lacking one or more micronuclear rDNA genes or having one or more non-functional micronuclear rDNA genes by transformation with an rDNA rescue vector.

The universal recipient cells described herein can be created using standard techniques known in the art. For example, *Tetrahymena* cells can be transformed with a homologous recombination vector capable of replacing one or more functional rDNA genes in the micronuclear rDNA locus with a nucleotide sequence that reduces or abolishes function or expression of the rRNA upon macronuclear reorganization in the vegetative state. The homologous recombination vector can further comprise a selection marker such that cells in which the micronuclear rDNA locus is nonfunctional by homologous recombination can be selected by growth in a biostatic or biocidal drug. Such cells will remain viable in the vegetative state because macronuclear chromosomes capable of expressing all of the rRNA genes required for survival will already be present in the macronucleus. Such cells can be selected on the basis of a selection marker encoded in the homologous recombination vector such that only those cells undergoing homologous recombination, and thus only those cells now lacking one or more micronuclear rDNA genes or having one or more non-functional micronuclear rDNA genes will propagate in the presence of appropriately selected biostatic and biocidal drugs. The universal recipient will not be capable of undergoing sexual conjugation because, after macronuclear reorganization following conjugation, the micronuclear rDNA locus will be non-functional and will be incapable of giving rise to a macronuclear rDNA chromosome capable of expressing the rRNAs necessary for survival of the cell in the vegetative state. In some embodiments, the universal recipient cells can be heterokaryons carrying a selectable marker that does not interfere with downstream selections. Many suitable selection markers are known in the art, including, for example, 6-methylpurine.

The universal recipient cells described herein can further comprise any known polymorph of the rDNA locus. In one embodiment, the universal recipient cell can have a B rDNA locus polymorph. In another embodiment, the universal recipient cell can have a C3 rDNA locus polymorph. Without being bound by theory, in some embodiments, universal recipient cells having a C3 rDNA locus polymorph can comprise a 17S rRNA encoding gene comprising a point mutation that confers resistance to paromomycin and hygromycin such that the cells can be grown in paromomycin or hygromycin.

rDNA Rescue

In some embodiments, the rescue event can occur in the absence of homologous recombination. For example, where the recipient cell line has a deletion of all or substantially all of the micronuclear rDNA locus, transformation with an rDNA rescue vector comprising a complete copy of an rDNA locus will not allow recombination between micronuclear DNA and the rDNA rescue vector. Accordingly, any transgene cassette comprised within the rDNA rescue vector will not be lost by phenotypic assortment. In one embodiment, rescue of universal recipient cells can be performed by transformation with an rDNA rescue vector comprising a complete copy of the micronuclear rDNA locus flanked by functional CBS regions on both the 3' and 5' ends. In some embodiments, the rDNA locus in the rDNA rescue vector can be a B polymorph rDNA locus. In other embodiments, the rDNA locus in the rDNA rescue vector can be a C3 polymorph rDNA locus. The CBS sequences in the transformation vector are then processed like other CBS regions naturally present in the genome, and produce an excision product that is the equivalent of the rDNA produced from normal processing of the micronuclear rDNA flanking CBS regions. The excision product from the vector is further processed to the macronuclear palindromic form and subsequently acts as the source for rDNA in the rescued cell.

In some embodiments, the rDNA rescue vector can further comprise a transgene cassette of interest (e.g., the transgene cassette can be in the 3' non-transcribed sequence of an rDNA gene). In some embodiments, a transgene cassette can be inserted into the 3' non translated sequence of the rDNA locus in the rDNA rescue vector.

In some embodiments, the universal recipient cells described herein can be transformed with a homologous recombination vector having both a transgene cassette and one or more functional rDNA genes.

In other embodiments, the rDNA rescue vector can comprise a selection marker, such that cells that have been transformed with the rescue vector, whether or not they have undergone homologous recombination with the rDNA rescue vector, can also be selected by growth in a biostatic or biocidal drug.

In some embodiments, the rDNA rescue vector can comprise a selection marker and a transgene cassette such that cells transformed with the rDNA rescue vector can be grown in a selective medium whether or not the rDNA rescue vector undergoes homologous recombination with any micronuclear genomic sequence in the universal recipient cell.

The rDNA rescue vectors described herein can further comprise any rRNA encoding nucleotide sequence or polymorph. In some embodiments, the rDNA rescue vector can comprise an rRNA-encoding nucleotide sequence corresponding to a B polymorph rRNA. In other embodiments, the rDNA rescue vector can comprise an rRNA-encoding nucleotide sequence corresponding to a C3 polymorph rRNA. Without being bound by theory, in some embodiments, an rDNA rescue vector comprising a C3 rDNA locus polymorph can comprise a 17S rRNA encoding gene comprising a point mutation that confers resistance to paromomycin or hygromycin such that the cells transformed with the vector can be grown in paromomycin or hygromycin upon homologous recombination following macronuclear reorganization.

rDNA Knockout Vectors

A vector useful for generating a universal recipient cell having a non-functional or deleted micronuclear rDNA locus can comprise an rDNA knockout cassette suitable for replacing the micronuclear DNA segment extending from a sequence between the 5' CBS flanking the micronuclear rDNA locus and the 3' CBS flanking the micronuclear rDNA locus. Accordingly, the two regions of homology between the rDNA knockout construct and the rDNA rescue construct can be designed to complement one another such that deletion, substitution, insertion or inversion of one or more nucleic acids by homologous recombination with an rDNA knockout vector can be reversed by homologous recombination with the rDNA rescue vector.

In some embodiments, a selection marker can be operably integrated into the rDNA knockout vector such that it can confer resistance to one or more biostatic or biocidal drugs when the rDNA knockout vector is integrated or maintained in an episomal state. In other embodiments, the selection marker can be operably integrated into the rDNA knockout vector such that it can confer resistance to one or more biostatic or biocidal drugs when a minichromosome derived from the rDNA knockout vector is generated during macronuclear reorganization. In still further embodiments, the selection marker can be operably integrated into the rDNA knockout vector such that it can confer resistance to one or more biostatic or biocidal drugs when the rDNA knockout vector is maintained in an episomal state and when a minichromosome derived from the rDNA knockout vector is generated during macronuclear reorganization.

DNA Vectors

Recombinant DNA for transformation of the genetically modified ciliates described herein can be a vector, for example, any type of nucleic acid, plasmid, cosmid, virus, autonomously replicating sequence, phage, linear or circular, single- or double-strand DNA or RNA molecule, that can replicate in the target organism itself or be incorporated into its genome.

A heterologous nucleic acid transformed into a ciliate can be maintained extrachromosomally on an autonomous plasmid. Heterologous nucleic acids can also be introduced into the ciliate host on an expression vector that is capable of integrating into the host's genome. For example, expression vectors capable of homologous recombination with a highly expressed gene that is endogenous to the ciliate host, such as a beta-tubulin gene are known in the art.

Expression vectors useful for transforming ciliates in accordance with the methods described herein include but are not limited to rDNA rescue vectors (e.g., replacement vectors), rDNA vectors, and rDNA-based vectors. Rescue vectors accomplish DNA-mediated transformation by replacing or altering endogenous genes using homologous recombination. Integration of the heterologous nucleic acid into the host's genome at the targeted site is accomplished via homologous recombination involving a crossover event with the vector containing the heterologous nucleic acid. An example of an expression vector useful for genomic incorporation of a heterologous nucleic acid by replacement is one that targets a transgene to the beta-tubulin locus and is selectable by growth in appropriate drugs (Gaertig et al. (1999)).

Methods for creating mitotically stable transformants of ciliates (e.g., *Tetrahymena* spp.) are known in the art. For example, methods for generating *Tetrahymena* spp. having targeted gene knockouts by homologous DNA recombination are known in the art (Bruns & Cassidy-Hanley in: *Methods in Cell Biology*, Vol. 62, Asai & Formey (eds.), Academic Press (1999), pp. 501-512); Hai et al. in: *Methods in Cell Biology*, Vol. 62, Asai & Formey (eds.), Academic Press (1999) 514-531; Gaertig et al. (1999), *Nature Biotech.* 17:462-465; Cassidy-Hanley et al. (1997), *Genetics* 146:135-147).

A replacement vector can include a 5' region, followed by a heterologous coding region, followed by a 3' region, wherein at least a portion of each of the 5' and 3' regions is complementary to 5' and 3' regions on an endogenous gene of the host, to allow for genomic integration of the heterologous coding region via homologous recombination. The 5' and 3' regions of the vector can also comprise regulatory elements, such as a promoter and a terminator. The necessary regulatory elements can also be supplied by the endogenous gene into which the heterologous coding region integrates. Suitable regulatory regions include, but are not limited to promoters, termination sequences, signal peptides and propolypeptide domains involved in the expression and secretion of polypeptides. For example, such regulatory elements can provide efficient heterologous expression of polypeptides in ciliates under control of promoters and/or terminators which are derived from genes in ciliates. Such vectors can comprise naturally occurring promoters and/or terminators from polypeptides secreted at a high level in ciliates. The expression of recombinant polypeptides in ciliates can be driven by strong promoters, pre/pro sequences and terminators. In some embodiments, the promoters and/or terminators can be selected from polypeptides secreted at a high level independent of the cell-cycle in Tetrahymena spp. (see, e.g., U.S. Patent Publication 2006/0127973; WO2003/078566). Inducible promoters from Tetrahymena spp. genes have also been described that allow robust expression of heterologous genes. For example, heat-inducible promoters of the heat shock polypeptide family of the ciliate Tetrahymena spp. are also suitable for use with the methods described herein. Suitable heat shock promoters from Tetrahymena spp. are known in the art (see, e.g., WO2007/006812).

Expression vectors can also be maintained extrachromosomally in ciliates. For example, such extrachromosomal elements can be rDNA-based vectors containing an on from Tetrahymena spp. Such vector can further comprise a 5' regulatory region from an endogenous Tetrahymena spp. gene containing a promoter region operably linked to the heterologous coding region and/or a 3' regulatory region from the same or a different Tetrahymena spp. gene. Suitable regulatory regions from ciliate genes are well known in the art.

Vectors suitable for use with the methods described herein include, but are not limited to: the pXS76 shuttle vector (which can be used for insertion of transgenes downstream of a cadmium-inducible promoter from the MTT1 metallothionein gene), rDNA vectors (Tondravi et al. (1986), Proc. Natl. Acad. Sci. USA 83:4396; Yu et al. (1989), Proc. Natl. Acad. Sci. USA 86: 8487-8491), high copy number ribosomal DNA vectors (such as pD5H8). For example, an rDNA-based vectors can be a circular vector containing 5' non-translated sequences comprising two or more on sequences from Tetrahymena spp. One or more nucleic acid fragments containing heterologous coding regions (e.g., a transgene or a selectable marker) can also be added to the vector using methods known to one skilled in the art. Such vectors can further comprise 5' untranslated regions of a Tetrahymena spp. genes and a 3' untranslated regions of a Tetrahymena spp. genes. These untranslated regions can be inserted upstream and downstream of the selectable marker and/or the transgene.

The nucleotide sequences herein can be cloned using standard cloning procedures in the art, as described by Sambrook et al., Molecular Cloning: A Laboratory Manual, Second Edition, Cold Springs Laboratory, Cold Spring Harbor, N.Y. (1989).

One skilled in the art will also appreciate that for a transgene to be expressed in a ciliate, such as Tetrahymena, additional regulatory factors much be operatively linked to a coding sequence. These regulatory regions include, but are not limited to a promoter, a polyadenylation sequence, a transcriptional start site, a translation start site and the like. For example, a functional promoter can have, among other things, one or more TATA boxes, CCAAT boxes, GC boxes or enhancer sequences. A transgene suitable for use with the methods and compositions described herein can also include a terminator functional in one or more types of ciliates. A signal sequence that directs polyadenylation of mRNA may also be required in order to achieve expression of a desired transgene in a ciliate. One of skill in the art will further recognize that the coding sequence of the functional gene will also contain elements that direct translation of the encoded mRNA in the target organism. For example, a start codon (for example, ATG), a stop codon (TGA), an A-rich region before the start (translation initiation site), one or more Kozak sequences, and a poly-A site can all be required for the expression of a transgene in a ciliate. It is also possible to modify transgenes such that codon usages specific for a ciliate such as Tetrahymena is employed (Wuitschick & Karrer (1999)). Thus in one embodiment, any functional promoter, terminator, polyadenylation signal or any other regulatory region that required to express a transgene in the context of the rDNA rescue vector (or any macronuclear chromosomes derived therefrom) can be used in conjunction with the methods and compositions described herein. One skilled in the art will readily be able to devise a strategy to cause a transgene to be expressed according to the methods described herein.

Such regulatory elements can provide efficient expression of recombinant polypeptides in ciliates under control of promoters and/or terminators which are derived from genes in ciliates such as Tetrahymena spp. The expression of recombinant polypeptides in ciliates can be driven by strong promoters, pre/pro sequences and terminators. In some embodiments, the promoters and/or terminators can be selected from polypeptides secreted at a high level independent of the cell-cycle in Tetrahymena spp (see, e.g., U.S. Patent Publication 2006/0127973; WO2003/078566). Inducible promoters from ciliate genes have also been described that allow robust expression of heterologous genes. For example, heat-inducible promoters of the heat shock polypeptide family of the ciliate Tetrahymena spp. are also suitable for use with the methods described herein. Suitable heat shock promoters from Tetrahymena spp. are known in the art (see, e.g., WO2007/006812).

Polypeptide Production

In one aspect, the methods described herein relate to the production of a recombinant polypeptide in ciliates. In some embodiments, the ciliate can have a micronuclear rDNA locus homozygous for the B rDNA allele such that transformation of the ciliate with an rDNA vector comprising a C3 rDNA locus, will result a ciliate having both micronucleus derived B allele rDNA minichromosomes and an rDNA vector derived C3 rDNA minichromosomes. In other embodiments, the rDNA vector derived C3 rDNA minichromosomes can further comprise an rDNA vector-derived transgene cassette. In other embodiments, the rDNA vector can further comprise an rDNA vector-derived selection marker.

In yet another aspect, the invention relates to methods useful for the production of a recombinant polypeptide in a ciliate, the methods comprising (a) transforming a ciliate with an rDNA vector or an rDNA rescue vector, wherein the vector further comprises a nucleotide sequence encoding the recombinant polypeptide; (b) culturing the ciliate to produce the recombinant polypeptide; and (c) isolating the recombinant polypeptide. In some embodiments, the ciliate has a homozygous B rDNA allele micronuclear genotype.

Without being bound by theory, the replicative advantage of the C3 rDNA minichromosome will eventually result in the elimination of the B rDNA allele minichromosome during vegetative growth such that the only source of rRNA expression will be the rDNA vector derived C3 minichromosome.

Transformation

Genes can be introduced into ciliates using established protocols or any method known to one skilled in the art. Transformation of ciliates can be achieved by microinjection (Tondravi and Yao (1986), *Proc. Natl. Acad. Sci. USA* 83:4369-4373), electroporation (Gaertig and Gorovsky (1992), *Proc. Natl. Acad. Sci. USA* 89:9196-9200), or biolistically (Cassidy-Hanley et al. (1997), *Genetics* 146:135-147). Alternatively, transformation of the somatic macronucleus or the generative micronucleus is also possible in *Tetrahymena* spp.

Transformation can be performed at different times during meiosis during conjugation depending on whether the target is micronuclear transformation or macronuclear transformation. In some embodiments, universal recipient cells can be transformed with an rDNA rescue vector during the early stages on conjugation. In other embodiments, universal recipient cells can be transformed with an rDNA rescue vector during the vegetative state (e.g., a starvation induced vegetative state) as long as transformation occurs prior to fertilization. In some embodiments, biolistic transformation can be used for micronuclear transformation. In other embodiments, micronuclear transformation can be used to create the universal recipient cells.

Transformation performed during conjugation can be highly conjugation stage specific, as well as have time and temperature dependence. For example, in the case of macronuclear transformation, transformation has to occur late in conjugation when the cells are normally processing the native CBS regions in the genome. In the case of micronuclear transformation, for example for the creation of universal recipient strains having a non-functional micronuclear rDNA locus, or for the creation of parent strains having one or more non-functional rDNA genes, conjugating cells must be transformed early in mating prior to the completion of meiosis and haploid zygote nucleus formation. See Cassidy-Hanley et al. (1997). Flanking regions of homology are essential for all homologous transformation, and biolistic transformation can be used for micronuclear transformation.

All cells in a population may not necessarily be transformed during a transformation protocol. Nevertheless, the true progeny survivors of the genetically modified ciliates described herein transformed with an rDNA rescue vector comprising a transgene cassette will be capable of expressing a heterologous polypeptide encoded by the transgene. Thus, although conjugation is not completely synchronous in ciliates, synchronization need only be sufficient to yield some survivors. However, there is also a workaround involving selection against non-maters based on parent strains that are functional heterokaryons for a selectable marker. Parental strains which are functional heterokaryons, (i.e., strains which carry a non-expressed selectable marker in the micronucleus but not in the macronucleus) will not express the selectable marker. Any cells which do not undergo conjugation and the formation of a new macronucleus will be killed by the selection agent. Mating brings the micronuclear gene into expression in the newly formed macronucleus in progeny cells, and true progeny will therefore be resistant to the selection agent. As a result only true progeny will survive selection.

In some embodiments, ciliate cells can be transformed with a chimeric gene by particle bombardment (also known as biolistic transformation) (Cassidy-Hanley et al. (1997), *Genetics* 146:135-147). Particle bombardment transformation can be achieved in several ways. For example, inert or biologically active particles can be propelled at cells under conditions effective to penetrate the outer surface of the cell and to be incorporated within the interior thereof. When inert particles are utilized, the vector can be introduced into the cell by coating the particles with the vector containing the chimeric gene. Alternatively, the target cell can be surrounded by the vector so that the vector is carried into the cell by the wake of the particle. Other variations of particle bombardment, now known or hereafter developed, can also be used.

Microcarrier bombardment can also be used to transform ciliate cells by means of DNA-loaded gold particles (U.S. Pat. No. 6,087,124; EP 0 847 444; WO1998/001572). In this approach, microcarrier bombardment with DNA-coated gold is used as a means of introducing heterologous genes into ciliates. In some embodiments, microcarrier bombardment can be used to transform ciliates and introduce genes into the (germline) micronucleus. In other embodiments, DNA-coated tungsten particles can be used for biolistic transformation.

Methods for selection of transformed cells harboring heterologous genes are known in the art. For example, the vector can further comprise a selectable cassette marker to permit selection for transformed cells (e.g., a neo 2 cassette) (Gaertig et al. (1994), *Nucleic Acids Res.* 22:5391-5398. Selection of transformants can be achieved by growing the cultured ciliates in a medium which allows only the transformants to survive. Suitable selection agents include antibiotics which will kill all non-transformants but allow transformants (which also possess an antibiotic resistance gene) to survive. A number of antibiotic-resistance markers are known in the art. Any known antibiotic-resistance marker can be used to transform and select transformed host cells in accordance with the present invention. For example, a *Tetrahymena* cells homozygous for a B allele micronuclear rDNA locus can be transformed with an rDNA vector comprising (1) a transgene cassette capable of driving expression of a recombinant polypeptide encoded by the transgene and (2) a selection marker that does not confer resistance to a selection agent other than paromomycin.

Recombinant Polypeptides/Peptides

The genetically modified ciliates described herein can be used to express a recombinant polypeptide or peptide of any species and of any size. For example, the genetically modified ciliates described herein can be transformed with an rDNA vector or an rDNA rescue vector comprising a transgene cassette capable of driving expression of a recombinant polypeptide encoded by the transgene. In some embodiments, the recombinant polypeptide or peptide can be a therapeutically useful polypeptide or peptide. In other embodiments, the polypeptide can be a mammalian polypeptide, for example a human polypeptide, and can be, for example, a growth factor, a cytokine, a chemokine or a blood polypeptide. The recombinant polypeptide or peptide can be expressed primarily in an inactive form in the host cell. In certain embodiments, the recombinant polypeptide or peptide is between about 1 kDa to about 10 kDa, between about 10 kDa to about 20 kDa, between about 20 kDa to about 50 kDa, between about 50 kDa to about 100 kDa, between about 100 kDa to about 200 kDa, between about 200 kDa to about 400 kDa, between about 400 kDa to about 800 kDa, between about 800 kDa to about 1,500 kDa, or greater than 1,500 kDa. In certain embodiments, the recombinant polypeptide or peptide is a peptide of at least 5, 10, 15, 20, 30, 40, 50 or 100 amino acids.

In some embodiments, the nucleotide sequence of the transgene encoding the recombinant peptide can be modified to have properties that promote for translation in the *Tetrahymena* or genetically modified ciliates described herein. For example, in *Tetrahymena*, the ATG start codon, the TGA stop codon, and A-rich regions before translation initiation sites, Kozak sequences, poly-A site can be operably linked to a heterologous coding sequence. Codon usage corresponding to *Tetrahymena* spp. has also been described, and methods to modify heterologous coding sequences in accordance with codon usage, for example through silent mutagenesis, or through mutagenesis resulting in conservative amino acid substitutions are readily known to one skilled in the art (Wuitschick and Karrer (1999)).

Transgenes suitable for use with the methods and genetically modified ciliates described herein include genes encoding polypeptides that are, e.g., at least about 60%, 70%, 75%, 80%, 90%, 95%, or at least about 99% or more identical to any available polypeptide.

Transgenes suitable for use with the methods and compositions described can be any naturally occurring or synthetic (artificial) therapeutic, diagnostic, bio-molecule, peptides, polypeptides, or polypeptides that can be modified as discussed by the present invention. Some examples of transgenes include, but are not limited to, e.g., alpha-1 antitrypsin, angiostatin, antihemolytic factor, antibodies (including an antibody or a functional fragment or derivative thereof selected from: Fab, Fab', F(ab).sub.2, Fd, Fv, ScFv, diabody, tribody, tetrabody, dimer, trimer or minibody), angiogenic molecules, angiostatic molecules, apolipopolypeptide, apopolypeptide, asparaginase, adenosine deaminase, atrial natriuretic factor, atrial natriuretic polypeptide, atrial peptides, angiotensin family members, Bone Morphogenic Polypeptide (BMP-1, BMP-2, BMP-3, BMP-4, BMP-5, BMP-6, BMP-7, BMP-8a, BMP-8b, BMP-10, BMP-15, etc.); C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., monocyte chemoattractant polypeptide-1, monocyte chemoattractant polypeptide-2, monocyte chemoattractant polypeptide-3, monocyte inflammatory polypeptide-1alpha, monocyte inflammatory polypeptide-1beta, RANTES, 1309, R83915, R91733, HCC1, T58847, D31065, T64262), CD40 ligand, C-kit Ligand, Ciliary Neurotrophic Factor, Collagen, Colony Stimulating Factor (CSF), Complement factor 5a, Complement inhibitor, Complement receptor 1, cytokines, (e.g., epithelial Neutrophil Activating Peptide-78, GROalpha/MGSA, GRObeta, GROgamma, MIP-1alpha, MIP-1delta, MCP-1), deoxyribonucleic acids, Epidermal Growth Factor (EGF), Erythropoietin ("EPO", representing a preferred target for modification by the incorporation of one or more non-natural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog polypeptides (e.g., Sonic, Indian, Desert), Hemoglobin, Hepatocyte Growth Factor (HGF), Hepatitis viruses, Hirudin, Human serum albumin, Hyalurin-CD44, Insulin, Insulin-like Growth Factor (IGF-I, IGF-II), interferons (e.g., interferon-alpha, interferon-beta, interferon-gamma, interferon-epsilon, interferon-zeta, interferon-eta, interferon-kappa, interferon-lamda, interferon-tau, interferon-c, interferon-omega), glucagon-like peptide (GLP-1), GLP-2, GLP receptors, glucagon, other agonists of the GLP-1R, natriuretic peptides (ANP, BNP, and CNP), Fuzeon and other inhibitors of HIV fusion, Hurudin and related anticoagulant peptides, Prokineticins and related agonists including analogs of black mamba snake venom, TRAIL, RANK ligand and its antagonists, calcitonin, amylin and other glucoregulatory peptide hormones, and Fc fragments, exendins (including exendin-4), exendin receptors interleukins (e.g., IL-1, IL-2, IL-3, IL-4, IL-5, IL-6, IL-7, IL-8, IL-9, IL-10, IL-11, IL-12, etc.), I-CAM-1/LFA-1, Keratinocyte Growth Factor (KGF), Lactoferrin, leukemia inhibitory factor, Luciferase, Neurturin, Neutrophil inhibitory factor (NIF), oncostatin M, Osteogenic polypeptide, Parathyroid hormone, PD-ECSF, PDGF, peptide hormones (e.g., Human Growth Hormone), Oncogene products (Mos, Rel, Ras, Raf, Met, etc.), Pleiotropin, Polypeptide A, Polypeptide G, Pyrogenic exotoxins A, B, and C, Relaxin, Renin, ribonucleic acids, SCF/c-kit, Signal transcriptional activators and suppressors (p53, Tat, Fos, Myc, Jun, Myb, etc.), Soluble complement receptor I, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, somatomedin, somatostatin, somatotropin, streptokinase, superantigens, Staphylococcal enterotoxins (SEA, SEB, SEC1, SEC2, SEC3, SED, SEE), Steroid hormone receptors (such as those for estrogen, progesterone, testosterone, aldosterone, LDL receptor ligand and corticosterone), superoxide dismutase (SOD), Toll-like receptors (such as Flagellin), Toxic shock syndrome toxin (TSST-1), Thymosin alpha1, Tissue plasminogen activator, transforming growth factor (TGF-alpha, TGF-beta), Tumor necrosis factor beta (TNF-beta), Tumor necrosis factor receptor (TNFR), Tumor necrosis factor-alpha (TNF-alpha), transcriptional modulators (for example, genes and transcriptional modular polypeptides that regulate cell growth, differentiation and/or cell regulation), Vascular Endothelial Growth Factor (VEGF), virus-like particle, VLA-4/VCAM-1, Urokinase, signal transduction molecules, estrogen, progesterone, testosterone, aldosterone, LDL, corticosterone amidase, amino acid racemase, acylase, dehalogenase, dioxygenase, CD40L/CD40, diarylpropane peroxidase, epimerase, epoxide hydrolase, esterase, isomerase, kinase, glucose isomerase, glycosidase, glycosyl transferase, haloperoxidase, monooxygenase, lipase, lignin peroxidase, nitrile hydratase, nitrilase, protease, phosphatase, subtilisin, transaminase, nuclease, a cytokine, Factor VII, Factor VIII, Factor IX, Follitropin, G-CSF, GM-CSF, GLP-1, human growth hormone, interferon-alpha, interferon-beta, interferon-gamma, interferon-omega., interferon-tau, a transcriptional modulator that modulates cell growth, differentiation, or regulation, expression activator, inflammatory molecule, growth factor, growth factor receptor, and oncogene product.

Target molecules include transcriptional modulators, signal transduction molecules and oncogene products, which may be found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to polypeptides that bind to promoters and enhancers, unwinding DNA, splicing pre-mRNA, polyadenylating RNA, and degrading RNA.

Examples of transcriptional modulators or expression activators include but are not limited to: cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-beta, TGF-beta, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Other transgenes suitable for use with the methods and genetically modified ciliates described herein include genes encoding enzymes (e.g., industrial enzymes) or portions thereof. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Other transgenes suitable for use with the methods and genetically modified ciliates described herein include genes encoding vaccine polypeptides, e.g., in polypeptides from infectious fungi, e.g., *Aspergillus, Candida* species; bacteria, particularly *E. coli*, which serves a model for pathogenic bacteria, as well as medically important bacteria such as *Staphylococci* (e.g., *S. aureus*), or *Streptococci* (e.g., *S. pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses, e.g., vaccinia; Picornaviruses, e.g., polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Other transgenes suitable for use with the methods and genetically modified ciliates described herein include genes encoding agriculturally related polypeptides such as insect resistance polypeptides (e.g., the Cry polypeptides), starch and lipid production enzymes, plant and insect toxins, toxin-resistance polypeptides, Mycotoxin detoxification polypeptides, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable target molecules.

Transgenes suitable for use with the methods and genetically modified ciliates described herein include genes encoding can be modified according to any method known in the art to altering one or more therapeutic, diagnostic, or enzymatic properties of the target polypeptide. Examples of therapeutically relevant properties include serum half-life, shelf half-life, stability, immunogenicity, therapeutic activity, detectability (e.g., by the inclusion of reporter groups (e.g., labels or label binding sites)) in the non-natural amino acids, specificity, reduction of LD50 or other side effects, ability to enter the body through the gastric tract (e.g., oral availability), or the like. Examples of relevant diagnostic properties include shelf half-life, stability (including thermostability), diagnostic activity, detectability, specificity, or the like. Examples of relevant enzymatic properties include shelf half-life, stability, specificity, enzymatic activity, production capability, resistance to at least one protease.

EXAMPLES

The following examples illustrate the present invention, and are set forth to aid in the understanding of the invention, and should not be construed to limit in any way the scope of the invention as defined in the claims which follow thereafter.

Example 1

Genetically Modified Ciliates

Genetic instability (e.g., loss of transgenes) in *Tetrahymena* strains containing recombinant rDNA chromosomes can be shown by loss of the transgene polypeptide product and direct visualization of recombination of the recombinant rDNA chromosome (FIG. 1). Genetic instability poses a serious limitation to the use of transgenic *T. thermophila* strains for polypeptide production purposes and would preclude them from use in the production of therapeutic polypeptides. Genetic stability of strains containing transgenes in both 'arms' of the palindrome can be problematic in the presence of rDNA palindromes lacking the insert in 1 or both arms. Once the cell contains only rDNA with inserts in both arms, stability will be relatively complete. In most cases strains created following transformation with an rDNA vector contain a mixture of complete transgenic, hybrid (one arm wild-type and one arm transgene) and wild-type rDNA chromosomes (FIG. 1).

As described herein, the current invention employs genetically distinct and novel *T. thermophila* strains that are genetically modified to be used in conjunction with rDNA based expression vectors leading to the generation of genetically stable recombinant rDNA chromosomes. These genetically modified strains can be useful for the production of a polypeptide of interest from a transgene.

Elements of the polypeptide production system described herein can comprise:

1) A universal recipient cell line optimized for efficient insertion of a cassette containing a given transgene into an rDNA mini-chromosome. The universal recipient line is a homozygous heterokaryon for a lethal micronuclear knock-out of one or more rDNA genes in the rDNA locus)(rDNA$^{KO}$/rDNA$^{KO}$.

Figure 2A:
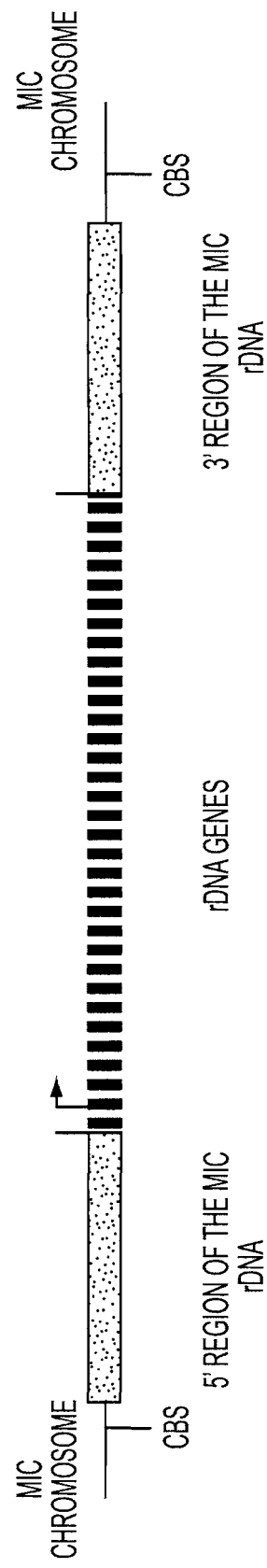
FIG. 2A shows the basic format of the micronuclear (mic) rDNA region. The 5' region includes the origin of replication and the 5' Non-Transcribed Spacer (NTS). Arrow indicates the location of the start of transcription of the rDNA genes. Hatched line indicates the region containing the rDNA genes. The 3' region downstream of the rDNA genes includes the 3' NTS. The chromosome breakage sequences (CBS) which direct the excision of the micronuclear rDNA region during the formation of a new macronucleus are indicated. In several rDNA transformation vectors, a small MCS is inserted near the start of the 3' NTS. Not to scale.
Figure 2B:
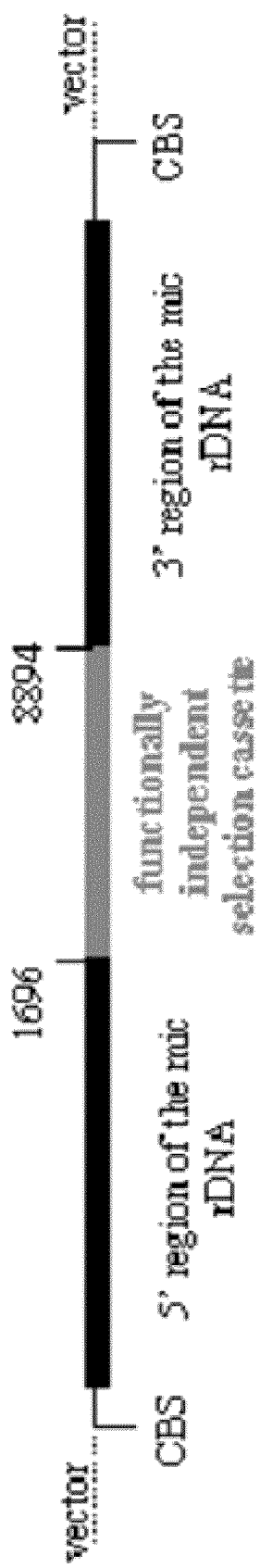
FIG. 2B shows the general organization of a mic rDNA Knockout vector. A functionally independent selection cassette is inserted into a copy of the micronuclear version of the rDNA, replacing much of the central region (in the example shown, all of the rDNA sequence between bases 1696 and 8894 has been removed). The remaining 3' and 5' regions of the micronuclear rDNA, as well adjacent sequence containing the CBS regions, can act as targeting sequences for homologous recombination following transformation. The construct is cloned and maintained in a suitable plasmid vector. Not to scale.
Figure 2C:
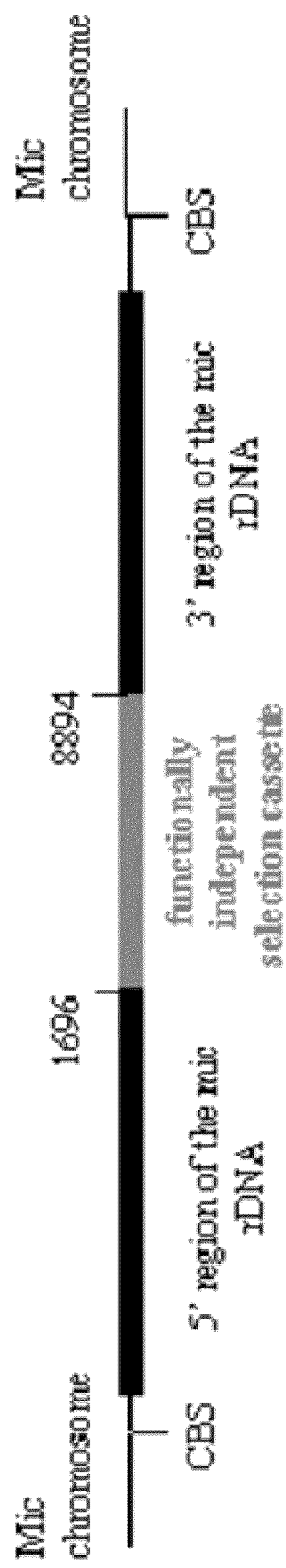
FIG. 2C shows chromosomal organization of the micronuclear rDNA region following successful transformation with the mic Knockout construct. Following homologous double recombination between the vector and the micronuclear chromosome carrying the rDNA genes, the selection cassette is inserted into the micronuclear chromosome, replacing much of the central region (in the example shown all of the rDNA sequence between bases 1696 and 8894) and inactivating the micronuclear rDNA genes. The rest of the mic chromosome is unaffected. Not to scale.
Figure 2D:
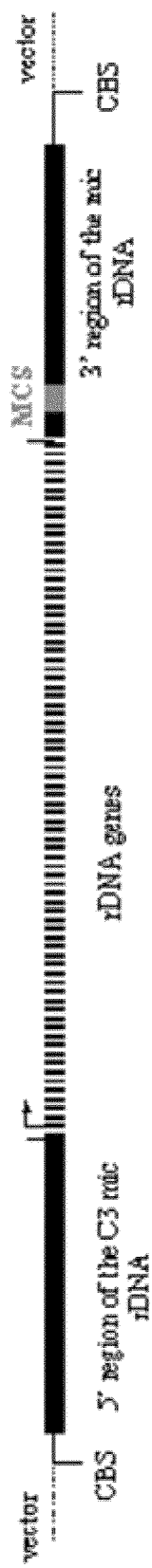
FIG. 2D shows a general macronuclear rDNA transformation vector. The macronuclear transformation vector contains a complete version of the C3 rDNA, including 3' and 5' CBS regions that direct correct processing of the cassette into an rDNA palindrome during macronuclear development. A cassette containing the gene(s) of interest and an independent selection cassette can be inserted into a multiple cloning site (MCS) in the 3' NTS. The construct is cloned and maintained in a suitable plasmid vector. Not to scale.
Figure 2E:
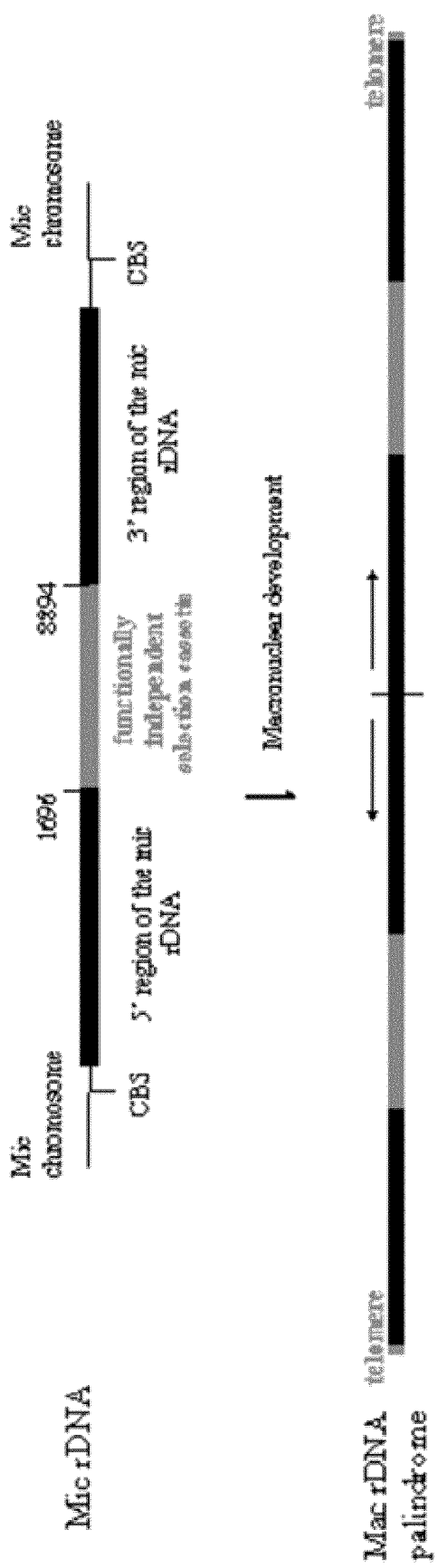
FIG. 2E shows processing of the micronuclear rDNA region transformed with the mic Knockout construct during macronuclear development. The modified micronuclear version of the rDNA is processed into a separate palindromic chromosome as shown.
Figure 2F:
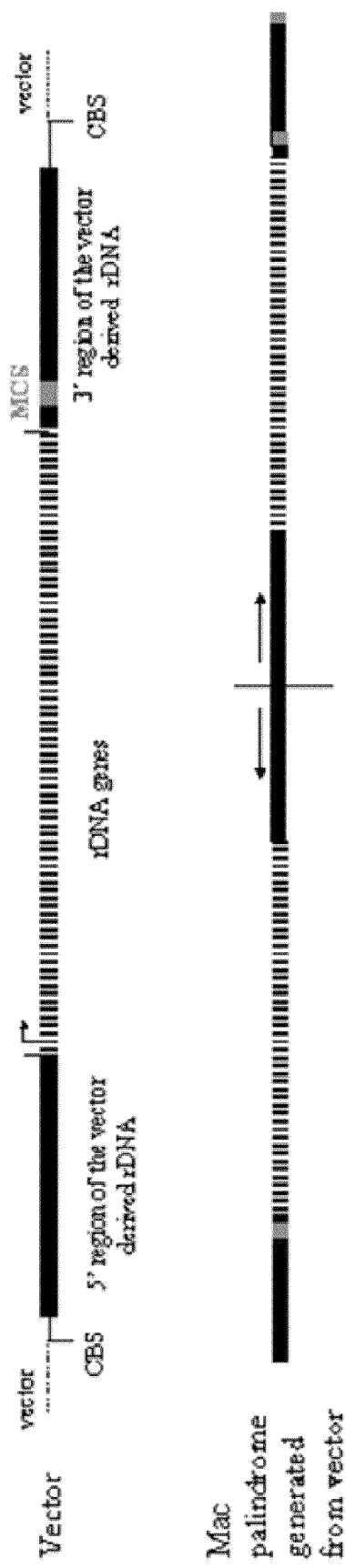
FIG. 2F shows processing of the macronuclear rDNA transformation vector during macronuclear development. The vector rDNA is processed into a separate palindromic chromosome during macronuclear formation as shown.
Figure 2G:
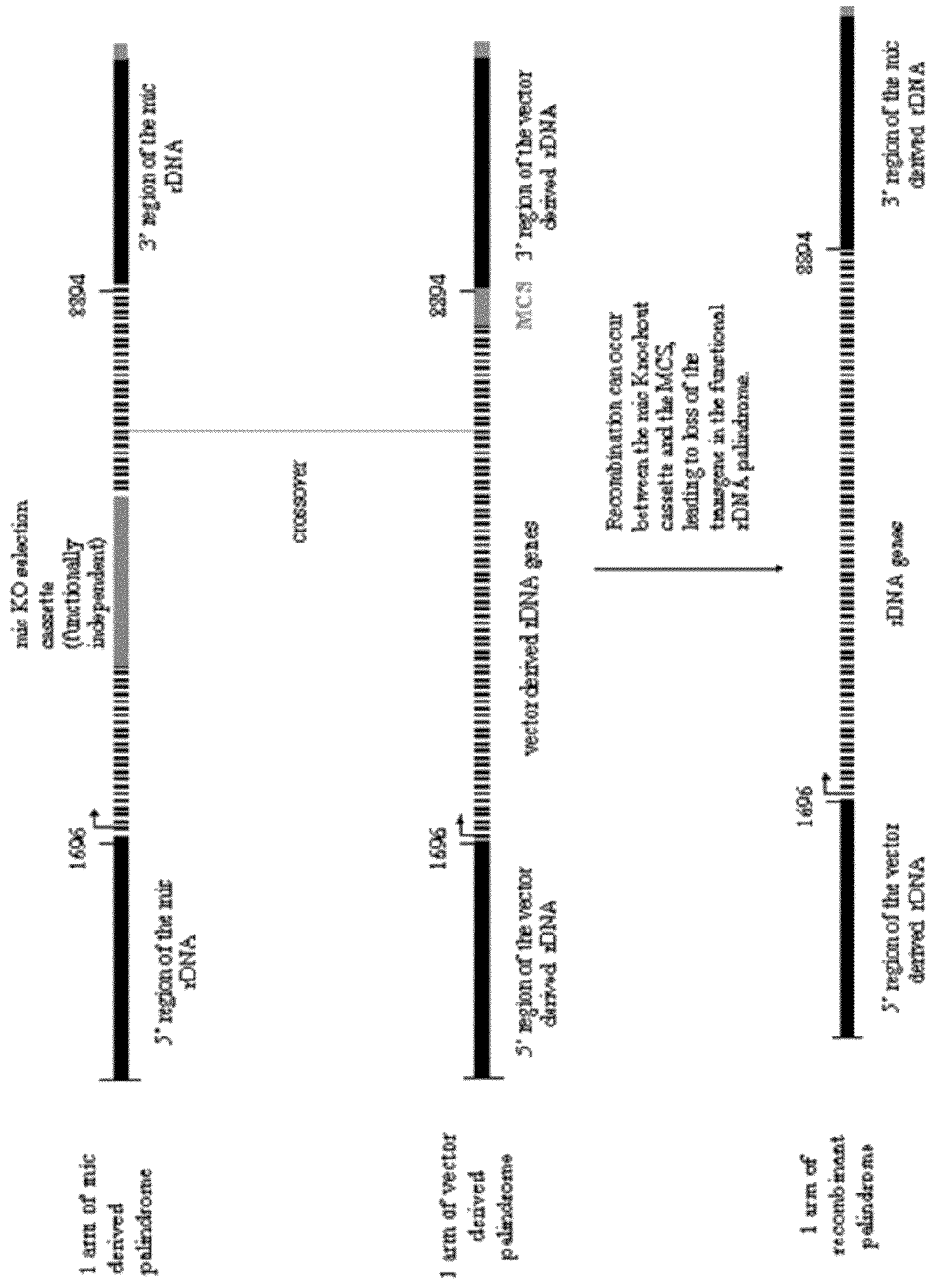
FIG. 2G. Recombination can occur between micronuclear-derived rDNA region and vector-derived rDNA. An example of recombination leading to transgene loss. Recombination resulting in the loss of the transgene carried in the mac transformation vector can occur at various stages during macronuclear development and subsequent cell growth. Recombination is possible between the unprocessed versions prior to palindromic formation during macronuclear development, or between the two palindromic forms following processing of the rDNA region. Loss of the transgene by recombination is possible at any point following successful mac transformation until the micronuclear version is completely lost from the cell. In this example one arm of each of the mic-derived and vector-derived palindromic chromosome is shown. Recombination in the region between the mic selection cassette and the transgene located in the multiple cloning site (MCS) can lead to loss of the transgene when the non-functional mic-derived palindrome is lost from the cell. Both copies of the transgene in the vector-derived palindrome can potentially be lost following intramolecular recombination.
Figure 2H:
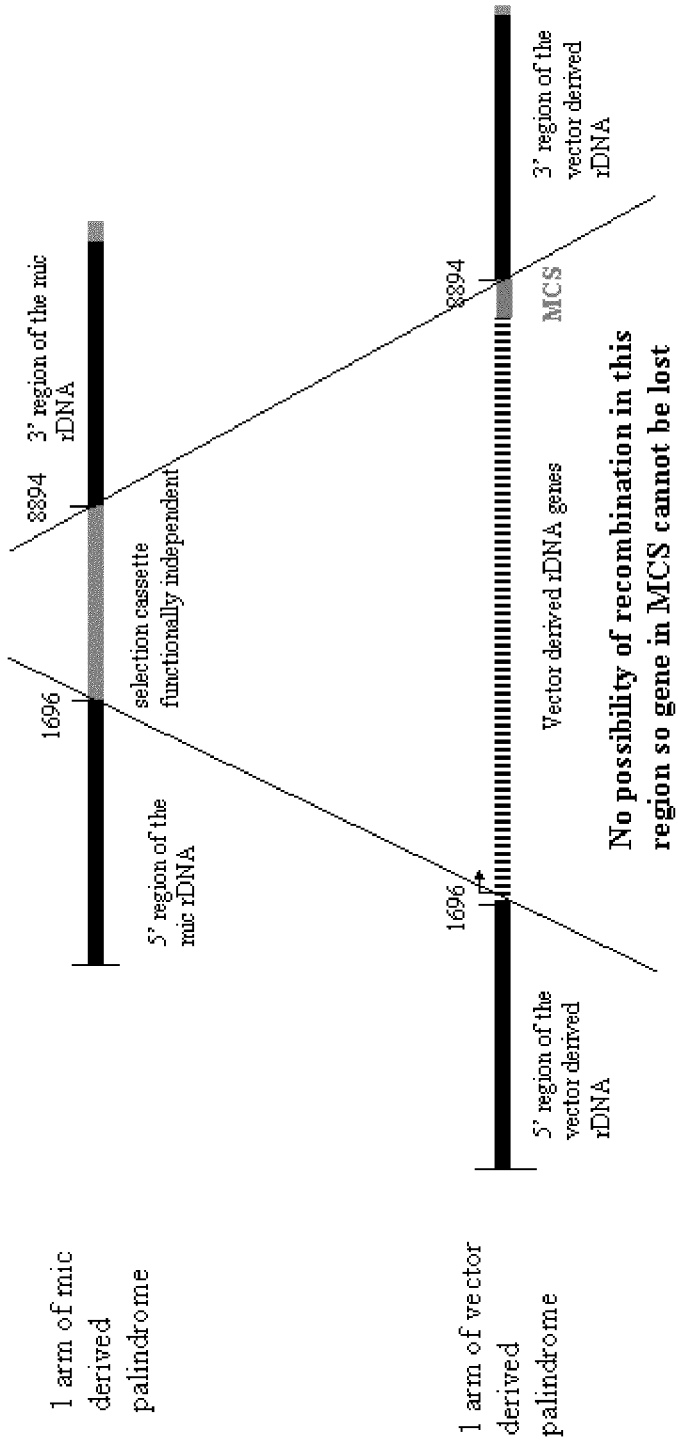
FIG. 2H shows an example of a mic Knockout vector designed to prevent recombinational loss of the transgene. The micronuclear Knockout construct must be engineered to prevent recombinational loss. One example of a micronuclear Knockout vector designed to prevent loss of the transgene following recombination is presented. As in FIG. 2G, one arm of each of the mic-derived and vector-derived palindromic chromosome is shown. Recombination between the two forms downstream of the mic selection cassette, leading to association of the transgene with a non-functional mic-derived palindrome, is prohibited. Recombination in the 5' region will not result in loss of the transgene region.
Figure 3:
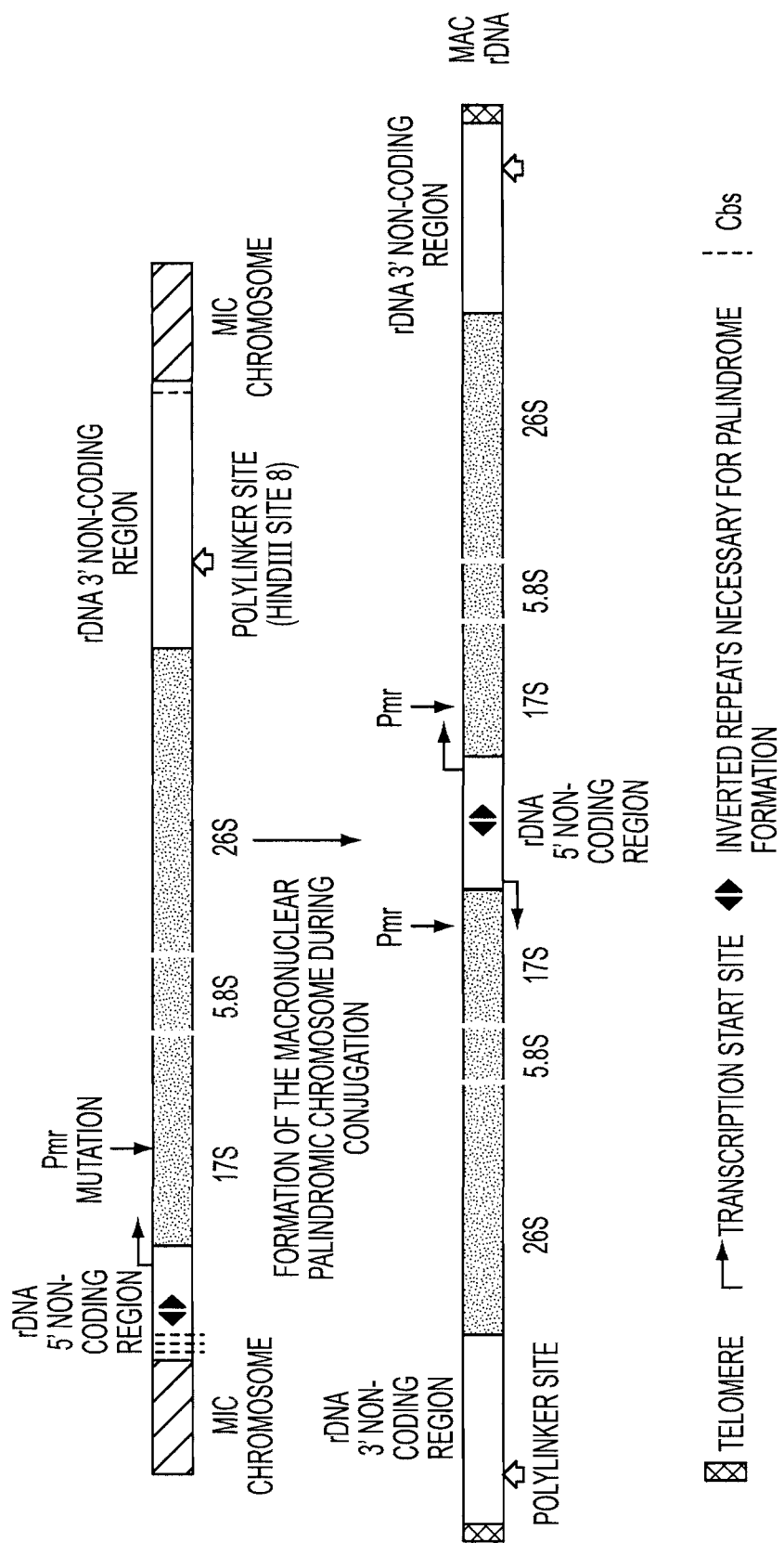
FIG. 3. The *Tetrahymena* rDNA locus and the formation of a palindromic minichromosome upon conjugation. The C3 allele is shown. Upon initiation of sexual reproduction, the micronuclear rDNA locus is removed from the micronuclear germline upon chromosome breakage and undergoes rearrangement into 21 kb head-to-head palindrome bounded by Non-Transcribed Spacers (NTS).

2) An rDNA rescue vector. This vector contains a complete micronuclear rDNA sequence complete with adjacent CBS sequences (see FIG. 2D).

In one embodiment, the replacement insert contains no additional selective marker. Accordingly, rescue of the rDNA KO, with consequent restoration of rDNA expression from a macronuclear rDNA chromosome, is necessary and sufficient for homozygous progeny viability.

A "production cell line" is generated by transformation with the rDNA rescue vector in a cross of two mating types of the universal recipient cell line, followed by selection against cells that have failed to develop a new macronucleus. Only the progeny from the desired transformants will survive as exconjugants.

This system exploits the advantages of high rDNA copy number for increased gene expression. Because the maximum transcription level is potentially very high, it would compensate for the use of a weaker but less toxic promoter than MTT1. Additionally it confers maximum flexibility for adjusting expression levels to below the point at which a particular transgene might reduce growth rate (and could thus select for mutations that knock down gene expression, i.e., instability) during the prolonged growth with the high level of gene expression required in the bioreactor.

The production line is stable because there is essentially no probability of separating the rDNA rescue sequence from the transgene by homologous recombination. It is thus free of the recombination-mediated instability observed for replicative rDNA vectors designed to out-replicate the ever-present endogenous rDNA. The transgene can be lost only through excision by a spontaneous, homology-independent deletion event.

Because the transgene "piggy-backs" on the rDNA rescue segment, the vector provides built-in selection for transgene insertion in generating the production cell line. Thus, even the insertion of a deleterious transgene can be selected for.

The approach allows improvement of production cells lines by the classical, preconception-free approach of shotgun mutagenesis followed by selection or screening for increased production. The desirable mutations can be sought either in the MIC or directly in the MAC.

As described herein, universal recipient lines can be engineered to be homozygous heterokaryons for a knockout of one or more rDNA genes in the micronuclear rDNA locus. These lines can also comprise an extraneous DNA cassette. These cell lines can be genetically pre-engineered in their MIC for any desired features (e.g., appropriate glycosylation). All these elements can be independently developed and then combined by crossing—an advantage of a MIC-based system.

Fertile cell lines of two different mating cells can be used. One of the two cell lines should also be a homozygous heterokaryon for a selective drug resistance marker (e.g., cycloheximide), to as be able to select against cells that failed to differentiate a new macronucleus. The advantage of using only one drug resistant line is that drug resistant homozygote heterokaryons, if/when needed, can be regenerated from the progeny after assortment and a star cross.

Generating Production Cell Lines by Inserting the Transgene into the Universal Recipient Cell Lines.

To insert the transgene, two different mating type versions of universal recipient (UR) cell lines can be crossed to one another and differentiating macronuclei can be transformed with the rescue vector. In the rDNA knockout approach, only the vector derived rDNA will yield a functional rDNA palindromic chromosome in the mac. The mic version may be processed during mac formation but should be rapidly lost during subsequent growth since it contains no functional rDNA and no selectable marker. Only the vector derived rDNA should be maintained in the progeny cells.

Constructing the Universal Recipient Cell Lines with an rDNA KO.

An example of a strategy to generate a micronuclear rDNA knockout strain is shown in Example 4.

MAC-Based Shotgun Mutagenesis Optimization of a Production Cell Line.

Vegetatively growing production cell lines can be mutagenized and can be screened for higher transgene expression. Such screens can be performed using, for example, high throughput Western dot blots or mass spectrometry or any other method suitable for detecting the expression of a gene known in the art.

A MIC-Based Method for Shotgun Optimization of Production Cell Lines.

One or both production cell lines can be mutagenized and crossed to one another in order to perform a classical selection for MIC mutations that boost expression. For example, F1 cells can be grown vegetatively and periodically screened for assortants with high level of expression using, for example, high throughput Western dot blots or mass spectrometry or any other method suitable for detecting the expression of a gene known in the art.

Rescue by Macronuclear Transformation.

Macronuclear transformation can also be used with the methods described in this example. In another embodiment, micronuclear transformation can be used with the methods described in this example. MIC- and MAC-based systems are not mutually exclusive and, can be developed side-by-side.

One consideration associated with rDNA based expression methods is that of the formation of a palindrome following excision and recombination from the vector at the CBS sites. Palindrome formation can be incomplete when recombination with one arm of the wild type sequence gives rise to a hybrid. Subsequent recombination can occur either between hybrids or between hybrid and wild type to form more wild type. Phenotypic assortment gives rise to the various final configurations. In most cases strains contain a mixture of complete transgenic, hybrid (one arm wild-type and one arm transgene) and wild-type rDNA chromosomes upon transformation with an rDNA vector actually (FIG. 1). Strains containing transgenes in both arms of the palindrome are genetically stable whereas strains that contain hybrid rDNA chromosomes (a large percentage of transformants) recombine and revert to a wild-type rDNA palindrome over many generations. Strains containing only palindromic molecules with transgenes in both arms are stable. Strains containing any mix of double transgene, hybrid and wild type molecules are potentially unstable. This re-conversion can result in a loss of the transgene and thus in loss of target polypeptide expression. Viability of progeny resulting from conjugation is conditional upon transformation with a vector encoding the corresponding functional rRNA, and optionally a transgene of interest. Thus, cells which pair (e.g., the first step in conjugation) but do not subsequently undergo the complete process of mating before becoming committed, or cells which separate after aborting the differentiation of new macronuclei (and keeping the parental macronucleus), are not affected and can survive conjugation.

Example 2

Exemplary Protocol for Generating a Universal Recipient Cell Line Lacking a Functional Micronuclear rDNA Locus (rDNA Knockout Strains)

A summary of this protocol is shown in Example 4.

Described in this example is the generation of a *T. thermophila* strain that contains a mutation in the rDNA locus such that one or more rRNA encoding genes in the micronuclear rDNA locus are non functional (e.g. knocked out). This strain will ensure that only rDNA derived form the transformation vector is present in the MAC following transformation. (since only successful transformants will survive). Strains deficient in the rDNA will be transformed in the macronucleus with a novel vector that contains the transgene and the complete rDNA. Subsequent maintenance of recombinant rDNA chromosomes is ensured since only the sexual progeny resulting from successful transformation will survive.

This method has the advantages that (1) it can ensure genetic stability of strains, and (2) the cell lines are stably transformed, thereby enabling selection of cell lines that carry the transgene by mutagenizing the MAC.

As used herein "Mpr" refers to 6-methylpurine resistance, "Mps" refers to 6-methylpurine susceptibility, "Pmr" refers to paromomycin resistance and "Pms" refers to susceptibility.

Parent strains:
(1) CU428 Mpr/Mpr (mps, VII) and homozygous for mutation conferring resistance to 6-methylpurine in micronucleus. They are sensitive to 6-methylpurine (6 mp) in macronucleus. Mating type VII. The 6 mp will be necessary for the subsequent macronuclear transformation with rescue vector.

(2) B2086 Mps/Mps (mps, MT II) (mps is needed to allow assortment of macronuclear in progeny). Wild type strain. Mating type II.

Vector:

Plasmid containing the rDNA$^{KO}$ construct with paromomycin (Pmr) selectable marker cassette plus appropriate flanking targeting sequences.

Mate:

CU428×B2086 and Transform (biolistic) at crescent stage of conjugation 3.5-4.5 hours after initial pairing (temperature dependent). Allow cells to complete conjugation. Parents are: Mpr/Mpr (mps, VII); Mps/Mps (mps, MT II)

Progeny:

(1) transformed [Mpr/Mps, rDNA$^{WT}$/rDNA$^{KO}$pmr (mpr, pmr)], and (2) non-transformed [Mpr/Mps, rDNA$^{WT}$/rDNA$^{WT}$ (mpr, pms)]. Select with paromomycin to identify transformants. Replicate pmr clones into 6-mp and select with 6-methylpurine to eliminate vegetative transformants (not progeny). Save pmr, mpr clones. Serial transfer in absence of drugs at 2 temperatures. The critical period during which temperature affects mating type frequencies is during MAC differentiation.

Another factor is early (before 9 hr) vs. late (~24 hr) re-feeding (after mixing cells to start the cross at 35° C.). Early re-feeding and high temperature work in tandem to increase mt IV, while the opposite conditions decrease it and increase other mating types.

Two conditions can be used [(1) re-feeding before 9 hours in a 35° C. cross, and (2) re-feeding at 48 hrs in a 25° C. cross] to mature clones to different mating types and phenotypically assort macronuclei to pms and mps. Test phenotypic assortment. This produces clones that are Mpr/Mps, rDNA$^{WT}$/rDNApmr (mps, pms) in different mating types.

Mate mature clones to "star" line lacking functional micronucleus and isolate mating pairs (RdI pairs) and individual ex-conjugants for each pair. This mating creates 100% homozygous micronuclei in each mating pair and aborts prior to the formation of a new macronucleus. The resultant pairs will represent all 4 of the meiotic products from the parent micronucleus:

Mpr/Mpr, rDNA$^{WT}$/rDNA$^{WT}$ (mps, pms)
Mps/Mps, rDNA$^{WT}$/rDNA$^{WT}$ (mps, pms)
Mps/Mps, rDNA$^{KO}$pmr/rDNA$^{KO}$pmr (mps, pms)
Mpr/Mpr, rDNA$^{KO}$pmr/rDNA$^{KO}$pmr (mps, pms)

Grow exconjugants. Starve and mate exconjugants from each individual pair (RdII mating) to bring micronuclei into expression. This mating can be a test cross (e.g. to a cycloheximide heterokaryon) to identify which exconjugants are homozygous in their MIC for Mpr and the rDNA$^{KO}$pmr. Mating strains that both carry the rDNA$^{KO}$ will be lethal.

Wait 24 hours for mating to be completed. Re-feed.

Replicate to paromomycin to select for KO construct in RdI micronucleus and from paromomycin to 6-methylpurine to identify those RdI micronuclei also homozygous for Mpr. From the RdI clones identified as homozygous in the micronucleus for the rDNA$^{KO}$ and Mpr by the phenotype of the RdII macronucleus, select the non-star exconjugate identified by mating type.

Save at least 2 different mating types.

Example 3

Micronuclear Knockout Vector

There are several considerations that can be important for the design of the micronuclear rDNA knockout vector (see FIGS. 2, 3, 4 and 5). These can include, but are not limited to: (1) CBS function at both 3' and 5' sites should not be impaired because initial micronuclear selection must be based on macronuclear expression, (2) the replication fork barrier (RFB) located near the start of the 5' NTS should be maintained in the micronucleus following knockout to prevent destabilization of micronuclear chromosome 1 (this is important for future use of strain), (3) the 5' region of rDNA, which is required for palindrome replication, should be retained in the micronuclear KO vector construct to permit maintenance and selection in the new transformant macronucleus, (4) the 3' rDNA sequence in the micronuclear KO construct must be distal to the MCS site in the 3' NTS to prevent possibility of loss of the transgene by recombination during or after anlagen development (this is possible because there are about 1500 bp downstream of that site which can be used for targeting), and (5) the sites previously shown to give functional palindrome formation and lower copy number (300 copies on average) can be used to provide selection against fewer copies of the micronuclear version.

Figure 5:
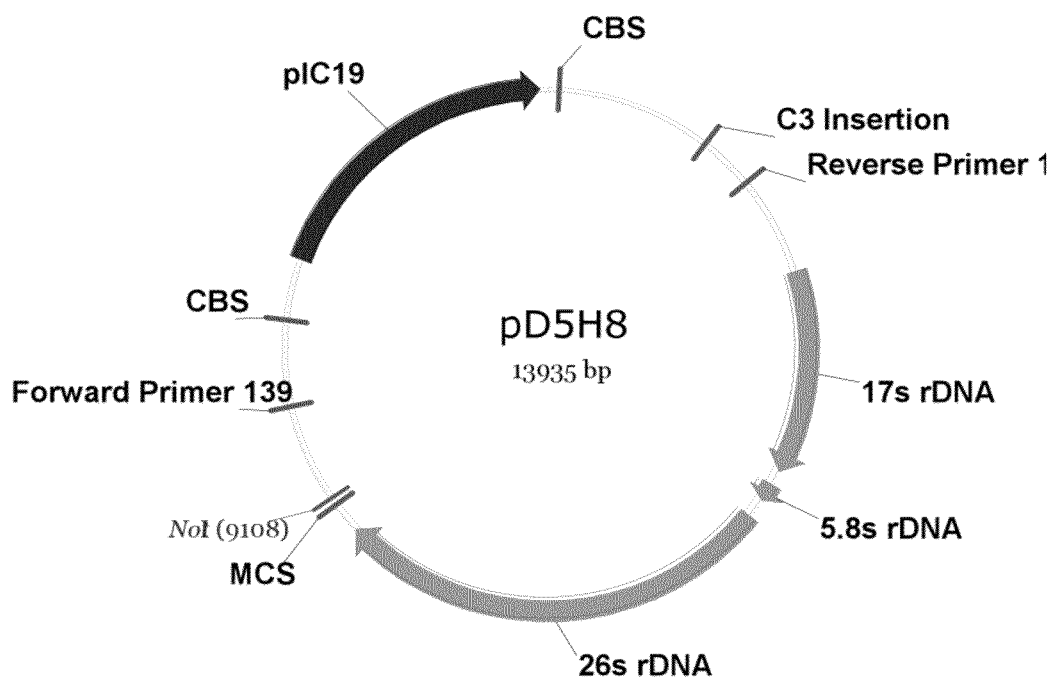
FIG. 5. pD5H8 Vector. Shown is the position of forward and reverse primers used to amplify the knockout fragment. Also shown are the positions of the rDNA 17S, 5.8S and 26S genes. CBS, chromosome breakage sites; MCS, multiple cloning site.

As shown in FIGS. 4 and 5, the pD5H8 vector has an overall size of about 13935 base pairs. The rDNA gene sequences are located between positions 200-10683 in the sequence as shown.

Deletion of these sequences can make the vector shorter and more amenable for transformation. Another advantage of using this flanking region is that the shorter construct gives on average 370 copies of rDNA upon macronuclear transformation whereas constructs with a longer flanking region result in up to 10,000 copies of the construct. This reduction in copy number enables better selectability for a resistance marker.

The micronuclear knockout cassette can be placed between positions 5742 and 12940 of pD5H8. Doing so (1) fulfills the requirements for processing and palindrome formation at the 5' end, (2) does not disturb the Replication Fork Barrier (RFB) such that micronuclear chromosome 1 stability is unaffected, (3) loss of the gene of interest by recombination with any remaining KO construct from the micronucleus is prevented, (4) at least 1500 bases are provided for targeting the transformation, (5) expression of the micronuclear version is enabled for selection purposes but the number of micronucleus derived palindromes made in the new macronucleus is minimized (300 or so from studies of macronuclear transformation with similar construct vs. 10,000), (6) increasing the speed with which the construct is lost in developing nuclei when selection is not present minimizing the expenditure of resources (by not causing the cell to make something that is not needed for cell survival.

Deletion of the 5' flank should proceed upstream beyond 1646 bp to avoid destabilizing micronuclear chromosome 1, since it has been shown that further removal of the upstream region causes fragmentation of the entire micronuclear chromosome 1 (Yakisch and Kapler, 2006). However, the 5' flank could be extended downstream into the 17S if desired. Limiting the 5' flanking region to between bases 1646-2412 in the rDNA bases 5742-6458 in pD5H8 sequence) decreases the number of copies of the defective micronuclear palindrome made during conjugation but still ensures that sufficient copies are produced to allow macronuclear expression of the selection cassette present in the micronuclear knockout cassette. Using the 1646 bp site makes for a slightly shorter transformation vector for micronuclear knockout. The region between 1646 and 8261 can be deleted and still give sufficient palindrome formation and not affect the stability of micronuclear chromosome 1 (Blomberg et al. (1997)).

As described herein, extending the length of the 3' retained region is an option but will give higher copy number of the mic version following conjugation.

Example 4

Generation of Micronuclear rDNA Knockout

Parent Strains:
CU428 Mpr/Mpr (mps, VII)
Homozygous for mutation conferring resistance to 6-methylpurine in micronucleus. Sensitive to 6-methylpurine (6 mp) in macronucleus. Mating type VII. The 6 mp will be necessary for the subsequent mac transformation with rescue vector.
B2086 Mps/Mps (mps, MT II)
Wild type strain. Mating type II.
Vector:
Plasmid containing either the CBS KO construct or the rDNA KO construct with paromomycin (Pmr) selectable marker cassette plus appropriate flanking targeting sequences.
Mate: CU428×B2086
Transform (biolistic) at crescent stage of conjugation 3.5-4.5 hours after initial pairing (temperature dependent).
Allow cells to complete conjugation.
Parents: Mpr/Mpr (mps, VII); Mps/Mps (mps, MT II)
Progeny: transformed Mpr/Mps, rDNA/KOpmr (mpr, pmr)
non-transformed: Mpr/Mps, rDNA/rDNA (mpr, pms)
Select with paromomycin to identify transformants. Carry out all initial treatments at different temperatures to generate different mating types.
Replicate pmr clones into 6-mp and select with 6-methylpurine to eliminate vegetative transformants (not progeny).
Save pmr, mpr clones. Serial transfer in absence of drugs at different temperatures to mature clones and to phenotypically assort macs to pms and mps. This produces clones that are Mpr/Mps, rDNA/KOpmr (mps, pms) in different mating types.
Mate mature clones to "star" line lacking functional micronucleus and isolate mating pairs (RdI pairs) and individual ex-conjugants for each pair. This mating creates 100% homozygous micronuclei in each mating pair and aborts prior to the formation of a new mac. The resultant pairs will represent all 4 of the meiotic products from the parent mic. The 25% of the clones shown in red are the desired genotype and phenotype. These clones can be identified by doing a second round of mating (RdII—essentially a self mating) and isolating individual RdII pairs form each RdI clone. Homozygous KO lines will not produce viable RdII progeny. Mpr phenotype can be determined by outcrossed to a diploid wild type strain (outcross to a diploid will produce viable progeny), and testing for methylpurine resistance.
Mpr/Mpr, rDNA/rDNA (mps, pms)
Mps/Mps, rDNA/rDNA (mps, pms)
Mps/Mps, KOpmr/KOpmr (mps, pms)
Mpr/Mpr, KOpmr/KOpmr (mps, pms)

Example 5 rDNA KO *Tetrahymena* Spp. Strains

Materials.
*Tetrahymena* cells will be cultured in NEFF medium (0.25% proteose peptone, 0.25% yeast extract, 0.55% glucose, 33 mM $FeCl_3$) supplemented, when required, with paromomycin at a final concentration of 100 mg/ml. All medium components can be acquired from VWR. Restriction enzymes used in cloning and Phusion polymerase for PCR can be purchased from New England Biolabs. Electrocompetent *Escherichia coli* Top 10 can be purchased from Invitrogen. For Biolistic transformations DNAdel™ S550d gold carrier particle suspension can be purchased from Seashell Technology and filter paper from Whatman.

Methods: Construction of an rDNA Knockout (KO) Vector.

Figure 6:
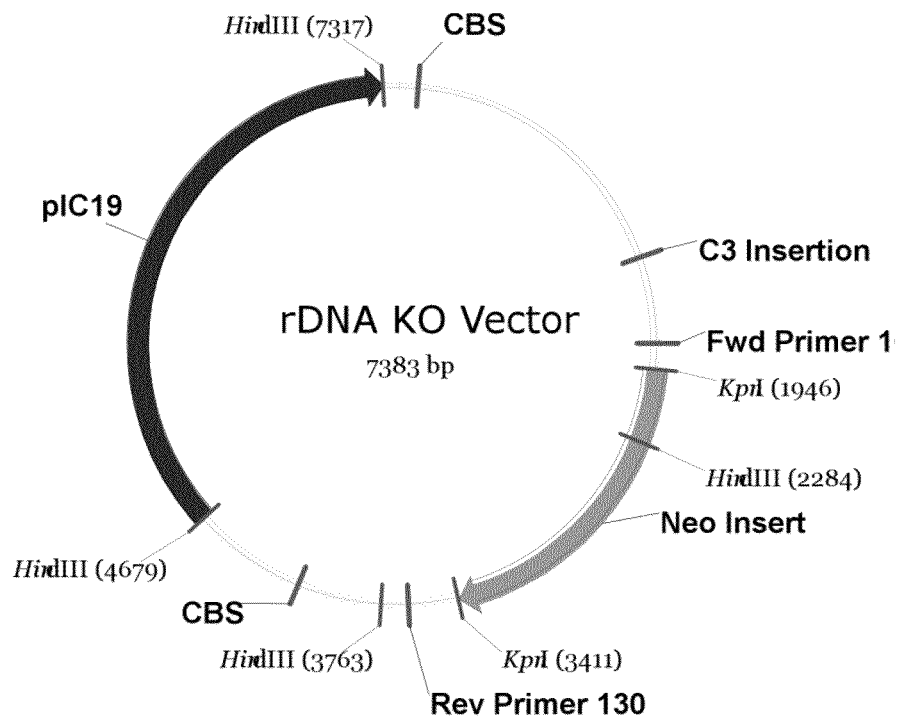
FIG. 6. rDNA knockout (KO) vector. Shown is the placement of the Neomycin resistance cassette (Neo insert) and the relative positions of forward and reverse diagnostic primer annealing sites.

To create the backbone of the rDNA KO vector, forward (5'-TTAGGTACCACCAAACCAAAAGACCTAA) (SEQ ID NO: 4) and reverse (5'-TTAGGTACCTATTTTCACTAAGTCTAATTTAATTTAG) (SEQ ID NO: 5) primers will be used to amplify all of rDNA vector pD5H8 except that portion which contains the 17s, 5.8s and 26s rDNA sequences but while maintaining the chromosomal breakage sites (CBS) and the ability to form a functional palindrome (FIG. 6). Both primers will contain KpnI sites that are incorporated into both ends of the amplified product. The 5,924 bp product will be digested with KpnI, gel purified away from the rDNA portion of the vector and dephosphorylated. Amplification of the neomycin resistance gene cassette will be performed using forward (5'-TTAGGTACCATCTTCAAAGTATGGATTAATTATTTC) (SEQ ID NO: 6) and reverse (5'-TTAGGTACCCTGCATTTTTCCAGTAAAAAT) (SEQ ID NO: 7) primers using vector pTIEV4 as template. Amplification of the neomycin resistance cassette will result in a 1,477 bp DNA fragment with KpnI restriction sites at both the 5' and 3' ends. This product will be gel purified then digested with KpnI. The neomycin resistance cassette insert will be ligated into the digested backbone and the ligation will be transformed into Top 10 *E. coli*. Ampicillin resistant colonies will be screened by colony PCR using forward primer (5'-ATGAAGCAGACTCGCTTAAAAATG) (SEQ ID NO: 8) and reverse primer (5'-ATTTTTGCATCAATTTCCACTTA) (SEQ ID NO: 9). Plasmid DNA will be purified from colonies that show amplification of a 1,830 bp product. Plasmid DNA will then be sent for complete sequencing using a set of primers designed to anneal about every 500 base pairs to ensure there were no additional mutations and confirm construction of the rDNA knockout vector (FIG. 7).

Generation of an rDNA KO *Tetrahymena* Strain.

Germ line biolistic transformation of conjugating *Tetrahymena thermophila* cells will be performed in the following way; B2086 and CU428 *T. thermophila* strains will be grown in modified NEFF medium (0.25% proteose peptone, 0.25% yeast extract, 0.55% glucose, 33 mM $FeCl_3$) at 30° C. One hundred ml of each logarithmically growing culture will be centrifuged at 1,100×g for 2 minutes in oil centrifuge tubes, washed in 10 mM Tris pH 7.4 and resuspended in fresh 10 mM Tris pH 7.4 (starvation medium) at a concentration of 200,000-250,000 cells/ml. Cells will be incubated for 9-18 hours at 30° C. After starvation, B2086 and CU428 cell cultures will be counted and cell concentration will be readjusted to 200,000 cells/ml. To induce conjugation, 100 ml of each strain will be mixed together in a 4 L flask and incubated for 30 minutes at 30° C. An on/off shaking method will be used to ensure synchronous pairing in the following way; after a 30 minute stationary incubation, the cells in the flask will be subjected to shaking (100 rpm) for 30 minutes. The shaker will be stopped for 15 minutes and then turned back on again for 15 minutes. The last time the shaker is stopped will be counted as the start of mating (0 hours post-mixing), since cell pairing is inhibited by shaking.

Four transformations will be performed at 2.5, 3, 3.5 and 4 hours post-mixing using Biolistic PDS-1000/He Particle Delivery System (BIO-RAD). For each transformation, 30 µl of DNAdel™ S550d gold carrier particle suspension (Seashell Technology) will be coated with 4 µg of linearized rDNA KO construct according to the manufacturer's instructions. 50 ml of conjugating cells are concentrated to ~1 ml by centrifugation at 1,100×g in oil centrifuge tubes for 2 minutes. Cells will be spread on a round 90 mm hardened paper filter (Whatman, Cat. #1450-090) pre-wet with 1.5 ml 10 mM Tris pH 7.4 inside a Petri dish. After the bombardment, the filter with the cells will be transferred into a 500 ml flask containing 50 ml 10 mM Tris pH 7.4. The flasks will be incubated overnight on a slow shaker at 30° C. At 18 hours post-mixing, 25 ml 3×NEFF medium will be added to the 50 ml of cell culture. At 28 hours post-mixing, 75 µl 100 mg/ml paromomycin will be added (final paromomycin concentration, 100 µg/ml). Cells will be aliquoted into 96 well microplates (150 µl per well). After 3-4 days, the microplates will be examined and 5 µl from each of the wells containing paromomycin-resistant cells will be transferred into 150 µl NEFF medium containing 15 µg/ml 6-methylpurine (Sigma) on a 96 well microplate. At least one well containing the cells resistant to both paromomycin and 6-methylpurine will be identified. Twelve single cells will be isolated from this well into 12 small drops of NEFF medium on a Petri dish. After the cells divide and form colonies in the drops, 12 single cell colonies will be transferred onto a 96 well microplate containing NEFF medium. These single cell clones will be grown in NEFF medium for 10 days (1 µl of the cells was transferred into 150 µl of NEFF medium every day). After the cells become sexually mature (~60 cell fissions), they will be starved in 10 mM Tris pH 7.4 and mixed in different combinations to select 2 strains of different mating types. Approximately 100 single cells will be isolated from each of the two strains of different mating types into drops of NEFF medium. 2 days later, the cells will be transferred to a NEFF medium on a 96 well microplate and then replica plated to NEFF medium containing 100 µg/ml paromomycin. Single cell clones of two different mating types that assort to paromomycin-sensitive phenotype will be tested for Mendelian segregation: cells will be starved and mated with starved CU427 cells, which are homozygous for a cycloheximide resistance marker. Approximately 100 single pairs from this mating will be isolated at 10 hours post-mixing into drops of NEFF media. After the conjugation is completed and the progeny have given rise to cell colonies, the cells will be transferred into NEFF media containing 15 µg/ml cycloheximide on a 96 well microplate and, a day later, they will be replica plated from the cycloheximide to paromomycin (100 µg/ml in NEFF). The number of paromomycin-resistant colonies will be about half of that of cycloheximide-resistant colonies, which will confirm that the rDNA KO strains obtained are indeed germ line transformants.

Round I genomic exclusion will be performed to make homozygous rDNA knock-out heterokaryons. Each of the two heterozygous rDNA KO strains of different mating types will be starved and mated to "star" strain B*VI. Approximately 50 single pairs will be isolated from each mating at 5 hours post-mixing into NEFF medium drops. When some of the pairs separate (~10 hours post-mixing), the two cells from each separated pair will be isolated into two different drops. The Petri dishes with the NEFF medium drops will be incubated for two days to allow Round I products to divide several times. The single cell colonies will be then transferred into microtiter plates containing NEFF medium. To distinguish between the "star" and "non-star" sides of each pair of Round I exconjugants, the cells will be replica plated to NEFF medium containing 15 µg/ml 6-methylpurine. The 6-methylpurine resistant cells will be marked as "non-star" sides, since they will be derived from the germ line transformants and not from the B*VI strain. The "non-star" Round I exconjugants homozygous for rDNA knock-out in the micronucleus will be identified by mating to CU427 as described above in the Mendelian segregation test. One hundred percent of the cycloheximide-resistant progeny from the CU427 mating will be paromomycin-resistant if the Round I exconjugants were homozygous for rDNA knock-out. The "non-star" exconjugants of Round I mating that meet this requirement will be identified as homozygous rDNA knock-out heterokaryons.

Results.

To confirm that pD5H8 vector, which contains genes encoding for ribosomal RNA, can be utilized to introduce rDNA into the progeny of the homozygous rDNA knock-outs, it will be transformed into developing new macronuclei of the conjugating homozygous rDNA knock-outs. One hundred ml of each of the two homozygous rDNA knock-outs of different mating types will be grown, starved and mated as described above. Four biolistic transformations will be performed as described above between 9.5 and 10.5 hours post-mixing. For each transformation, 30 µl of DNAdel™ S550d gold carrier particle suspension are coated with 4 µg of pD5H8 vector according to manufacturer's instructions. After the bombardment, the filter with the cells will be transferred into a 500 ml flask containing 50 ml NEFF. The flasks are incubated on a slow shaker for ~20 hours at 30° C. At ~30 hours post-mixing, 25 ml NEFF medium containing 300 µg/mlparomomycin will be added to the 50 ml of cell culture (final paromomycin concentration, 100 µg/ml). Cells will be aliquoted into 96 well microplates (150 µl per well). After 3-4 days, the microplates will be examined to identify paromomycin-resistant cells confirming complementation of the null rDNA alleles in the homozygous knockout strain with the pD5H8 derived rDNA genes.

Example 6

Creation of the Paromomycin-Sensitive rDNA Vector pTRAS

Materials.

*Tetrahymena* cells were cultured in NEFF medium (0.25% proteose peptone, 0.25% yeast extract, 0.55% glucose, 33 mM FeCl$_3$) supplemented, when required, with paromomycin at a final concentration of 100 mg/ml. All medium components were acquired from VWR. Restriction enzymes used in cloning and Phusion polymerase for PCR were purchased from New England Biolabs. Electrocompetent *Escherichia coli* Top 10 were purchased from Invitrogen. For Biolistic transformations DNAdel™ S550d gold carrier particle suspension was purchased from Seashell Technology and filter paper from Whatman.

Methods. Construction of an rDNA Vector Containing a Wild-Type 17S rDNA Gene: pTRAS.

Figure 8:
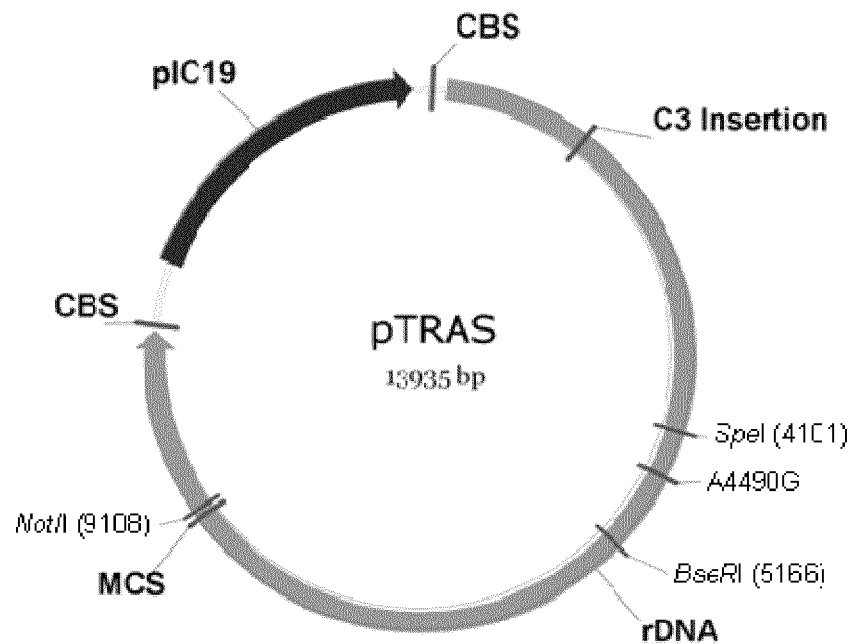
FIG. 8. pTRAS vector. Highlighted are the SpeI, BseRI restriction sites used in construction of pTRAS and the NotI restriction site used for introduction of transgene expression cassettes. Note, numbering for restriction enzymes reflects position of site in the vector. CBS, chromosome breakage sites; MCS, multiple cloning site; A4490G (rDNA gene numbering), position of reverted 17S rDNA mutation.

The reversion of the rDNA vector pD5H8 from the mutant paromomycin resistant form to the wild-type paromomycin sensitive form (17S rDNA; A4490G) was performed by site-directed mutagenesis with overlap extension (SOEing) PCR. Amplification of the 410 bp upstream segment was performed using pD5H8 plasmid as template DNA with the primer pair TR-WTF1 (5'-TTCCGTTAACGAACGAGACCT) (SEQ ID NO: 10) and TR-WTR2 (5'-AGATACCTTGTTACGACT-TCTTGTTGTTCCAAATGGTAG) (SEQ ID NO: 11). Primer TR-WTR2 incorporates the A to G reversion and the PCR product contains an endogenous upstream SpeI restriction site. Amplification of the 1173 bp downstream segment was performed from pD5H8 plasmid DNA with the TR-WTF2 (5'-CTACCATTTGGAACAACAAGAAGTCG-TAACAAGGTATCT) (SEQ ID NO: 17) and TR-WTR1 (5'-GACTCCTTCAATCTGAACCCA) (SEQ ID NO: 18) primer pair. TR-WTR2 also incorporates the A to G reversion and the PCR product contains an endogenous downstream BseRI site. These two amplification products were then used as the template in a SOEing PCR with TR-WTF1 and TR-WTR1 resulting in a 1496 bp product. This amplified product was digested using SpeI and BseRI restriction enzymes and gel purified resulting in a 1065 bp DNA fragment that contains the A to G reversion. pD5H8 plasmid was also digested with SpeI and BseRI and the 12,870 by piece gel purified. These two DNA fragments were ligated together and transformed into E. coli. Plasmids were purified from multiple colonies and sequencing was used to confirm the A to G reversion and ensure no additional mutations had occurred (FIG. 7). The final construct was named pTRAS (Tetragenetics rDNA Antibiotic Sensitive) and is shown in FIG. 8.

Construction of a pTRAS Vector Containing a Neomycin Resistance Gene Marker.

Figure 9:
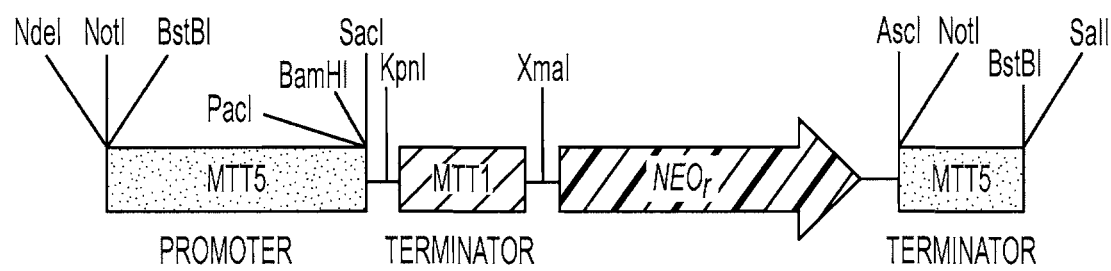
FIG. 9. pTIEV4 vector. Neo$_r$, neomycin resistance gene marker.

To confirm the ability of the new pTRAS vector to restore paromomycin resistance using a transgene cassette, an expression cassette containing a neomycin resistance marker gene was cloned into the pTRAS vector. The source of the neomycin resistance marker gene was from the somatic integration vector pTIEV4 (FIG. 9). This vector is routinely used to create expression cassettes that place transgenes under the control of the powerful Tetrahymena MTT5 inducible promoter and that are subcloned into an rDNA vector (e.g. pD5H8) for introduction and high-level expression in Tetrahymena. A pTIEV4 derived NotI fragment (4307 bp) consisting of the MTT5 promoter, transgene, MTT1 terminator, neomycin resistance marker gene and the MTT5 terminator sequence was ligated into the NotI restriction site of either pTRAS or pD5H8. NotI is a unique restriction site in both pD5H8 and pTRAS. For the purposes of this experiment the transgene incorporated into the expression cassette was a previously cloned Tetrahymena codon optimized gene encoding the human G-protein coupled receptor, CCR5. The use of this transgene was arbitrary and was only used for the purposes of this example. This ligation was transformed into E. coli and individual colonies were screened for the presence of insert by colony PCR using forward (5'-CTTGAATACAAT-CATGAGTTCACC) (SEQ ID NO: 12) and reverse (5'-GCAATTATGAATTACAACATCAACA) (SEQ ID NO: 13) primers. Plasmids were then purified from colonies that amplified the appropriate 1350 bp product. Additionally these plasmids were digested with NotI to excise the transgene insert and confirm its presence.

Transformation of Tetrahymena Cells with pD5H8, pTRAS and pTRAS+Neomycin Resistance Gene Marker.

To prepare DNA for biolistic transformation into conjugating Tetrahymena strains, Escherichia coli Top 10 strains carrying plasmids pTRAS, pD5H8 and pTRAS+neomycin resistance gene marker were cultured in 25 ml Luria-Bertani (LB) broth supplemented with ampicillin (100 μg/ml). Plasmids were prepared using the HiSpeed Plasmid Midi Kit (Qiagen Cat No. 12643) according to manufacturer's instructions then concentrated to 1.5-2 μg/μl by ethanol precipitation. B2086 and CU428 T. thermophila strains were grown in modified NEFF medium (0.25% proteose peptone, 0.25% yeast extract, 0.55% glucose, 33 mM FeCl$_3$) at 30° C. One hundred ml of each logarithmically growing culture was centrifuged at 1,100×g for 2 minutes in oil centrifuge tubes, washed in 10 mM Tris pH 7.4 and resuspended in fresh 10 mM Tris pH 7.4 (starvation medium) at a concentration of 200,000-250,000 cells/ml. Cells were incubated for 9-18 hours at 30° C. After starvation, B2086 and CU428 cell cultures were counted and cell concentration was readjusted to 200,000 cells/ml. To induce conjugation, 100 ml of each strain were mixed together in a 4 L flask. Four transformations were performed between 9.5 and 10.5 hours post-mixing using a Biolistic PDS-1000/He Particle Delivery System (BIO-RAD). For each transformation, 20 μl of DNAdel™ S550d gold carrier particle suspension were coated with 4 μg of DNA construct according to manufacturer's instructions. Fifty ml of conjugating cells were concentrated to ~1 ml by centrifugation at 1,100×g in oil centrifuge tubes for 2 minutes. Cells were spread on a round 90 mm hardened paper filter (Whatman) pre-wet with 1.5 ml 10 mM Tris pH 7.4 inside a Petri dish. After the bombardment, the filter with the cells was transferred into a 500 ml flask containing 50 ml NEFF medium. The flasks were incubated on a slow shaker for ~20 hours at 30° C. At 30 hours post-mixing, 25 ml NEFF medium containing 300 μg/ml paromomycin was added to the 50 ml of cell culture (final paromomycin concentration, 100 μg/ml). Cells were aliquoted into 96 well microplates (150 μl per well). After 3-4 days, the microplates were examined and 5 μl from each of the wells containing paromomycin-resistant cells were transferred into 150 μl NEFF medium containing 100 μg/ml paromomycin on a master 96 well microplate.

Results.

To verify the paromomycin sensitivity of the pTRAS vector it was biolistically transformed into conjugating Tetrahymena cells. As controls, pD5H8 and pTRAS+neomycin resistance gene marker were transformed into the same batch of conjugating cells. Since pD5H8 has the 17S rDNA gene point mutation A4490G, it should survive biolistic transformation followed by selection with paromomycin. However, pTRAS should not survive the neomycin selection because the A4490G mutation has been reverted back to the wild-type gene rendering strains carrying this plasmid paromomycin sensitive. Lastly, the insertion of an expression cassette containing a neomycin resistance marker gene should restore neomycin resistance to the pTRAS vector and transformants should be recovered with paromomycin selection after biolistic transformation. Biolistic transformations were performed in triplicate and the results are summarized in Table 1. In each case, cells transformed with pD5H8 led to the recovery of paromomycin resistance clones. However, paromomycin resistant clones were never recovered when cells were transformed with pTRAS unless pTRAS additionally contained the neomycin resistance gene marker.

TABLE 1

Generation of paromomycin resistant clones following transformation of Tetrahymena cells with pD5H8, pTRAS and pTRAS + neomycin resistance gene marker

| Transformation | pD5H8 | pTRAS | pTRAS + Neomycin resistance gene marker |
|---|---|---|---|
| 1 | + | 0 | + |
| 2 | + | 0 | + |
| 3 | + | 0 | + |

Generation of paromomycin resistant clones following transformation of Tetrahymena cells with pD5H8, pTRAS and pTRAS + Neomycin resistance gene marker. Transformations were carried out three times. A + symbol denotes the recovery of paromomycin resistant colonies whereas 0 indicates the absence of paromomycin resistant clones following transformation.

REFERENCES

1. Pan, W. C., Orias, E., Flacks, M., and Blackburn, E. H. (1982). Allele-specific, selective amplification of a ribosomal RNA gene in Tetrahymena thermophila. Cell 3, 595-604.

2. Orias, E., Larson, D., Hu, Y. F., Yu, G. L., Karttunen, J., Lovlie, A., Haller, B., and Blackburn, E. H. (1988). Replacement of the macronuclear ribosomal RNA genes of a mutant *Tetrahymena* using electroporation. Gene 2, 295-301.
3. Yu, G. L., and Blackburn, E. H. (1989). Transformation of *Tetrahymena thermophila* with a mutated circular ribosomal DNA plasmid vector. Proc. Natl. Acad. Sci. U.S.A. 21, 8487-8491.
4. Yu, G. L., Hasson, M., and Blackburn, E. H. (1988). Circular ribosomal DNA plasmids transform *Tetrahymena thermophila* by homologous recombination with endogenous macronuclear ribosomal DNA. Proc. Natl. Acad. Sci. U.S.A. 14, 5151-5155.
5. Spangler, E. A., and Blackburn, E. H. (1985). The nucleotide sequence of the 17S ribosomal RNA gene of *Tetrahymena thermophila* and the identification of point mutations resulting in resistance to the antibiotics paromomycin and hygromycin. J. Biol. Chem. 10, 6334-6340.
6. Bruns, P. J., Katzen, A. L., Martin, L., and Blackburn, E. H. (1985). A drug-resistant mutation in the ribosomal DNA of *Tetrahymena*. Proc. Natl. Acad. Sci. U.S.A. 9, 2844-286.
7. Blomberg, P., Randolph, C., Yao, C. H., and Yao, M. C. (1997). Regulatory sequences for the amplification and replication of the ribosomal DNA minichromosome in *Tetrahymena thermophila*. Mol. Cell. Biol. 12, 7237-747.
8. Bruns, P. J., and D. Cassidy-Hanley, 2000. Biolistic Transformation of Macro and Micronuclei, in *Methods in Cell Biology: Tetrahymena thermophila*, eds. D. Asai and J. Formey, Acdemic Press (San Diego).
9. Cassidy-Hanley D. M., Bowen J., Lee J. H., Cole E., VerPlank L. A., Gaertig J., Gorovsky M. A., and Bruns P. J. (1997) Germline and somatic transformation of mating *Tetrahymena thermophila* by particle bombardment. Genetics 146(1), 135-147.
10. Karrer K M and Gall J G (1976) The Macronuclear Ribosomal DNA of *Tetrahymena pyriformis* is a Palindrome. J Mol Biol, 140, 421-453.
11. King B O and Yao M-C (1982) Tandemly Repeated Hexanucleotide at *Tetrahymena* rDNA Free End is Generated from a Single Copy during Development. Cell 31, 177-182.
12. Yao M-C, Yao C-H and Monks B (1990) The Controlling sequence for Site-Specific Chromosome Breakage in *Tetrahymeno*. Cell 63, 763-772.
13. Macalpine D M, Zhang Z and Kapler G M. (1997) Type I elements mediate replication fork pausing at conserved upstream sites In the *Tetrahymena thermophila* ribosomal DNA minichromosome. Mol. Cell. Biol. 17, 4517-4525
14. Pan W J, Gallagher R C and Blackburn E H. (1995) Replication of an rrna gene origin plasmid in the *Tetrahymena thermophila* Macronucleus is prevented by transcription through the origin from an RNA polymerase I promoter. Mol. Cell. Biol. 15, 3372-3381
15. Larson D D, Blackburn E H, Yaeger P C, and Orias E (1986) Control of rdna replication in *tetrahymena* involves a as-acting upstream repeat of a promoter element. Cell 47, 229-240.
16. Yaeger P C, Orias E, Shaiu W L, Larson D D and Blackburn E H (1989) The replication advantage of a free linear rdna gene is l~estored by somatic recombination in *tetrahymena thermophila* Mol. Cell. Biol. 9, 452-460.
17. Gaertig J, Gu L, Hai B and Gorovsky M A (1994) High frequency vector-mediated transformation and gene replacement in *Tetrahymena*. Nucleic Acids Res. 11, 5391-5398.
18. Turkewitz A P, Orias E and Kapler G (2002) Functional genomics: the coming of age for *Tetrahymena thermophila*. Trends Genet. 18, 35-40.
19. Frankel, J. (2000). Cell biology of *Tetrahymena thermophila*. Methods Cell Biol. 27-125.
20. Hellenbroich D, Valley U, Ryll T, Wagner R, Tekkanat N, Kessler W, Ross A and Deckwer W D (1999) Cultivation of *Tetrahymena thermophila* in a 1.5-m3 airlift bioreactor. Appl. Microbiol. Biotechnol. 51, 447-455.
22. de Coninck, J., Bouquelet, S., Dumortier, V., Duyme, F., and Verdier-Denantes, I. (2000). Industrial media and fermentation processes for improved growth and protease production by *Tetrahymena thermophila* BIII. J. Industr. Microbiol. Biotech. 4, 285.
23. Skriver L and Williams N E (1980) Regeneration of cilia in starved *Tetrahymena thermophila* involves induced synthesis of ciliary polypeptides but not synthesis of membrane lipids. Biochem. J. 188, 695-704.
24. Taniguchi, T., Mizuochi, T., Banno, Y., Nozawa, Y., and Kobata, A. (1985). Carbohydrates of lysosomal enzymes secreted by *Tetrahymena pyriformis*. J. Biol. Chem. 26, 13941-13946.
25. Weide, T., Herrmann, L., Bockau, U., Niebur, N., Aldag, I., Laroy, W., Contreras, R., Tiedtke, A., and Hartmann, M. W. (2006). Secretion of functional human enzymes by *Tetrahymena thermophila*. BMC Biotechnol. 19.
26. Yao M C, Zheng K and Yao C H (1987) A conserved nucleotide sequence at the sites of developmentally regulated chromosomal breakage in *Tetrahymena*. Cell. 48, 779-788.
27. Yu G L and Blackburn E H (1991) Developmentally programmed healing of chromosomes by telomerase in *Tetrahymena*. Cell. 67, 823-832.
28. Tondravi M M and Yao M C (1986) Transformation of *Tetrahymena thermophila* by microinjection of ribosomal RNA genes. Proc. Natl. Acad. Sci. USA. 83, 4369-4373.
29. Wuitschick J D and Karrer K M (1999) Analysis of genomic G+C content, codon usage, initiator codon context and translation termination sites in *Tetrahymena thermophila*. Eukaryot. Microbiol. 46, 239-247.
30. Gaertig J and Gorovsky M A (1992) Efficient mass transformation of *Tetrahymena thermophila* by electroporation of conjugants. Proc. Natl. Acad. Sci. USA. 89, 9196-9200.
31. Sweeney R, Yao C H, and Yao M C (1991) A Mutation in the Large Subunit Ribosomal RNA Gene of *Tetrahymena* Confers Anisomycin Resistance and Cold Sensitivity. *Tetrahymena thermophila* mutants defective in the developmentally programmed maturation and maintenance of the rDNA minichromosome. Genetics. 1991 February; 127 (2):327-334
32. Kapler G M, Orias E, Blackburn E H. A weak germ-line excision mutation blocks developmentally controlled amplification of the rDNA minichromosome of *Tetrahymena thermophila*. Kapler G M, Blackburn E H. Genes Dev. 1994 January; 8(1):84-95.b
33. R. S. Coyne and M. C. Yao. Evolutionary Conservation of Sequences Directing Chromosome Breakage and Rdna Palindrome Formation in Tetrahymenine Ciliates. Genetics. 1996 December; 144(4): 1479-1487.
34. Kapler G M, Blackburn E H. 1994 A weak germ-line excision mutation blocks developmentally controlled amplification of the rDNA mini-chromosome of *Tetrahymena thermophila*. Genes Dev. 8:84-95.
35. Yakisich J S, and Kapler G M. Deletion of the *Tetrahymena thermophila* rDNA replication fork barrier region disrupts macronuclear rDNA excision and creates a fragile site in the micronuclear genome. Nucleic Acids Res. 2006 Jan. 30; 34(2):620-34.

What is claimed is:

1. A nucleic acid construct comprising:
   a) a selection cassette encoding a resistance marker,
   b) a transgene cassette encoding a recombinant polypeptide, and
   c) a C3 allele rDNA locus comprising a 17S rDNA gene that does not confer paromomycin resistance to a ciliate transformed with the nucleic acid construct.

2. The nucleic acid construct of claim 1, wherein the construct is a linear DNA or RNA.

3. The nucleic construct of claim 1, wherein the construct is a circular DNA or RNA.

4. The nucleic acid construct of claim 1, wherein the construct is a vector, a plasmid, a cosmid, a chromosome or minichromosome, a transposon, an rDNA or any combination thereof.

5. The nucleic acid construct of claim 4, wherein the vector is an rDNA vector.

6. The nucleic acid construct of claim 1, wherein the selection cassette does not confer paromomycin resistance to a ciliate transformed with the nucleic acid construct.

7. The nucleic acid construct of claim 1, wherein the 17S rDNA gene is a B allele 17S rRNA.

8. A method for producing a recombinant polypeptide in a ciliate, the method comprising:
   a) transforming the ciliate with the vector of claim 1,
   b) culturing the ciliate and expressing the recombinant polypeptide, and
   c) isolating the recombinant polypeptide.

9. A genetically modified ciliate comprising a nucleic acid construct comprising:
   (a) a selection cassette encoding a resistance marker,
   (b) a transgene cassette encoding a recombinant polypeptide, and
   (c) a C3 allele rDNA locus comprising a 17S rDNA gene that does not confer paromomycin resistance to a ciliate transformed with the nucleic acid construct.

10. The genetically modified ciliate of claim 9, wherein the ciliate comprises a modification of a micronuclear rDNA locus nucleotide sequence.

11. The genetically modified ciliate of claim 10, wherein the modification of the micronuclear rDNA locus nucleotide sequence results in the formation of a non-functional rDNA chromosome after sexual conjugation of the ciliate.

12. The genetically modified ciliate of claim 10, wherein the ciliate has a conditionally conjugation-lethal phenotype.

13. The genetically modified ciliate of claim 10, wherein the modification of the micronuclear rDNA locus nucleotide sequence is a modification of an rDNA gene selected from the group comprising 5.8S, 17S and 26S.

14. The genetically modified ciliate of claim 10, wherein the modification is selected from the group consisting of: a deletion, an insertion, a substitution or an inversion.

15. The genetically modified ciliate of claim 9, wherein the ciliate comprises one or more non-functional rDNA genes selected from the group consisting of a non-functional 5.8S rRNA gene, a non-functional 17S rRNA gene, and a non-functional 26S rRNA gene.

16. The genetically modified ciliate of claim 9, wherein the nucleic acid construct is an rDNA vector.

17. The genetically modified ciliate of claim 16, wherein the rDNA vector is an rDNA rescue vector.

18. The genetically modified ciliate of claim 9, wherein the nucleic acid construct is present episomally in the ciliate.

19. The genetically modified ciliate of claim 9, wherein the nucleic acid construct is integrated in the micronuclear genome of the ciliate.

20. The genetically modified ciliate of claim 9, wherein the nucleic acid construct is integrated in the macronuclear genome of the ciliate.

21. The genetically modified ciliate of claim 9, wherein the nucleic acid construct is self-replicating.

22. The genetically modified ciliate of claim 9, wherein the ciliate is a *Tetrahymena* species.

23. The genetically modified ciliate of claim 22, wherein the *Tetrahymena* species is *Tetrahymena thermophila*.

24. The genetically modified ciliate of claim 9, wherein the selection cassette encoding a resistance marker, the transgene cassette encoding a recombinant polypeptide, and the C3 allele rDNA locus comprising a 17S rDNA gene that does not confer paromomycin resistance of the nucleic acid construct are bounded by a 5' and a 3' Chromosome Breakage Sequence.

25. The genetically modified ciliate of claim 24, wherein macronuclear reorganization in the ciliate results in the formation of a macronuclear minichromosome capable of expressing the resistance marker and the recombinant polypeptide.

26. A method for producing a recombinant polypeptide in a ciliate, the method comprising:
   a) causing the ciliate to undergo sexual reproduction by conjugation;
   b) transforming a genetically modified ciliate with a nucleic acid construct comprising:
      (i) a selection cassette encoding a resistance marker,
      (ii) a transgene cassette encoding a recombinant polypeptide, and
      (ii) a C3 allele rDNA locus comprising a 17S rDNA gene that does not confer paromomycin resistance to a ciliate transformed with the nucleic acid construct,
   c) culturing the genetically modified ciliate to produce the recombinant polypeptide; and
   d) isolating the recombinant polypeptide.

* * * * *